(12) United States Patent
Gatzemeyer et al.

(10) Patent No.: US 11,484,253 B2
(45) Date of Patent: Nov. 1, 2022

(54) ORAL CARE SYSTEM

(71) Applicant: Colgate-Palmolive Company, New York, NY (US)

(72) Inventors: John Gatzemeyer, Hillsborough, NJ (US); Daniel Roman, Denville, NJ (US)

(73) Assignee: Colgate-Palmolive Company, New York, NY (US)

( * ) Notice: Subject to any disclaimer, the term of this patent is extended or adjusted under 35 U.S.C. 154(b) by 503 days.

(21) Appl. No.: 16/720,480

(22) Filed: Dec. 19, 2019

(65) Prior Publication Data
US 2021/0186414 A1 Jun. 24, 2021

(51) Int. Cl.
| A46B 13/02 | (2006.01) |
| A46B 15/00 | (2006.01) |
| A61B 5/00 | (2006.01) |
| A46B 9/04 | (2006.01) |

(52) U.S. Cl.
CPC .............. *A61B 5/4547* (2013.01); *A46B 9/04* (2013.01); *A46B 13/023* (2013.01); *A46B 15/004* (2013.01); *A46B 15/0008* (2013.01); *A46B 15/0044* (2013.01); *A46B 15/0046* (2013.01)

(58) Field of Classification Search
CPC . A46B 13/023; A46B 15/0008; A46B 15/004; A46B 15/0038; A46B 15/0044; A46B 15/0046
See application file for complete search history.

(56) References Cited

U.S. PATENT DOCUMENTS

| 6,468,076 | B2 | 10/2002 | Kawamura |
| 6,685,471 | B1 | 2/2004 | Kawamura et al. |
| 6,954,961 | B2 | 10/2005 | Ferber et al. |
| 7,120,960 | B2 | 10/2006 | Hilscher et al. |
| 7,861,349 | B2 | 1/2011 | Hilscher et al. |
| 8,075,315 | B2 | 12/2011 | Gatzenmeyer et al. |

(Continued)

FOREIGN PATENT DOCUMENTS

| GB | 2555417 | 5/2018 |
| WO | 1998/15236 | 4/1998 |

(Continued)

OTHER PUBLICATIONS

Oral-B Genius Brushing Features, https://oralb.com/en-us/products/compare/genius, retrieved Dec. 4, 2019, pp. 1-6.

*Primary Examiner* — Randall E Chin

(57) ABSTRACT

An oral care implement including a handle and an oral care refill head. The handle has a gripping portion, an engagement component coupled to a distal end of the gripping portion, and a stem. The engagement component includes a plate portion and a first engagement feature. The stem extends through an opening in the engagement component and protrudes from the plate portion. The oral care refill head includes an oral care treatment portion and a sleeve portion. The sleeve portion has an inner surface that defines a sleeve cavity having a cavity axis and a second engagement feature. When the oral care refill head is detachably coupled to the handle, the first and second engagement features mate with one another to at least one of: (1) position the oral care refill head and the handle in an operational alignment; and (2) lock the oral care refill head to the handle.

20 Claims, 30 Drawing Sheets

(56) References Cited

U.S. PATENT DOCUMENTS

| | | |
|---|---|---|
| 8,201,295 B2 | 6/2012 | Gatzenmeyer et al. |
| 8,214,958 B2 | 7/2012 | Pinyayev et al. |
| 8,311,302 B2 | 11/2012 | Yan et al. |
| 8,337,213 B2 | 12/2012 | Puurunen et al. |
| 8,358,203 B1 | 1/2013 | Perry |
| 8,585,411 B2 | 11/2013 | Puurunen et al. |
| 8,839,476 B2 | 9/2014 | Adachi |
| 9,044,083 B2 | 6/2015 | Nanda |
| 9,168,117 B2 | 10/2015 | Yoshida et al. |
| 9,220,583 B2 | 12/2015 | Shani et al. |
| 9,301,821 B2 | 4/2016 | Fattori |
| 9,345,408 B2 | 5/2016 | Curry et al. |
| 9,848,968 B2 | 12/2017 | Jungnickel et al. |
| 9,870,613 B2 | 1/2018 | Wu et al. |
| 9,882,986 B2 | 1/2018 | Patel |
| 10,172,443 B2 | 1/2019 | Wang et al. |
| 10,258,142 B2 | 4/2019 | Knickerbocker et al. |
| 10,271,934 B2 | 4/2019 | Huy et al. |
| 10,349,733 B2 | 7/2019 | Serval et al. |
| 2007/0261185 A1 | 11/2007 | Guney et al. |
| 2012/0171657 A1 | 7/2012 | Ortins et al. |
| 2013/0000670 A1 | 1/2013 | Binner et al. |
| 2016/0113495 A1 | 4/2016 | Nanjundappa et al. |
| 2016/0242652 A1 | 8/2016 | Van Putten et al. |
| 2017/0263149 A1* | 9/2017 | Sullivan ............. A46B 15/0004 |
| 2018/0168332 A1 | 6/2018 | Wagner et al. |
| 2019/0038014 A1* | 2/2019 | Greer, Jr. ........... A46B 15/0044 |
| 2019/0082819 A1 | 3/2019 | Katano et al. |

FOREIGN PATENT DOCUMENTS

| | | |
|---|---|---|
| WO | 2010/106524 | 9/2010 |
| WO | 2014/037888 | 3/2014 |
| WO | 2016/046701 | 3/2016 |
| WO | 2016/176783 | 11/2016 |
| WO | 2017/029469 | 2/2017 |

* cited by examiner

Normal Mode

First Sensor Unit: Active
Sensor Indicator Unit: Active
Motion Inducing Unit: Active

Quiet Mode

First Sensor Unit: Active
Sensor Indicator Unit: Inactive
Motion Inducing Unit: Active

FIG. 4

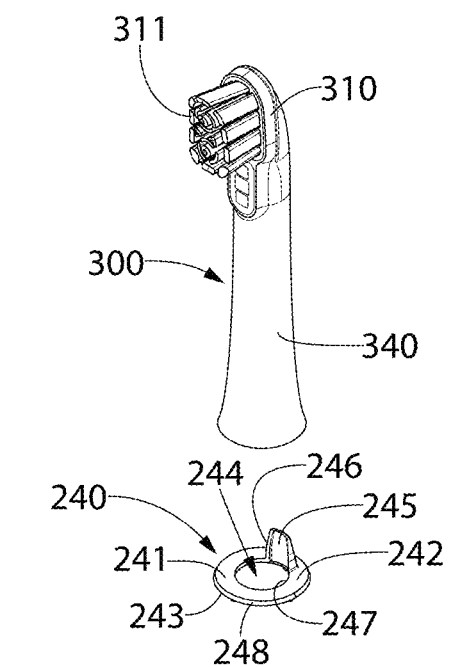
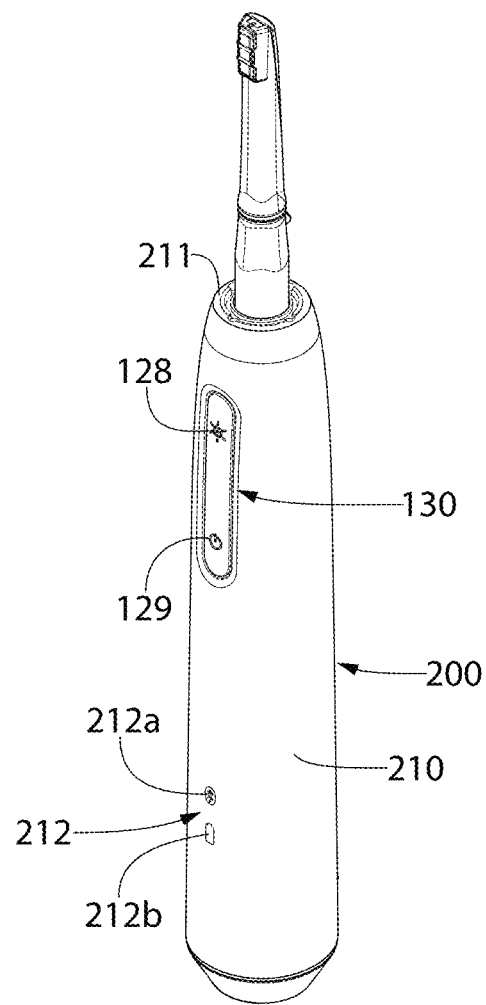
FIG. 6

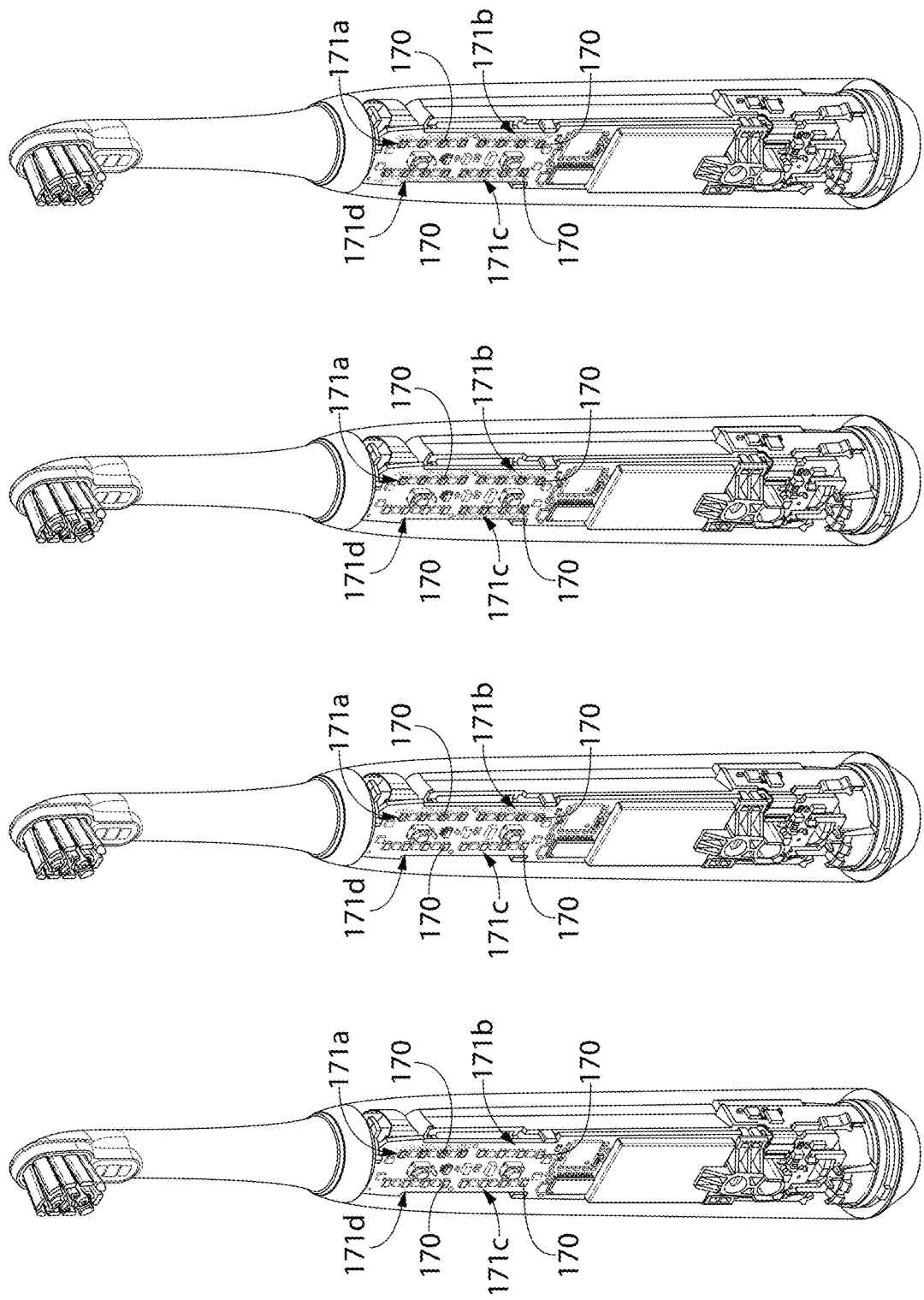

ORAL CARE SYSTEM

BACKGROUND

In the era of smart devices and people's desire to track personalized data related to their health and wellness, many new industries have sprung up. Additionally, people have been coming up with ways to track activities that were being undertaken but not previously tracked. The act of toothbrushing and related oral hygiene procedures is one area in which such tracking has been found to be desirable. Specifically, individuals want to know how well they are brushing their teeth, how long they are brushing their teeth, and they want to be able to interact with a screen that can provide them with information about their toothbrushing habits. However, there is still much room for improvement in the manner in which information about a user's oral hygiene habits is provided to the user and the user's ability to control that flow of information. Furthermore, there is a need to improve the mechanism used for connecting a refill head to a handle for toothbrushes with such tracking capabilities in order to protect any electronic components from being damaged by fluids. These and other needs are met by the invention described herein below.

BRIEF SUMMARY

The present invention is directed to an oral care system that monitors an oral care parameter of a user during an oral care session and allows a user to control whether feedback related to the oral care parameter is provided to the user in real time. The present invention is also directed to an oral care implement that includes a handle and a refill head with a unique connection mechanism. The present invention is further directed to an oral care system that can generate different user perceptible stimulus depending on the detection of an oral malady in real-time during an oral care session. The present invention is still further directed to an oral care system that can provide a user with an indication of an amount of time that has elapsed during an oral care session in an easily identifiable manner.

In one aspect, the invention may be an oral care system comprising: an oral care implement comprising an oral care tool for treating an oral cavity of a user; a control circuit comprising, in operable cooperation: a power source integrated into the oral care implement; a first sensor unit integrated into the oral care implement and configured to monitor an oral care parameter during performance of an oral care session using the oral care implement; a sensor indicator unit integrated into the oral care implement and configured to generate user perceptible stimuli during the oral care session upon the first sensor unit detecting that the monitored oral care parameter meets a certain criteria; a memory unit configured to store data relating to the monitored oral care parameter; and a mode selection unit configured to allow a user to select between both of a normal mode and a quiet mode for performance of the oral care session; wherein upon selection of the normal mode by the user for the oral care session: (i) the first sensor unit is active during the oral care session; (ii) the sensor indicator unit is active during the oral care session; and (iii) the data relating to the monitored oral care parameter is stored in the memory unit during the oral care session; and wherein upon selection of the quiet mode by the user for the oral care session: (i) the first sensor unit is active during the oral care session; (ii) the sensor indicator unit is inactive during the oral care session; and (iii) the data relating to the monitored oral care parameter is stored in the memory unit during the oral care session.

In another aspect, the invention may be an oral care system comprising: an oral care implement comprising an oral care tool for treating an oral cavity of a user; a control circuit configured to operate the oral care implement in at least two user selectable modes comprising a normal mode and a quiet mode; wherein upon selection of the normal mode by the user for an oral care session: (i) a first sensor unit configured to detect a physiological oral care condition during the oral care session is active; and (ii) a sensor indicator unit that generates user perceptible stimuli during the oral care session in response to the detection of the physiological oral care condition is active; and wherein upon selection of the quiet mode by the user for an oral care session: (i) the first sensor unit is active during the oral care session; and (ii) the sensor indicator unit is inactive during the oral care session.

In yet another aspect, the invention may be a method of operating an oral care implement of an oral care system during an oral care session, the oral care system comprising a control circuit configured to operate the oral care implement in at least two user selectable modes comprising a normal mode and a quiet mode, the method comprising: a) receiving a user mode selection selecting a desired one of the normal mode and the quiet mode from the at least two user selectable modes; b-1) upon the user mode selection being the normal mode, the oral care implement being activated so that: (i) a first sensor unit is active and monitors for a physiological oral care condition during the oral care session; and (ii) a sensor indicator unit is active and generates user perceptible stimuli during the oral care session in response to the physiological oral care condition being detected by the first sensor unit; and b-2) upon the user mode selection being the quiet mode, the oral care implement being activated so that: (i) the first sensor unit is active and monitors for the physiological oral care condition during the oral care session; and (ii) the sensor indicator unit is inactive during the oral care session.

In a further aspect, the invention may be an oral care implement comprising: a handle comprising: a gripping portion having a distal end; and an engagement component coupled to the distal end of the gripping portion, the engagement component comprising: a plate portion comprising a top surface and an aperture; and a first engagement feature; and a stem extending through the opening in the engagement component and protruding from the plate portion so that the top surface of the plate portion forms an annular shoulder that circumscribes the stem; an oral care refill head comprising: an oral care treatment portion; and a sleeve portion comprising an inner surface that defines a sleeve cavity having a cavity axis, the sleeve portion comprising a second engagement feature; the oral care refill head alterable between: a first state in which the oral care refill head is separated from the handle; and a second state in which the stem of the handle is disposed within the sleeve cavity of the sleeve portion, wherein in the second state the first and second engagement features mate with one another to at least one of: (1) position the oral care refill head and the handle in an operational alignment; and (2) lock the oral care refill head to the handle.

In a still further aspect, the invention may be an oral care refill head for detachable coupling to a stem of a handle, the oral care refill head comprising: an oral treatment portion comprising a plurality of tooth cleaning elements protruding from a front surface of a head body; and a sleeve portion extending from the oral treatment portion to a proximal edge, the sleeve portion comprising: a front surface that faces the same direction as the front surface of the head body and a rear surface opposite the front surface; an inner surface defining a sleeve cavity extending along a sleeve axis and configured to receive the stem of the handle; a window aperture formed into the front surface at a location that is adjacent to the plurality of tooth cleaning elements; a locking aperture formed into the rear surface and configured to snap-interlock with a locking protuberance of the stem of the handle; and a plurality of ribs extending from the inner surface of the sleeve portion in a circumferentially spaced apart manner, the plurality of ribs defining a plurality of channels that include an alignment channel having a greater width than a remainder of the plurality of channels so that the alignment channel is the only one of the plurality of channels capable of receiving an alignment protrusion of the handle.

In yet another aspect, the invention may be an oral care refill head for detachable coupling to a stem of a handle, the oral care refill head comprising: an oral treatment portion comprising a plurality of tooth cleaning elements; and a sleeve portion extending from the oral treatment portion to a proximal edge, the sleeve portion comprising: an inner surface defining a sleeve cavity extending along a sleeve axis and configured to receive the stem of the handle; a window aperture adjacent to the plurality of tooth cleaning elements; and an elongated alignment rib extending from the inner surface of the sleeve portion, at least a portion of the elongated alignment rib being aligned with and visible through the window aperture, the elongated alignment rib configured to press against the stem of the handle to force a first sensor unit on the stem to extend through the window aperture.

In another aspect, the invention may be an oral care refill head for detachable coupling to a stem of a handle, the oral care refill head comprising: an oral treatment portion comprising a plurality of tooth cleaning elements protruding from a front surface of a head body; and a sleeve portion extending from the oral treatment portion to a proximal edge, the sleeve portion comprising: a front surface that faces the same direction as the front surface of the head body and a rear surface opposite the front surface; an inner surface defining a sleeve cavity extending along a sleeve axis and configured to receive the stem of the handle; a window aperture formed into the front surface at a location that is adjacent to the plurality of tooth cleaning elements; and a locking aperture formed into the rear surface and configured to snap-interlock with a locking protuberance of the stem of the handle.

In a further aspect, the invention may be a handle for detachably coupling to an oral care refill head, the handle comprising: a gripping portion having a distal end; and an engagement component coupled to the distal end of the gripping portion, the engagement component comprising: a plate portion comprising a top surface and an aperture; and a first engagement feature configured to mate with an engagement feature of the oral care refill head to at least one of: (1) position the oral care refill head and the handle in an operational alignment; and (2) lock the oral care refill head to the handle; and a stem extending along a stem axis through the opening in the engagement component and protruding from the plate portion so that the top surface of the plate portion forms an annular shoulder that circumscribes the stem.

In a still further aspect, the invention may be a handle for detachably coupling to an oral care refill head, the handle comprising a gripping portion having a distal end; and a stem extending from the distal end of the gripping portion so that the distal end of the gripping portion forms an annular shoulder that circumscribes the stem; and an alignment protrusion extending from the annular shoulder, the alignment protrusion configured to mate with an alignment feature of the oral care refill head to position the oral care refill head and the handle in an operational alignment; and wherein the alignment protrusion a separate component from the stem.

In another aspect, the invention may be an oral care system comprising: an oral care implement comprising an oral care tool for treating an oral cavity of a user; a control circuit comprising, in operable cooperation: a first sensor unit coupled to the oral care implement and configured to detect: (1) presence of an oral surface during performance of an oral care session using the oral care implement; and (2) presence of an oral malady on the oral surface during performance of the oral care session; a sensor indicator unit configured to generate user perceptible stimuli during the oral care session: the control circuit configured to: generate a first user perceptible stimulus with the sensor indicator unit during the oral care session when the first sensor unit is detecting the presence of the oral surface and the presence of the oral malady on the oral surface; generate a second user perceptible stimulus with the sensor indicator unit during the oral care session when the first sensor unit is detecting the presence of the oral surface and that the oral surface is free of the oral malady; and generate a third user perceptible stimulus with the sensor indicator unit during the oral care session when the first sensor unit is not detecting the presence of the oral surface, wherein the first, second, and third user perceptible stimuli are different from one another.

In still another aspect, the invention may be an oral care system comprising: an oral care implement comprising an oral care tool for treating an oral cavity of a user; a control circuit comprising, in operable cooperation: a first sensor unit coupled to the oral care implement and configured to detect presence of an oral malady on an oral surface of the user's oral cavity during performance of an oral care session with the oral care implement; a timer unit configured to track time during performance of the oral care session; a second sensor unit configured to determine orientation of the oral care implement during the oral care session; and an indicator unit configured to generate a first user perceptible stimulus during the oral care session; the control circuit configured to: start a zone timer of the timer unit upon determining that the oral care tool has started treating a zone of the user's oral cavity; upon a first time period having passed, activating the indicator unit to generate the first user perceptible stimulus if the first sensor unit is not detecting the presence of the oral malady in the zone, thereby signaling the user to move the oral care tool to a next zone of the user's oral cavity; upon the first time period having passed, continuing to run the timer unit without activating the indicator unit to generate the first user perceptible stimulus if the first sensor unit is detecting the presence of the oral malady in the zone; and upon a second time period having passed, activating the indicator unit to generate the first user perceptible stimulus even if the first sensor unit is still detecting the presence of the oral malady in the zone, thereby signaling the user to move the oral care tool to a next zone of the user's oral cavity, wherein the second time period is greater than the first time period.

In a further aspect, the invention may be a powered oral care implement comprising: a head comprising an oral care tool; a handle comprising a gripping portion; a user-operated actuator on the handle for controlling one or more functions of the oral care implement; an illumination ring on the handle that surrounds the user operated actuator; a control circuit comprising, in operable cooperation; a power source; an actuator unit in operable cooperation with the user-operated actuator; a timer unit configured to track time during performance of the oral care session; a time indicator unit comprising: one or more light sources positioned to illuminate the illumination ring; and the control circuit configured to activate the one or more light sources in a manner that informs the user, during the oral care session, of the time that has passed during performance of the oral care session.

In a still further aspect, the invention may be a powered oral care implement comprising: a head comprising an oral care tool; a handle comprising a gripping portion; a user-operated actuator on the handle for controlling one or more functions of the oral care implement; an illumination ring on the gripping portion of the handle, the illumination ring having a continuous exposed ring surface that surrounds the user operated actuator; a control circuit comprising, in operable cooperation, a power source, an actuator unit in operable cooperation with the user-operated actuator, and one or more light sources; and a light divider component comprising a body having a plurality of arcuate apertures arranged in a ring and separated from one another by divider walls, the light divider component mounted in the handle housing of the gripping portion so that the ring formed by the plurality of arcuate apertures is aligned with the illumination ring.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 4 is a diagram illustrating which components of the control circuit are active and inactive in the various modes of operation;

FIG. 6 is a front perspective view of the oral care implement of FIG. 5 with an oral care refill head and an engagement component detached from a handle;

FIGS. 22A-22D are perspective views of the oral care implement of FIG. 1 with a handle housing thereof shown transparent illustrating progressive illumination of light sources of a time indicator unit thereof over the passage of time;

DETAILED DESCRIPTION

Figure 1:
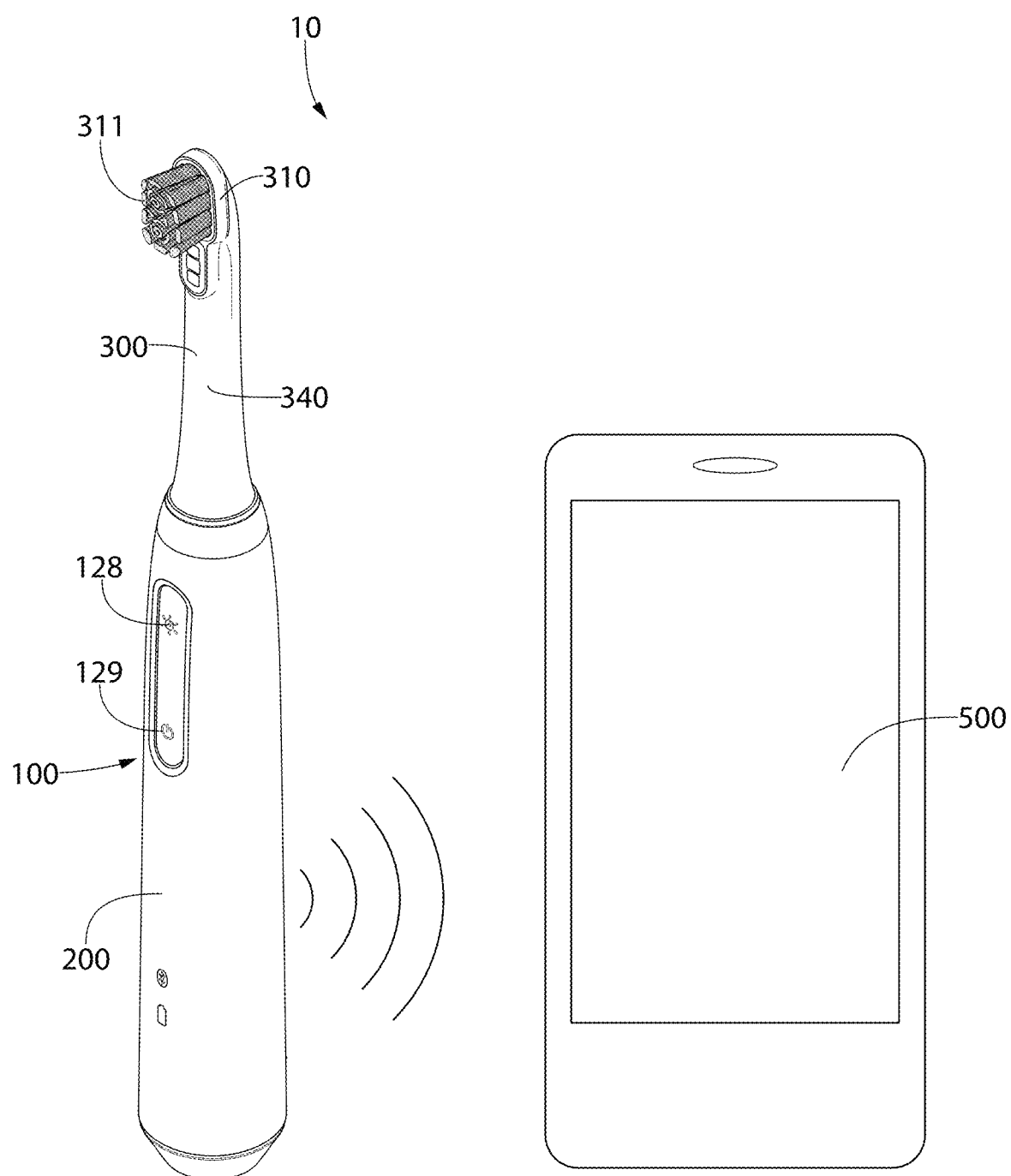
FIG. 1 illustrates an oral care system that includes an oral care implement that is in operable communication with an electronic device in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached,"

"affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Features of the present invention(s) may be implemented in software, hardware, firmware, or combinations thereof. In particular, the various units that form a part of the control circuit described herein may comprise software, hardware, firmware, and combinations thereof. Each such "unit" may comprise its own processor, or it may be coupled to a processer that is used for all components of the control circuit, or some combination of this may occur. The computer programs described herein are not limited to any particular embodiment, and may be implemented in an operating system, application program, foreground or background processes, driver, or any combination thereof. The computer programs may be executed on a single computer or server processor or multiple computer or server processors.

Processors (also referred to as controllers) described herein may be any central processing unit (CPU), microprocessor, micro-controller, computational, or programmable device or circuit configured for executing computer program instructions (e.g., code). Various processors may be embodied in computer and/or server hardware of any suitable type (e.g., desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc. In one particular embodiment, a processor unit may reside on the device (oral care implement as described herein) itself and all processing can be done internally and integrally on the device without limitation and without the need of any outside resource.

Computer-executable instructions or programs (e.g., software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. A device embodying a programmable processor configured to such non-transitory computer-executable instructions or programs may be referred to as a "programmable device," or "device," and multiple programmable devices in mutual communication may be referred to as a "programmable system." It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g., internal/external hard disks, floppy discs, magnetic tape CD-ROM, DVD-ROM, optical disk, ZIP™ drive, Blu-ray disk, and others), which may be written to and/or read by a processor operably connected to the medium.

In certain embodiments, the present invention(s) may be embodied in the form of computer-implemented processes and apparatuses such as processor-based data processing and communication systems or computer systems for practicing those processes. The present invention(s) may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

Referring to FIG. 1, an oral care system 10 is illustrated in accordance with an embodiment of the present invention. The oral care system 10 generally comprises an oral care implement 100 and an electronic device 500. In the exemplified embodiment, the oral care implement 100 is a toothbrush and the electronic device 500 is a smart phone. However, the invention is not to be so limited in all embodiments and the oral care implement 100 could take on other structural forms, including being a powered or manual toothbrush, a tongue scraper, a gum and soft tissue cleanser, a water pick, an interdental device, a tooth polisher, a specially designed ansate implement having tooth engaging elements, or any other type of implement that is commonly used for oral care. Furthermore, in still other embodiments the implement may not be specifically used for oral care, but could instead be a personal care implement which includes the various types of oral care implements noted herein and also includes hairbrushes, razors, body scrubbers, skin treatment devices, or the like. Thus, it is to be understood that the inventive concepts discussed herein can be applied to any type of oral care implement or personal care implement unless a specific type of implement is specified in the claims. The structural and functional details of the oral care implement 100 will be provided below in accordance with exemplary embodiments of the present invention. Moreover, the electronic device 500 is not limited to being a smart phone, and it could be a computer, a laptop, a notebook, a tablet, any type of cellular phone, or other similar devices.

In embodiments that include the oral care implement 100 and the electronic device 500, those two devices are configured to be in operable communication with each other in some circumstances so that data monitored or acquired by one of the devices can be transmitted to the other for processing, storage, display, or other purposes. Furthermore, the operable communication may allow user interaction with the electronic device 500 to control the operation of the oral care implement 100. Still furthermore, the operable communication may allow an app that is launched on the electronic device 500 to control operation of the oral care implement 100. For example, if the app is designed to store data about an oral care session, upon the memory in the electronic device 500 (or the memory to which the app has access) becoming full, the electronic device 500 may power down the oral care implement 100.

The operable communication between the oral care implement and the electronic device 500 is illustrated in FIG. 1, and it may be achieved by wireless or hard wire techniques. For example, in some embodiments a wire may be coupled to the oral care implement 100 and to the electronic device 500 to place those two devices into operable communication with one another. In other embodiments, wireless techniques may be used including Bluetooth, Wi-Fi, LAN, Zigbee, infrared, RFID, or the like. However, in other embodiments the oral care system 10 may comprise the oral care implement 100 by itself without the electronic device 500 and all of the data acquisition and processing may take place within the oral care implement 100. Thus, while the drawings show some exemplary embodiments of the invention, it should be appreciated that the invention is not to be limited solely by those exemplary embodiments. Rather, the scope of the invention as described herein covers variations that are not shown explicitly in the drawings but that are explicitly described and/or claimed.

As shown in FIG. 1, the oral care implement 100 comprises a handle 200 and an oral care refill head 300. In the exemplified embodiment the oral care refill head 300 is detachably coupled to the handle 200 so that the oral care refill head 300 can be replaced when the cleaning elements thereof become worn. Details regarding the connection mechanism(s) that facilitate the coupling between the oral care refill head 300 and the handle 200 will be provided below. In other embodiments, the oral care implement 100 may be an integral or monolithic structure that includes the handle 200 and the head such that the head is not detachable from the handle 200. As also shown in FIG. 1, the oral care implement 100 is in operable communication with the electronic device 500. In the exemplary embodiment, the oral care implement 100 and the electronic device 500 are wirelessly coupled, and the details of how this may be achieved will be provided below in accordance with an exemplary embodiment of the present invention.

The oral care refill head 300 may comprise an oral care treatment portion (also referred to herein as an oral care tool) 310 and a sleeve portion 340. In the exemplified embodiment, the oral care tool 310 comprises a plurality of tooth cleaning elements 311. The term "tooth cleaning elements" may be used in a generic sense to refer to any structure that can be used to clean, polish, or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, polybutylene terephthalate (PBT) bristles, spiral bristles, rubber bristles, elastomeric protrusions, flexible polymer protrusions, combinations thereof, and/or structures containing such materials or combinations. Thus, any combination of these tooth cleaning elements may be used within the tooth cleaning element field in some embodiments. Furthermore, where bristles are used for one or more of the tooth cleaning elements 311, such bristles can be tapered, end-rounded, spiral, or the like. The tooth cleaning elements 311 may be coupled to the oral care tool 310 using any known techniques such as staples, in-mold tufting, anchor-free tufting (AFT), PTT, or the like.

Figure 2:
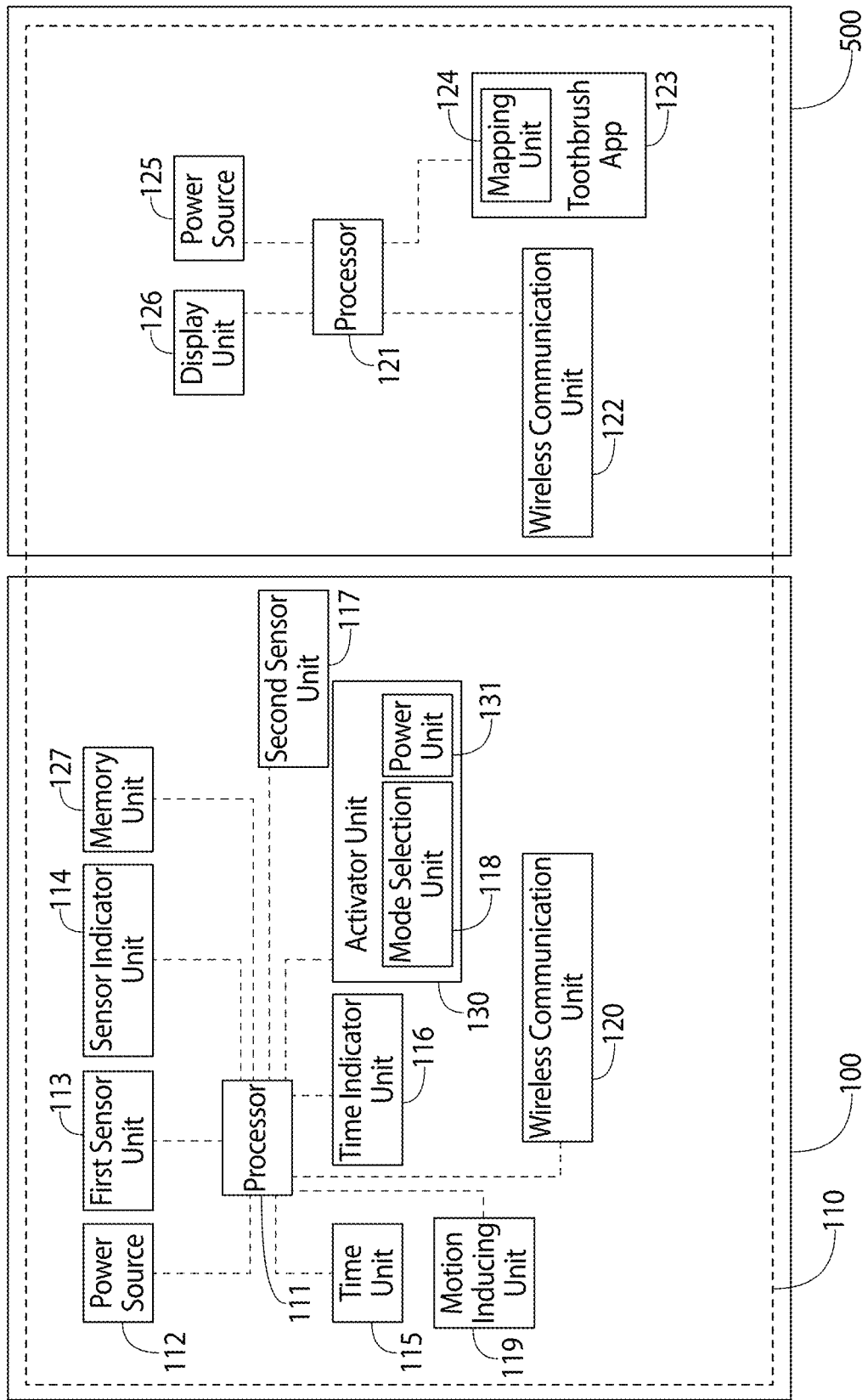
FIG. 2 is a block diagram of a control circuit of the oral care system of FIG. 1.

Referring to FIGS. 1 and 2, the oral care system 10 generally comprises the oral care implement 100 and a control circuit 110. The control circuit 110 comprises several different "units" and other electronic components that are in operable communication or operable cooperation with one another. As mentioned above, the term "unit" as used herein refers to an electronic component and its software, hardware, and processors, although the processors may be separate components that are coupled to the "unit" as shown in the embodiment of FIG. 2. As will be discussed below, in the exemplified embodiment there is a processor 111 associated with the oral care implement 100 and a processor 121 associated with the electronic device 500, and each of the electronic components of the control circuit 110 is operably coupled to one of the processors 111, 121. However, in other embodiments each of the "units" may have its own controller. In such embodiments, the various "units" may still be coupled to one of the controllers 111, 121, or they may not if they are able to process and transmit/receive data as needed for proper operation of the control circuit 110 as described herein.

In the exemplified embodiment, some components of the control circuit 110 are illustrated as being in the oral care implement 100 and other components of the control circuit 110 are illustrated as being in the electronic device 500. However, it should be appreciated that the invention is not limited to this exact configuration in all embodiments. Specifically, some of the components of the control circuit 110 that are depicted as being located in the oral care implement 100 may be located in the electronic device 500 in other embodiments and some of the components that are depicted as being located in the electronic device 500 may be located in the oral care implement 100 in other embodiments. The particular components of the control circuit 110 to which this applies will be noted below.

Furthermore, in the exemplified embodiment the components/units in the oral care implement 100 are depicted as being coupled to the processor 111 and the components/units in the electronic device 500 are depicted as being coupled to the processor 121. However, the invention is not to be so limited in all embodiments. Specifically, in some embodiments there may be one processor 121 common to all of the components/units of the control circuit 110. In other embodiments, at least some of the components/units of the control circuit 110 that are located in the oral care implement 100 may be operably coupled to the processor 121 of the electronic device 500. For example, various sensors in the oral care implement 100 may acquire data and then transmit that data to the processor 121 in the electronic device 500 in some embodiments. Furthermore, the processor 121 may be configured to control certain operation of the oral care implement 100 in some embodiments, such as power on/off, activation of the components, and the like.

In the exemplified embodiment, the following components of the control circuit 110 are located in the oral care implement 100 in operable cooperation: the processor 111, a power source 112, a first sensor unit 113, a sensor indicator unit 114, a timer unit 115 (which may include a zone timer and a session timer, as discussed below), a time indicator unit 116, a second sensor unit 117, an actuator unit 130 that comprises a mode selection unit 118 and a power unit 131, a motion inducing unit 119, a memory unit 127, and a first wireless communication unit 120. In the exemplified embodiment, the following components of the control circuit 110 are located in the electronic device 500 in operable cooperation: the processor 121, a second wireless communication unit 122, a toothbrush application 123 comprising a mapping unit 124, a power source 125, and a display unit 126. The first and second wireless communications units 120, 122 are configured for operable communication with one another, so that data monitored, acquired and/or processed by the control circuit 110 within the oral care implement 100 can be transmitted to the electronic device 500 and vice versa. Thus, in a sense, the components of the control circuit 110 that are located in the oral care implement may be in operable communication with one or more of the components of the control circuit 110 that are located in the electronic device 500.

As mentioned above, FIG. 2 illustrates one exemplary embodiment of the control circuit 110, but alternatives are possible and fall within the scope of the invention described herein. For example, in some embodiments the memory unit 127 may be located in the electronic device 500 instead of in the oral care implement 100. In other embodiments, there may be a memory unit located in each of the electronic device 500 and the oral care implement 100. In still other embodiments, the memory unit 127 may not be located in either of the oral care implement 100 or the electronic device 500, but it could be part of a separate component altogether. In some embodiments, the processors 111, 121 may comprise memory units therein, such that there may not be any stand-alone memory units distinct from the processors 111, 121. In some embodiments, the mode selection unit 118 may be located in the electronic device 500 instead of in the oral care implement 100. In some embodiments, the second sensor unit 117, or portions thereof, may be located in the electronic device 500 instead of in the oral care implement 100. Moreover, in some embodiments the mapping unit 124 may be integrated into the oral care implement 100 rather than the electronic device 500. Thus, with these potential modifications in mind, the full breadth and scope of the invention set forth herein should be appreciated.

With continued reference to FIG. 2, the various components of the control circuit 110 will be described in a bit more detail. However, it should be appreciated that even more detail will be provided later on in this document as some exemplary embodiments of the invention are described. Thus, the discussion with reference to FIG. 2 is intended to be more of an overview with an understanding that additional details in accordance with one or more specific structural and functional embodiments will be provided later on in this document.

In the exemplified embodiment, the power source 112 that is located in the oral care implement 100 may comprise one or more batteries. Moreover, in some embodiments the power source 112 may be omitted and the oral care implement 100 may operate via a direct coupling to a mains power. In still other embodiments, solar power or other power sources can be used to power the oral care implement. The power source 112 may be individually coupled to each of the components of the control circuit 110 that are located in the oral care implement 100, or the power source 112 may be coupled to the centralized processor 111, which can in turn transmit power from the power source 112 to each of the other components as needed. More than one more power 112 may be included in the oral care implement 100 as needed to provide sufficient power to all of the components of the control circuit 110.

The first sensor unit 113 is integrated into the oral care implement 100 and may be configured to monitor an oral care parameter during performance of an oral care session using the oral care implement 100. The oral care parameter may be a physiological condition of the user. For example, the oral care parameter may be the existence (or lack thereof) of bacteria, plaque, or tartar in the oral cavity. The oral care parameter may alternatively be the existence (or lack thereof) of dental caries or cavities, halitosis, gum disease, cancers, oral manifestations of HIV, and various other ailments that may affect the oral cavity. In the exemplified embodiment, the first sensor unit 113 comprises a plaque detection unit and the physiological condition or oral care parameter that is monitored may be the existence or lack thereof of plaque on oral surfaces of the user's oral cavity.

Thus, in the exemplified embodiment, the first sensor unit 113 comprises the necessary sensor(s) to enable it to detect the existence or lack thereof of plaque on a user's teeth and/or other oral surfaces. In one particular embodiment, the first sensor unit 113 may comprise a plaque detection unit that is configured to detect the presence or absence of plaque (or tartar or calculus or other similar tooth build-up) on the teeth. In such embodiments, the first sensor unit 113 may comprise an imaging device such as an optical sensor, which in one embodiment may be a camera or the like for obtaining images of the surfaces of the user's oral cavity to determine the presence or absence of plaque or other physiological oral conditions. The first sensor unit 113 may also (or alternatively) comprise light emitters, light source(s) transmitters, receivers, and various other hardware necessary to ensure that the first sensor unit 113 is capable of performing its intended sensing function (which, in the exemplified embodiment, may be the detection of plaque as noted herein). As mentioned above, the first sensor unit 113 may comprise a processor instead of or in addition to being coupled to the processor 111. Additional information regarding the first sensor unit 113 and the manner in which plaque may be detected in accordance with various embodiments of the present invention are disclosed in U.S. Pat. No. 9,220,583, issued Dec. 29, 2015, the entirety of which is incorporated herein by reference.

The sensor indicator unit 114 of the control circuit 110 is also integrated into the oral care implement 100 in the exemplified embodiment. The sensor indicator unit 114 is operably coupled to the first sensor unit 113 so that the sensor indicator unit 114 can generate user perceptible stimuli during an oral care session upon the first sensor unit 113 detecting that the monitored oral care parameter meets a certain criteria or threshold. In the exemplified embodiment, the first sensor unit 113 and the sensor indicator unit 114 are coupled to the processor 111. Thus, the first sensor unit 113 monitors the oral care parameter during performance of an oral care session and transmits data related to this monitoring to the processor 111. The processor 111 then processes this data and sends a signal to the sensor indicator unit 114 instructing the sensor indicator unit 114 whether or not to generate any of one or more user perceptible stimuli, and if so, which particular user perceptible stimuli to generate. In other embodiments, the first sensor unit 113 may be coupled directly to the sensor indicator unit 114, particularly in embodiments whereby the first sensor unit 113 and/or the sensor indicator unit 114 comprise their own processor.

The sensor indicator unit 114 comprises all of the hardware and software required for it to perform its indication function. The sensor indicator unit 114 may provide an audible, visual, haptic, or other indication that is perceived by a user of the oral care implement 100. For example, in one embodiment the sensor indicator unit 114 may provide different sounds to indicate different results of the monitoring of the oral care parameter being performed by the first sensor unit 113 and/or to indicate different passages of time as described in greater detail below. In another embodiment, the sensor indicator unit 114 may provide different visual signals, such as illuminating different colored lights, illuminating lights in different patterns, illuminating different symbols, or the like to indicate different results of the monitoring of the oral care parameter being performed by the first sensor unit 113 and/or to indicate different passages of time as described in greater detail below. In still other embodiments, the sensor indicator unit 114 may provide different patterns of vibration that are felt by the user of the oral care implement 100 to indicate different results of the monitoring of the oral care parameter being performed by the first sensor unit 113 and/or to indicate different passages of time as described in greater detail below.

As noted above, in one particular embodiment the first sensor unit 113 is a plaque detection unit. In such an embodiment, the sensor indicator unit 114 may generate a first user perceptible stimulus while plaque is being detected on an oral surface by the first sensor unit 113, a second user perceptible stimulus when the oral surface is determined to be free of plaque by the first sensor unit 113, a third user perceptible stimulus when the first sensor unit 113 is covered (such as by toothpaste slurry or the like) and therefore unable to perform its monitoring function, and a fourth user perceptible stimulus when the first sensor unit 113 is not covered but is still unable to view the teeth to perform its monitoring function (for example, the oral care implement 100 may be held at an angle that prevents the first sensor unit 113 from seeing the teeth and performing its function, or the first sensor unit 113 may be removed from the oral cavity). In other embodiments, the user perceptible stimulus generated by the sensor indicator unit 114 may be correlated with the passage of time during an oral care session either alone or in combination with data acquired by the first sensor unit. This will be described in greater detail below with particular reference to FIG. 25.

Each of the first, second, third, and fourth user perceptible stimuli could be different sounds or patterns of sound, different vibration patterns, or different colors or patterns of light that can be perceived by the user. In one exemplified embodiment which will be described in greater detail below, the first, second, third and fourth user perceptible stimuli may be the illumination of light either in a different color, a different pattern, or some combination thereof. Thus, in one particular embodiment the first user perceptible stimulus may be light of a first color and the second user perceptible stimulus may be light of a second color. In embodiments that include it, the third user perceptible stimulus may be light of a third color, and the fourth user perceptible stimulus may be light of a fourth color. In other embodiments, the fourth user perceptible stimulus may be light of the third color, but in a different illumination pattern than the third user perceptible stimulus. Thus, for example, the third user perceptible stimulus may be the illumination of the third color of light in a solid and non-blinking/flashing pattern, whereas the fourth user perceptible stimulus may be the illumination of the third color of light in a blinking/flashing pattern. Of course, these are merely examples and there are many different possibilities for the different user perceptible stimuli. In some embodiments, combinations of audible, tactile, and visual stimuli may be used. Thus, one or more of the user perceptible stimuli may be the emission of a sound, one or more of the user perceptible stimuli may be the emission of light, and/or one or more of the user perceptible stimuli may be a vibration or other sensation (such as a heating sensation, a cooling sensation, or the like) that is felt by the user.

The structure and components of the sensor indicator unit 114 is dictated, at least in part, by the particular stimuli being generated by the sensor indicator unit 114. Thus, for example, if the user perceptible stimuli is a sound, the sensor indicator unit 114 may comprise a speaker, if the user perceptible stimuli is tactile such as a vibration, the sensor indicator unit 114 may comprise a vibration generator, and if the user perceptible stimuli is visual, the sensor indicator unit 114 may comprise one or more light sources such as light emitting diodes or any other type of light emitter. A specific embodiment of the sensor indicator unit 114 that comprises one or more light sources will be described in greater detail below.

The control circuit 110 also comprises the second sensor unit 117. In the exemplified embodiment the second sensor unit 117 is integrated into the oral care implement 100. However, as noted above the second sensor unit 117 may be integrated into the electronic device 500 in other embodiments. In still other embodiments, the second sensor unit 117 may not be integrated into either of the oral care implement 100 or the electronic device 500.

In the exemplified embodiment, the second sensor unit 117 is configured to determine an orientation and/or position of the oral care implement 100 within the user's oral cavity during the oral care session. Thus, as the user is cleaning his/her oral cavity with the oral care implement 100, the second sensor unit 117 is monitoring and/or determining the orientation and/or position of the oral care implement 100 relative to the teeth of the oral cavity. Additional details for the second sensor unit 117 in accordance with one embodiment of the present invention are described in U.S. Pat. No. 10,349,733, issued Jul. 16, 2019, the entirety of which is incorporated herein by reference. However, the second sensor unit 117 may take on other forms in other embodiments. For example, the second sensor unit 117 may comprise an optical sensor that determines the location of the oral care implement 100 in the oral cavity based on which tooth is within the frame of the optical sensor (for example, camera). The second sensor unit 117 may comprise accelerometers, gyroscopes, magnetometers, and other hardware for achieving its position detection function. In still other embodiments, the second sensor unit 117 may comprise any of one or more of optical sensors, accelerometers, gyroscopes, magnetometers, GPS, facial recognition, or the like.

As noted above, in the exemplified embodiment the memory unit 127 of the control circuit 110 is integrated into the oral care implement 100. However, the memory unit 127 could alternatively be integrated into the electronic device 500. Furthermore, there could be multiple memory units, with at least one in each of the oral care implement 100 and the electronic device 500. The memory unit 127 may be any type of memory device that is configured to store data either before or after such data has been processed. Thus, the memory unit 127 may comprise ROM, PROM, RAM, SRAM, DRAM, SIMM, DIMM, or any other type of device commonly used for storage of data and/or other information.

In the exemplified embodiment, the first wireless communication unit 120 is integrated into the oral care implement 100 to facilitate communication between the oral care implement 100 and the electronic device 500 and/or other electronic devices. In the exemplified embodiment, the first wireless communication unit 120 is configured for Bluetooth communication, but other types of wireless communication devices and other types of wireless communication may be used instead in other embodiments.

The oral care implement 100 further comprises the motion inducing unit 119, which may form a part of the control circuit 110 or may be in operable cooperation with the control circuit 110 without forming a part of the control circuit 110. In the exemplified embodiment, the motion inducing unit 119 is operably coupled to the processor 111 so that the processor 111 can instruct the motion inducing unit 119 on its operation. The motion inducing unit 119 may comprise a motor such as an eccentric motor, or any other vibration generating device. The motion inducing unit 119 is configured to impart motion to the oral care tool 310 of the oral care implement 100 along which the cleaning elements 311 such as bristles are positioned. As a result, when the motion inducing unit 119 is activated, the cleaning elements 311 vibrate to improve the cleaning effect that they perform. The motion inducing unit 119 may perform other functions as well, such as possibly playing a role in the generation of the user perceptible stimulus.

The timer unit 115 and the time indicator unit 116 are both integrated into the oral care implement 100 in the exemplified embodiment. The timer unit 115 and the time indicator unit 116 are operably coupled to the processor 111. The timer unit 115 and the time indicator unit 116 may be coupled directly to each other in some embodiments, but their coupling to the processor 111 is sufficient in the exemplified embodiment to ensure that data obtained by the timer unit 115 is transmitted to the time indicator unit 116 as described further herein. Each of the timer unit 115 and the time indicator unit 116 comprises the necessary hardware, software, and processors to facilitate their operation.

The timer unit 115 may comprise any device that is configured to track time during performance of the oral care session. Thus, as the user cleans his/her oral cavity during the oral care session, the timer unit 115 will keep track of the amount of time that has elapsed during the oral care session. Thus, the timer unit 115 may comprise a clock, a timer, a count-up timer, a count-down timer, a stopwatch, or the like. The timer unit 115 may comprise its own processor, or it may be coupled to the processor 111, or both. The memory unit 127 may be configured to store data relating to the time tracked during the performance of the oral care session. Thus, as the oral care session takes place, the timer unit 115 tracks the time that has elapsed and data relating to the time tracked by the timer unit 115 is transmitted to (either directly or indirectly by way of the processor 111) and stored in the memory unit 127.

The timer unit 115 may comprise a zone timer and a session timer, the details of which will be provided below. Briefly, the session timer may track the time that has elapsed during an oral care session from start of the session to completion of the session. The zone timer may track time in which a user performs the oral care session in a particular zone without the oral cavity. Thus, the oral cavity may be broken into a plurality of zones, and the zone timer may track time spent in each zone so that it can operate in conjunction with the sensor indicator unit 114 to prompt or otherwise signal a user to move from zone to zone so that the user does not spend insufficient time or too much time in a single zone. Details of this usage and operation will be provided below, mostly with reference to FIG. 25. In some embodiments, the timer unit 115 may only track real brushing time. Thus, in such embodiments if a user holds the device outside of the mouth the counters of the timer will not increment.

The time indicator unit 116 is operably coupled to the timer unit 115, in the exemplified embodiment due to both of those units being coupled to the processor 111. The time indicator unit 116 is configured to inform the user, during the oral care session, of the amount of time that has elapsed during the performance of the oral care session. Thus, the time indicator unit 116 preferably generates a user perceptible signal at various time intervals to indicate to the user the amount of time that has elapsed during an oral care session. This may be desirable because it is generally agreed that people should brush their teeth for approximately two minutes. Thus, providing the user with an indication of the amount of time that has elapsed during the oral care session can be beneficial to ensuring that the user continues the oral care session for the entire time period, whether that be two minutes, three minutes, or some other pre-determined time period.

The time indicator unit 116 may comprise a speaker or the like if the user perceptible signal that it generates is a sound, a vibration generator or the like if the user perceptible signal that it generates is haptic or tactile, or one or more lights if the user perceptible signal that is generates is visual. In the exemplified embodiment, as will be described in greater detail below, the time indicator unit 116 comprises a plurality of light emitters such as light emitting diodes or other light sources so that the time indicator unit 116 can provide a visual indication of the amount of time that has elapsed during the oral care session to the user. The time indicator unit 116 may provide an indication to the user of the elapsed time in predetermined intervals, such as at every one-fourth of the total desired time period. Thus, for example, if the desired time for the oral care session is two minutes, then the time indicator unit 116 may generate an indication (by illuminating one or more light sources) every 30 seconds. Specific details about the time indicator unit 116 in accordance with one particular embodiment of the present invention will be provided below during the discussion of one particular structural embodiment of the oral care implement 100.

The actuator unit 130 comprises the mode selection unit 118 and the power unit 131. The actuator unit 130 is integrated into the oral care implement in the exemplified embodiment. In some embodiments, some or all of the actuator unit 130 may be located in the electronic device 500 instead of the oral care implement 100. Thus, for example, the mode selection unit 18 may be integrated into the electronic device 500 while the power unit 131 is integrated into the oral care implement 100, or both of the mode selection unit 118 and the power unit 131 may be integrated into the electronic device.

In the exemplified embodiment, the mode selection unit 118 comprises a switch 128 (see FIG. 1) that is located on the oral care implement 100. Specifically, in the exemplified embodiment the mode selection switch 128 is a button-type switch provided on the front surface of the handle 200 of the oral care implement 100. Furthermore, in the exemplified embodiment the power unit 131 comprises a power switch 129 located on the front surface of the handle 200. The mode selection unit 118 and the power unit 131 are operably coupled to the processor 111. Actuation of the power switch 129 may cause the processor 111 to power the oral care implement 100 on, which may include powering all of the components of the control circuit 110 that are integrated into the oral care implement 100 as shown in FIG. 2 and described herein.

Actuation of the mode selection switch 128 may change a mode of operation of the oral care implement 100. Specifically, in the exemplified embodiment, the mode selection unit 118 is configured to allow a user to select between a normal mode and a quiet mode. Thus, in some embodiments, upon actuating the power switch 129, the oral care implement 100 will be configured to operate in the normal mode. If, after the power switch 129 has been actuated, the mode selection switch 128 is then actuated, the mode will be altered from the normal mode to the quiet mode. Of course, in other embodiments the oral care implement 100 may initially be powered on in the quiet mode such that actuation of the mode selection switch 128 will alter it into the normal mode. In some embodiments, a user must actuate the mode selection switch 128 within a predetermined period of time after actuation of the power switch 129 in order to change the mode from the normal mode to the quiet mode, and/or vice versa. The predetermined period of time may be five seconds in one embodiment, or ten seconds in another embodiment, or fifteen seconds in another embodiment, or twenty seconds in another embodiment, or thirty seconds in another embodiment.

Still referring to FIGS. 1 and 2, in the exemplified embodiment the control circuit 110 comprises the following components integrated into or otherwise coupled to the electronic device 500: the processor 121, the power source 125, the toothbrush app 123 comprising the mapping unit 124, and the wireless communication unit 122. The electronic device 500 may also comprise a display unit 126 that is operably coupled to the control circuit 110.

The power source 125 may be any type of device typically used to power an electronic device such as a smart phone. For example, the power source 125 may be one or more batteries in some embodiments, although other power sources could be used in other embodiments. The wireless communication unit 122 is configured for operable communication with the wireless communication unit 120 of the oral care implement 100. Thus, information gathered or processed by the oral care implement 100 can be transmitted to the electronic device 500 for various processing and/or storage and/or display on the display unit 126. The display unit 126 may be any type of display commonly used on an electronic device, such as a liquid-crystal display (LCD) or the like. The display unit 126 may allow for user interaction such as being a touch screen in some embodiments.

The toothbrush app 123 may be a mobile application that is stored on a memory device (not shown) of the electronic device 500. Specifically, the toothbrush app 123 may be an app that can be downloaded from an app store. The toothbrush app 123 may be a computer program or software application designed to run on an electronic device such as the electronic device 500. Due to the operable communication between the electronic device 500 and the oral care implement 100, data or information gathered or acquired from the sensors in the oral care implement 100 can be transmitted to the electronic device 500 and used by the toothbrush app 123 to provide the user with the data in a manner that is valuable to that particular user for improving his/her cleaning performance or the like.

The toothbrush app 123 may comprise the mapping unit 124, which may contain all of the necessary software, hardware, code, or the like to enable it to function and operate as described herein. In some embodiments, the mapping unit 124 may be configured to generate an oral cavity map in which locations of the physiological condition in the user's oral cavity are identified based on data obtained from the first and second sensor units 113, 114. Thus, as the first sensor unit 113 monitors the oral care parameter during performance of an oral care session and the second sensor unit 114 determines an orientation and/or position of the oral care implement 100 within the user's oral cavity during the oral care session, this information may be transmitted to the mapping unit 124 of the electronic device 500.

Figure 3:
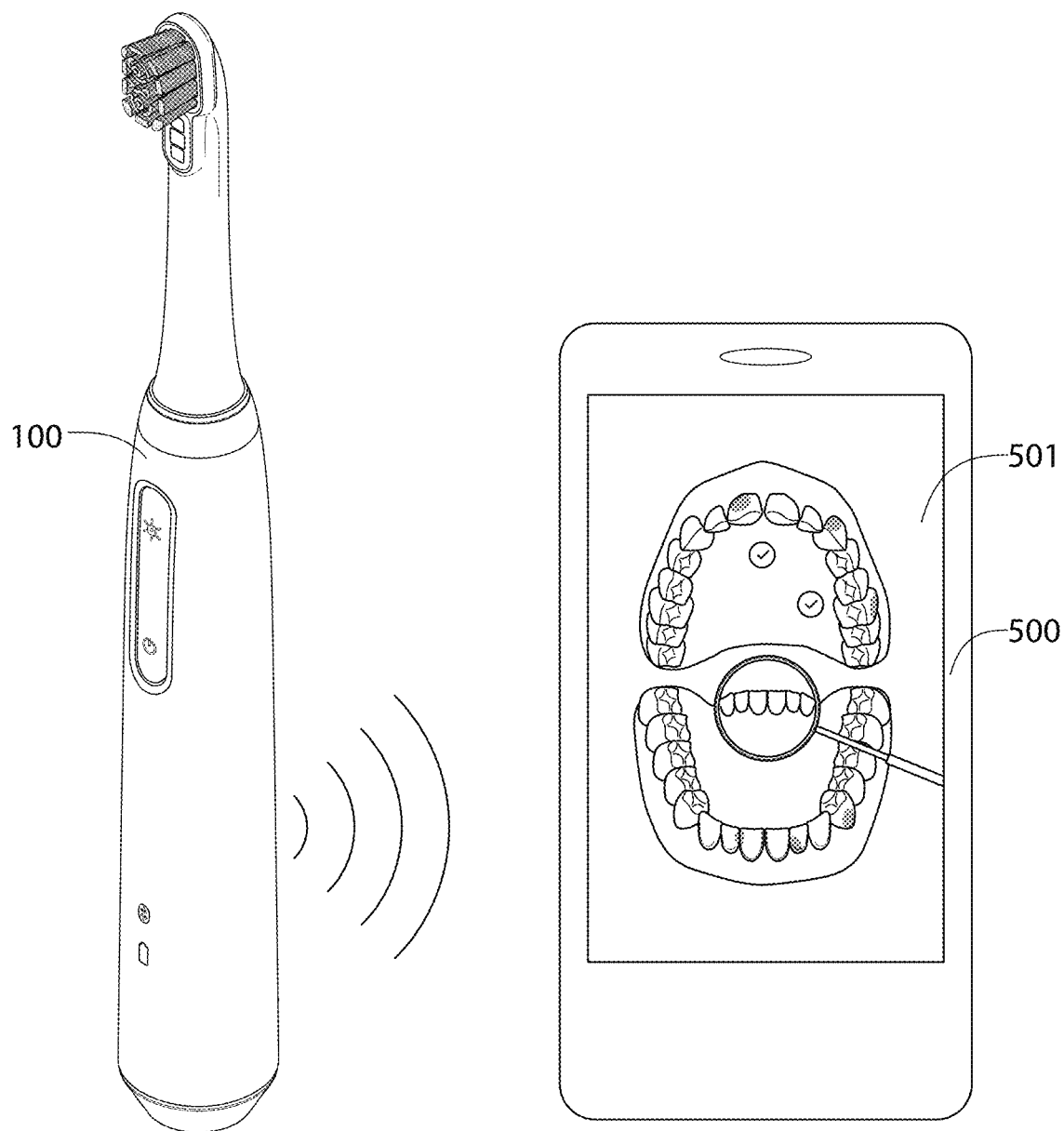
FIG. 3 illustrates the oral care system of FIG. 1 with an oral cavity map depicted on a display of the electronic device.

Specifically, due to the communication between the oral care implement 100 and the electronic device 500 (in the exemplified embodiment, wireless communication by way of the wireless communication units 120, 122), the information obtained by the first and second sensor units 113, 114 can be sent to the electronic device 500 either pre or post processing. Specifically, the information gathered by the first and second sensors 113, 114 may be processed by the processor 111 prior to being sent to the electronic device 500, or the information may be sent to the electronic device 500 for processing by the processor 121. At any rate, either way the information eventually is transmitted to the mapping unit 124, which can generate the oral cavity map to provide a visual indication to the user of the locations in the oral cavity that have the physiological oral condition (for example, show where plaque was found on the teeth). An exemplary oral cavity map is shown on a display 501 of the electronic device 500 in FIG. 3. Thus, in some embodiments the data relating to the monitored oral care parameter that is stored in the memory unit 127 includes data acquired from both the first sensor unit 113 and the second sensor unit 114. In some embodiments, the data relating to the monitored oral care parameter also comprises the oral cavity map, which can also be stored in the memory unit 127.

Referring to FIG. 4, the change in operation depending on whether the oral care implement 100 is in normal mode or quiet mode will be described. As mentioned above, the mode selection unit 118 of the actuator unit 130 allows a user to decide whether he/she wants the oral care implement 100 to operate in the normal mode or the quiet mode. The oral care implement 100 may operate in the normal mode unless the user actuates the mode selection switch 128 within a specific time period after powering the oral care implement 100 on, in which case the oral care implement 100 will operate in the quiet mode.

Upon activating the power switch 129, the oral care implement 100 will power on and will be in the normal mode. Alternatively, the user may select the normal mode rather than having the oral care implement 100 automatically operate in the normal mode. For example, upon powering the oral care implement 100 on the user may be provided with a choice to operate in the normal mode or the quiet mode. When in the normal mode, upon the user beginning to clean the oral cavity with the oral care implement 100 for an oral care session, the first sensor unit 113 will be active during the oral care session. This means that the first sensor unit 113 will be monitoring the oral care parameter during the oral care session. In accordance with the exemplified embodiment, the first sensor unit 113 will be monitoring the existence or lack thereof of plaque on the oral surfaces or teeth of the oral cavity.

Furthermore, in the normal mode the sensor indicator unit 114 will be active during the oral care session. Thus, in the normal mode the sensor indicator unit 114 will generate user perceptible stimuli during the oral care session upon the first sensor unit 113 detecting that the monitored oral care parameter meets certain criteria. With regard to one exemplified embodiment, the sensor indicator unit 114 will generate user perceptible stimuli (light, sound, vibration, or the like) upon the first sensor unit 113 detecting a certain amount of plaque on the teeth. More specifically, in one particular embodiment the sensor indicator unit 114 will generate light of one or more colors to provide an indication to the user that the first sensor unit 113 has detected an amount of plaque that exceeds a certain threshold. As noted, the sensor indicator unit 114 may be provide on or otherwise integrated into the oral care implement 100. Thus, the sensor indicator unit 114 may generate light which is emitted out of or from the oral care implement 100 itself, such that it can be seen by a user while he/she is performing the oral care session. Additional details about the sensor indicator unit 114 and its location and operation will be described below in accordance with a structural embodiment of the oral care implement.

In the normal mode, the data relating to the monitored oral care parameter is also stored in the memory unit 127 during the oral care session. Thus, in the normal mode, the first sensor unit 113 is active during the oral care session to monitor an oral care parameter, data relating to the oral care parameter being monitored by the first sensor unit 113 is stored in the memory unit 127 (this may occur during or after the oral care session depending on whether the data is transmitted to the memory unit 127 in real-time of after the oral care session is complete), and the sensor indicator unit 114 is active.

As noted above, a user may desire to operate the oral care implement 100 in the quiet mode instead of in the normal mode. This may be achieved by pressing the mode selection switch 128 after the oral care implement 100 has been powered on and before beginning the oral care session, or in other ways as described herein and/or easily understood by persons skilled in the art. The quiet mode is very similar to the normal mode, except with regard to the operation of the sensor indicator unit 114. Thus, in the quiet mode, the first sensor unit 113 is active and is monitoring the oral care parameter during the oral care session and the data relating to the monitored oral care parameter is stored in the memory unit 127 either during or after the oral care session. However, the difference between the normal mode and the quiet mode is that in the quiet mode the sensor indicator unit 114 is inactive during the oral care session. Thus, the sensor indicator unit 114 does not generate any user perceptible stimuli during the oral care session when the oral care implement 100 is in the quiet mode.

Thus, in both the normal mode and the quiet mode the first sensor unit 113 is still monitoring the oral care parameter (e.g., the existence or lack thereof of plaque on the teeth) and this data is still being transmitted to and stored by the memory unit 127 (which may be located in the oral care implement 100 as shown in FIG. 2, in the electronic device 500 as mentioned above, or elsewhere). This data may also still be displayed on the display unit 126 of the electronic device 500 either during or after the oral care session via the toothbrush app 123 and/or the mapping unit 124. However, whereas in the normal mode an indication of the detection of the monitored oral care parameter is provided to the user via user perceptible stimuli (lights, sounds, vibrations, etc.) on the oral care implement 100, this does not occur in the quiet mode. Thus, for example, where the sensor indicator unit 114 comprises one or more lights that are illuminated on the oral care implement 100, these lights are inactive (i.e., not operating) when the oral care implement 100 is in the quiet mode. Thus, the quiet mode inactivates the sensor indicator unit 114 on the oral care implement 100 while all other features and electronic components of are active.

As also shown in FIG. 4, the motion inducing unit 119 may be active in both the normal mode and the quiet mode. Thus, the motion inducing unit 119 may impart vibrational motion to the cleaning elements in both the normal and quiet modes. In that sense, the quiet mode does not make the oral care implement 100 operate without making sound, because the motion inducing unit 119 may produce sounds in some embodiments. Rather, the quiet mode turns off or deactivates the feature on the oral care implement 100 that provides immediate, real-time feedback to the user through the generation of user perceptible stimuli in the form of sound, vibration, and/or lights. The wireless communication unit 120 in the oral care implement 100 and the wireless communication unit 122 in the electronic device 500 may be active in both the normal and quiet modes so that data/ information monitored and otherwise gathered by the oral care implement 100 and its sensors can be transmitted to the electronic device 500 regardless of whether the oral care implement 100 is operating in the normal mode or the quiet mode.

As noted above, the timer unit 115 and the time indicator unit 116 track time elapsed during performance of an oral care session and informs the user of the time that has elapsed (through activation of lights, sounds, and/or vibrations). In the exemplified embodiment, the timer unit 115 and the time indicator unit 116 are both active in the normal mode and in the quiet mode. However, in other embodiments, when the oral care implement 100 is operating in the quiet mode the timer unit 115 may be active to track time while the time indicator unit 116 may be inactive so that user perceptible indication of the elapsed time is not provided to the user on the oral care implement 100 during the oral care session.

Figure 5:
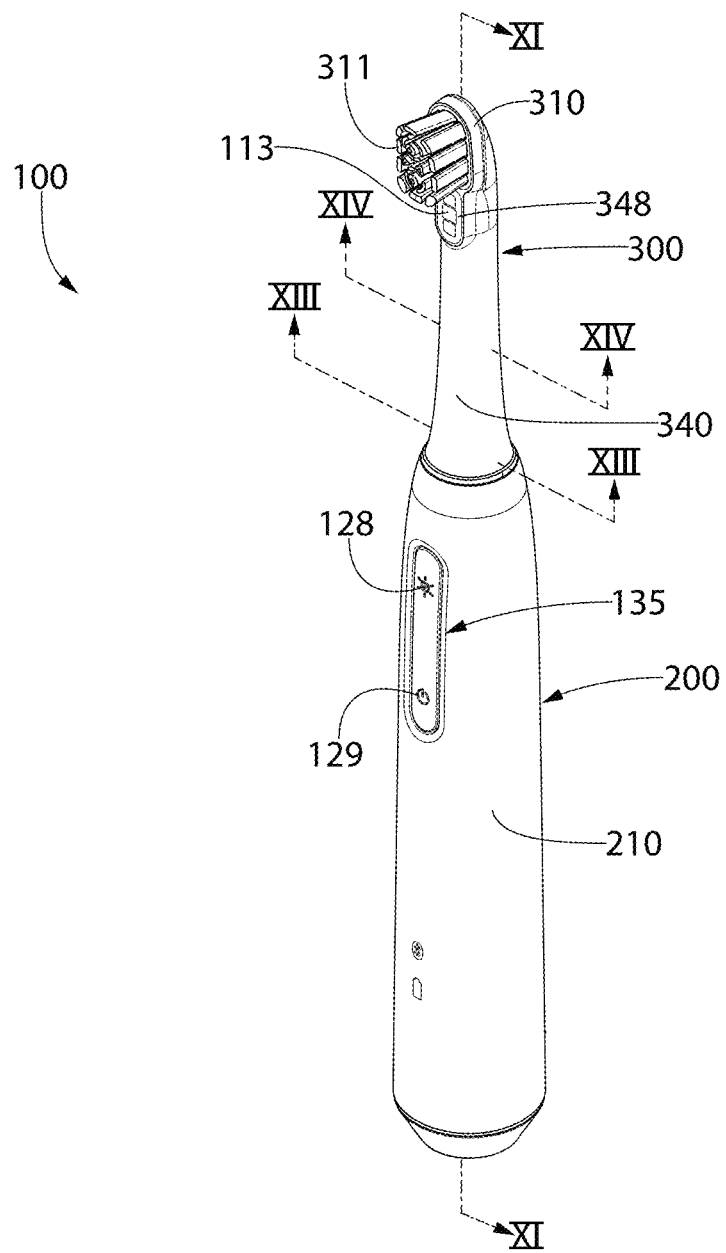
FIG. 5 is a perspective view of the oral care implement of the oral care system of FIG. 1 in accordance with an embodiment of the present invention.
Figure 7:
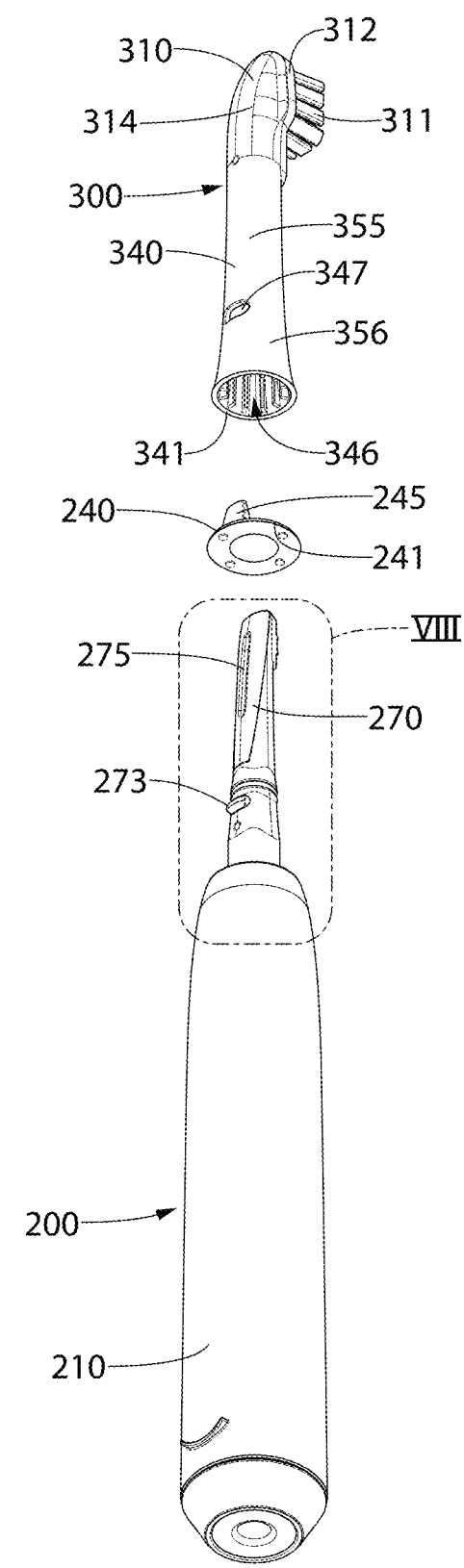
FIG. 7 is a rear perspective view of FIG. 6.

Referring to FIGS. 5-7, the oral care implement 100 will be described in greater detail. Specifically, FIGS. 5-7 and the remaining figures in this document illustrate various portions of the oral care implement 100. This will allow for a more detailed description of some of the components mentioned above, as well as a detailed description of some new features not previously mentioned above. FIGS. 5-7 and the remaining figures depict one exemplary embodiment of the oral care implement 100. However, it should be appreciated that the invention is not to be limited to the structural details of the oral care implement 100 described below in all embodiments.

As mentioned above, the oral care implement 100 generally comprises a handle 200 and an oral care refill head 300. The handle 200 and the oral care refill head 300 may be formed of plastic such as polypropylene in some embodiments, although this is not required in all embodiments and other materials may be used including wood, metal, or the like. In the exemplified embodiment, the oral care refill head 300 is detachable from the handle 200 so that the oral care refill head 300 can be replaced when the cleaning elements 311 become worn or for other reasons (such as to use an oral care refill head 300 with cleaning elements formed from a different material or having a different pattern to achieve a particular cleaning function). Thus, the oral care refill head 300 may be alterable between a first state in which the oral care refill head 300 is separated from the handle 200 (see, for example, FIGS. 6 and 7) and a second state in which the oral care refill head 300 is coupled to the handle 200 (see, for example, FIG. 5).

Figure 9:
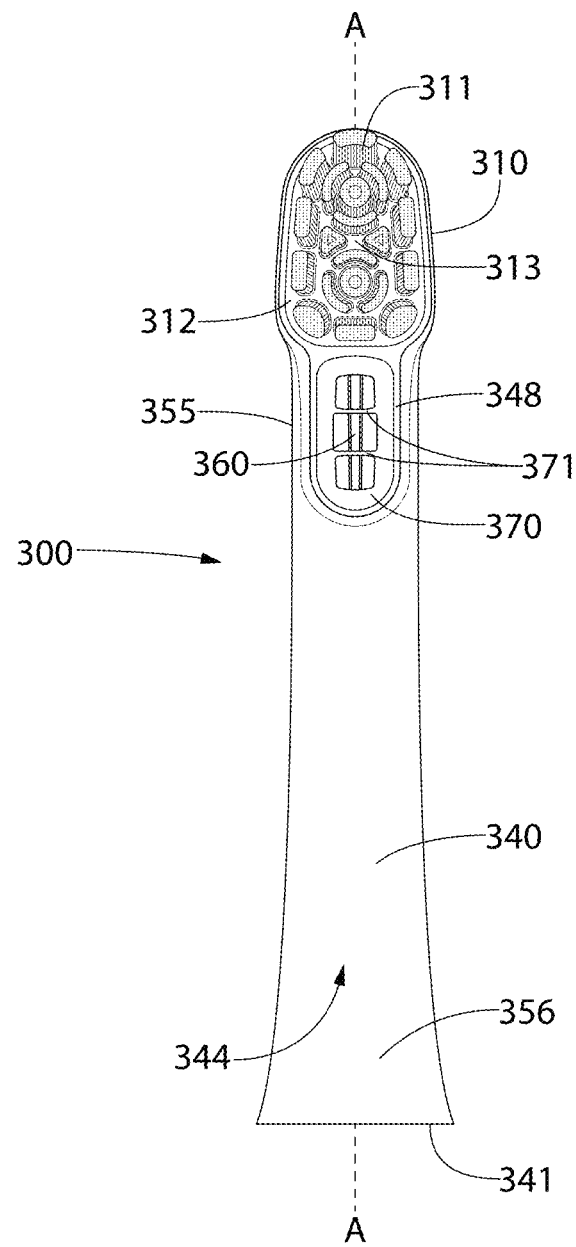
FIG. 9 is a front view of the oral care refill head of the oral care implement of FIG. 5.
Figure 10:
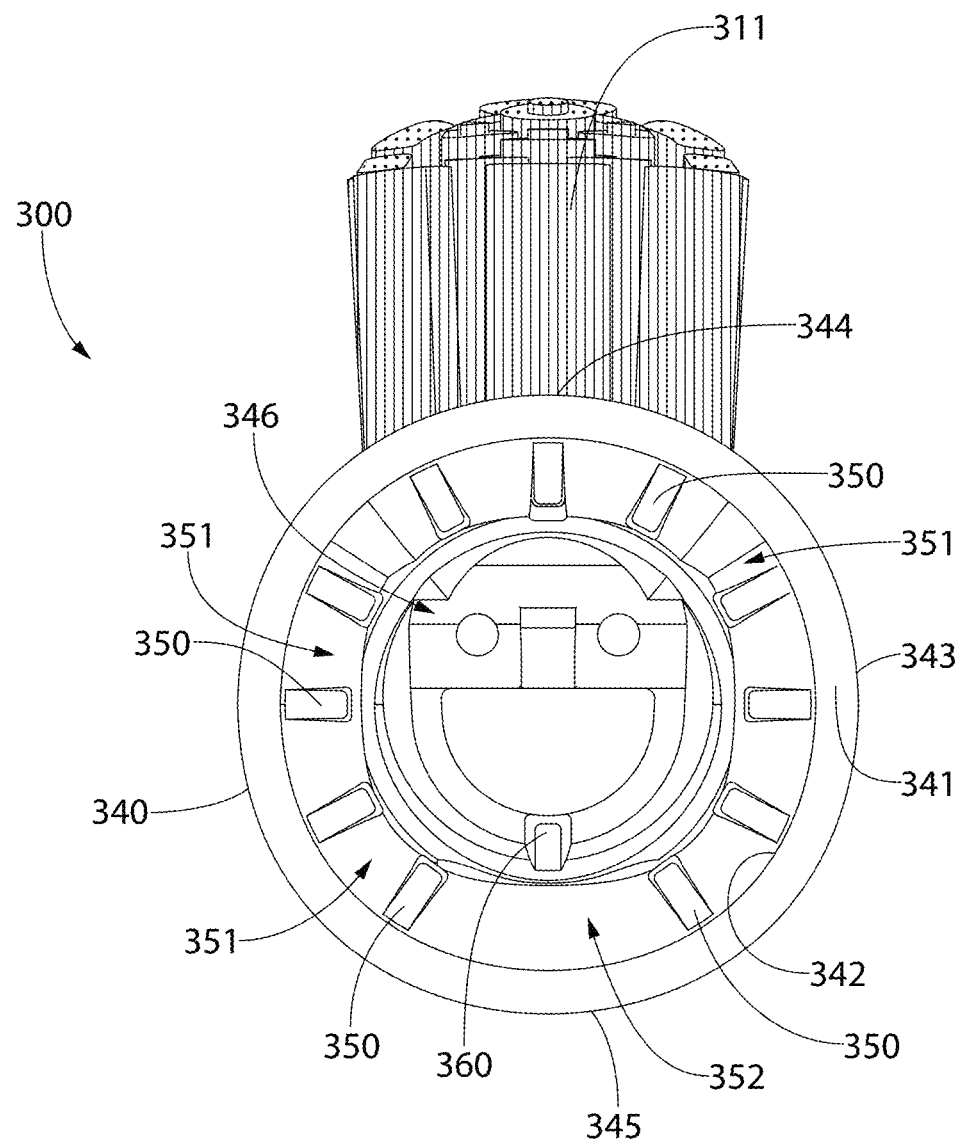
FIG. 10 is a bottom view of the oral care refill head of FIG. 9.

Referring to FIGS. 7, 9, and 10, the oral care refill head 300 will be described in greater detail. The oral care refill head 300 comprises the oral care tool 310 (or oral care treatment portion) and a sleeve portion 340. Furthermore, there are a plurality of tooth cleaning elements 311 (bristles and/or lamella formed of nylon, rubber, or the like as mentioned above) on the oral care tool 310 that are used for treatment and/or cleaning of a user's oral cavity, and particularly the teeth, gums, and tongue thereof.

The oral care tool 310 of the oral care refill head 300 comprises a head body 312 having a front surface 313 and a rear surface 314. The plurality of tooth cleaning elements 311 extend from the front surface 313 of the head body 312. The sleeve portion 340 of the oral care refill head 300 is connected to the head body 312 of the oral care tool 310 and extends from the head body 312 to a proximal end 341. A proximal portion of the sleeve portion 340 flares outwardly in a direction towards the proximal end 341. The sleeve portion 340 has an inner surface 342 and an outer surface 343, with the outer surface 343 comprising a front surface 344 that faces the same direction as the front surface 313 of the head body 312 and a rear surface 345 opposite the front surface 344.

The inner surface 342 of the sleeve portion 340 defines a sleeve cavity 346 having a cavity axis A-A. The sleeve portion 340 is configured to receive the stem 270 of the handle 200 when the oral care refill head 300 is coupled to the handle 200 as described herein. The sleeve portion 340 of the oral care refill head 300 comprises a sleeve snap element 347 that is configured to mate with an engagement feature of the handle 200 for purposes of coupling the oral care refill head 300 to the handle 200. In the exemplified embodiment, the sleeve snap element 347 is a locking aperture located on the rear surface 345 of the sleeve portion 340 of the oral care refill head 300. The locking aperture extends through the thickness of the sleeve portion 340 and provides a passageway from the exterior environment into the sleeve cavity 346. In the exemplified embodiment, the locking aperture of the sleeve snap element 347 is in the shape of an oval that is elongated in a direction that is transverse to the cavity axis A-A. The locking aperture of the sleeve snap element 347 is spaced axially above the proximal end 341 of the sleeve portion 340. Although the sleeve snap element 347 of the oral care refill head 300 is described herein as being a locking aperture, the invention is not to be so limited in all embodiments and in other embodiments the sleeve snap element 347 may be a protuberance, a tab, or the like that is configured to mate with a feature on the handle 200 for purposes of locking the oral care refill head 300 in the second state whereby it is coupled to the handle 200.

The sleeve portion 340 of the oral care refill head 300 also comprises a window aperture 348 formed into the front surface 344 of the sleeve portion 340. The window aperture 348 extends through the thickness of the sleeve portion 340 and provides a passageway from the exterior environment to the sleeve cavity 346. Furthermore, the window aperture 348 is located adjacent to and just below the cleaning elements 311. The window aperture 348 also has an oval shape, although the window aperture 348 is elongated in a direction that is parallel to the cavity axis A-A. The window aperture 348 is immediately adjacent to and below the cleaning elements 311 in the exemplified embodiment. As will be described in more detail below, the window aperture 348 is aligned with the first sensor unit 113, which is located on the stem 270 of the handle 200, when the oral care refill head 300 is coupled to the handle 270 so that the first sensor unit 113 is exposed through the window aperture 348. This enables the first sensor unit 113 to have visual access to the oral cavity through the window aperture 348 during use of the oral care implement 100 so that the first sensor unit 113 can perform its monitoring function as described herein.

Furthermore, the oral care refill head 300 comprises a transparent window 370 overlying and/or covering the window aperture 348. The transparent window 370 is transparent to ensure that the first sensor unit 113 has an unimpeded view through the transparent window 370 and into the oral cavity during an oral care session. In the exemplified embodiment, the window 370 comprises at least one divider wall 371 dividing the transparent window 370 into a plurality of sections. In the exemplified embodiment, each of the sections of the transparent window 370 is aligned with a different component (i.e., an optical sensor 140, a light source 141, and a receiver 142 described below with reference to FIGS. 5-8B) of the first sensor unit 113. The optical sensor 140 may be a camera in one embodiment. The dividers help to ensure that stray light does not saturate the optical sensor to ensure proper functioning. However, in other embodiments the dividers may be omitted so long as it can be ensured that such stray light will not cause a malfunction or improper operation of the device. In various different embodiments, the window aperture 348 may be an open aperture, the window aperture 348 may be covered by the transparent window 370 so that the first sensor unit 113 can be protected against damage from fluids, and in other embodiments the window aperture 348 may not be an aperture at all, but may instead comprise a portion of the sleeve 340 that is formed from a transparent material.

Still referring to FIGS. 7, 9, and 10, additional features of the oral care refill head 300 will be described. In the exemplified embodiment, the oral care refill head 300 comprises a plurality of ribs 350 that extend from the inner surface 342 of the sleeve portion 340 in a circumferentially spaced apart manner. In the exemplified embodiment, each of the plurality of ribs 350 extends from a position that is spaced from but adjacent to the proximal end 341 in a direction towards the head body 312. However, the plurality of ribs 350 do not extend the full length of the sleeve 340. Rather, the plurality of ribs 350 terminate at (or near/adjacent to) the aperture of the sleeve snap element 347 in the exemplified embodiment. More specifically, the ribs extend to distal ends that are transversely aligned with the locking feature 347. The ribs 350 may be located further from the proximal end 341 of the sleeve portion 340 than the locking feature 347 in other embodiments.

The spaces between the plurality of ribs 350 form a plurality of channels 351 such that each channel 351 is bounded by two of the ribs 350 that are adjacent to one another. Thus, each of the channels 351 extends from the proximal end 341 to the location at which the ribs 350 terminate within the sleeve cavity 346. Each of the plurality of channels 351 has a width measured as a minimum linear distance between the two adjacent ribs 350 between which that particular channel 351 is defined.

An alignment channel 352 of the plurality of channels 351, which functions to properly align the oral care refill head 300 relative to the handle 200 as described in greater detail below, has a greater width than a remainder of the plurality of channels 351. In the exemplified embodiment, all of the channels 351 have the same width except for the alignment channel 352, which has a greater width. However, the invention is not to be so limited in all embodiments and the channels 351 could all have varying widths, with the alignment channel 352 being the channel 351 with the greatest width. In the exemplified embodiment, there is only one of the alignment channels 352, which ensures that the oral care refill head 300 can only be coupled to the handle 200 in one relative orientation. If more than one orientation is permissible, it would be possible for there to be multiple of the alignment channels 352. The alignment channel 352 may be referred to herein as a second engagement feature because it mates or interacts with an engagement feature of the handle 200 as described in more detail below.

Moreover, the oral care refill head 300 comprises an elongated alignment rib 360 that extends from the inner surface 342 of the sleeve portion 340. Thus, like the ribs 350, the elongated alignment rib 360 extends into the sleeve cavity 346. In the exemplified embodiment, the elongated alignment rib 360 is located between the sleeve lock element 347 (e.g., locking aperture) and the oral care tool or oral treatment portion 310 of the oral care refill head 300. Thus, the elongated alignment rib 360 is located closer to the oral treatment portion 310 than each of the plurality of ribs 350 and the sleeve snap element or locking aperture 347.

As best seen in FIG. 9, a portion of the elongated alignment rib 360 is aligned with the window aperture 348 formed into the front surface 344 of the sleeve portion 340 of the oral care refill head 300. As a result, when the oral care refill head 300 is in the first state such that it is detached from the handle 200, the elongated alignment rib 360 is visible through the window aperture 348. The reason for this that when the oral care refill head 300 is in the second state such that it is attached to the handle 200, the elongated alignment rib 360 presses against the stem 270 of the handle 200 to force the first sensor unit 113 to extend into or near/adjacent to the window aperture 348. This ensures that the first sensor unit 113 is properly positioned within the window aperture 348 during use of the oral care implement 100 so that it can perform its monitoring function. This will be described in greater detail below during a discussion of the structural relationship between the oral care refill head 300 and the handle 200 when in the assembled state.

The sleeve portion 340 comprises a distal portion 355 adjacent to the oral treatment portion 310 and a proximal portion 356 adjacent to the proximal edge 341. In the exemplified embodiment, the plurality of ribs 350 and the sleeve snap element 347 are located along the proximal portion 356 and the elongated alignment rib 360 and the window aperture 348 are located along the distal portion 355.

Referring to FIGS. 5-8B, the handle 200 will be described in greater detail. The handle 200 comprises a gripping portion 210 having a distal end 211, an engagement component 240 that may be detachably coupled to the distal end 211 of the gripping portion 210, and a stem 270 that protrudes from the engagement component 240. The engagement component 240 and the stem 270 both play a role in the attachment of the oral care refill head 300 to the handle 200 in the exemplified embodiment, as will be described in greater detail below. The gripping portion 210 of the handle 200 is the portion of the oral care implement 100 that is configured to be gripped by a user during use of the oral care implement 100 in performing its cleaning function. A user-operated actuator 135 that comprises the mode selection switch 128 and the power switch 129, are located on the gripping portion 210 of the handle 200 in the exemplified embodiment.

As noted above, the first sensor unit 113 is integrated into the oral care implement 100. More specifically, in the exemplified embodiment the first sensor unit 113 is located on a distal portion 271 of the stem 270. The first sensor unit 113 may comprise an imaging device (e.g., a camera) 140, a light source 141, and a receiver 142 in some embodiments, although this is not required in all embodiments. The first sensor unit 113 may comprise any components necessary for it to function as required. In the exemplified embodiment, the first sensor unit 113 is a plaque detection unit, so it comprises the components needed to detect plaque on the teeth. The imaging device 140 (alone or along with the light source 141) is configured to take images of the teeth and the receiver 142 is configured to receive the images and transmit them to the processor 111 for processing to determine whether or not plaque is present on the teeth. As shown in FIG. 5, when the oral care refill head 300 it coupled to the handle 200, the first sensor unit 113 is aligned with and extends into (or immediately adjacent to) the window aperture 348 of the oral care refill head 300.

The user-operated actuator 135 is operably coupled to the actuator unit 130 and comprises the power switch 129 and the mode selection switch 12. The user-operated actuator 135 is located on the gripping portion 210 of the handle 200. Thus, a user gripping the handle 200 can readily and easily actuate the power switch 129 to power the oral care implement 100 on and off and the mode selection switch 128 to alter the operation of the oral care implement 100 between the normal mode and the quiet mode. There is also a status indicator 212 on the gripping portion 210 of the handle 200. The status indicator 212 comprises a connectivity indicator 212a and a power source indicator 212b. The connectivity indicator 212a may light up when the oral care implement 100 is operably connected to the electronic device 500 (such as via Bluetooth or the like as described herein above). The power source indicator 212b may light up in different colors or different levels (i.e., heights), or the like to indicate an amount of charge remaining in the power source 112 (see FIG. 2) of the oral care implement 100.

In the exemplified embodiment, the engagement component 240 is a separate and distinct component relative to the gripping portion 210 and the stem 270 of the handle 200. The engagement component 240 may be snap-fit connected to the distal end 211 of the gripping portion 210 in some embodiments. In other embodiments, the engagement component 240 may be coupled to the distal end 211 of the gripping portion 210 in other ways, including using fasteners, adhesive, mechanical engagement, twist and lock, notch and protuberance, or the like. In some embodiments, it may be desirable for the engagement component 240 to be detachable from the gripping portion 210 so that it can be replaced with a different engagement component 240, with the engagement component 240 having a particular structure designed to interact with the oral care refill head 300. Thus, as mentioned in more detail below, by changing the engagement component 240, one can force a change in the structure of the oral care refill head 300 that is able to be coupled to the handle 200. Thus, instead of having to replace the entire handle 200 to modify the engagement mechanism, by having a separate engagement component 240 the engagement mechanism (or a portion thereof) that mates with the oral care refill head 300 can be changed without having to replace the entire handle 200.

In the exemplified embodiment, the engagement component 240 comprises a plate portion 241 having a top surface 242 and a bottom surface 243 opposite the top surface 242. The plate portion 241 further comprises an aperture 244 extending from the top surface 242 to the bottom surface 243. Thus, in the exemplified embodiment the engagement component 240 has a ring-like annular shape like that of a doughnut. The top and bottom surfaces 242, 243 are flat and planar and parallel to one another in the exemplified embodiment. However, this is not required in all embodiments and the top and/or bottom surfaces 242, 243 could have some contour in other embodiments. When the oral care implement 100 is assembled, the bottom surface 243 of the plate portion 241 faces and is in contact with the distal end 211 of the gripping portion 210 and the top surface 242 of the plate portion 241 faces and is in contact with the proximal end 341 of the oral care refill head 300.

The engagement component 240 also comprises a first engagement feature 245 that is configured to mate with the second engagement feature (i.e., the alignment channel 352) of the oral care refill head 300 when the oral care refill head 300 is attached to the handle 200. More specifically, the first engagement feature 245 of the engagement component 240 is configured to mate with the second engagement feature 352 of the oral care refill head 300 to at least one of: (1) position the oral care refill head 300 in an operational alignment; and (2) lock the oral care refill head 300 to the handle 200. Because the circuitry for the oral care implement 100 is located in the handle 200, in some embodiments the oral care refill head 300 must be positioned in a particular orientation relative to the handle 200 for the circuitry to operate properly because part of the operation is dependent upon a position sensor and determining the location of the oral care refill head 300 relative to the oral cavity. Furthermore, a particular orientation between the oral care refill head 300 and the handle 200 may be needed for the imaging sensor (i.e., optical sensor or camera 140) to function properly. Thus, by "operational alignment" it is meant that the oral care refill head 300 is aligned with the handle 200 in such a manner that the control circuit 110 is able to operate properly in accordance with the disclosure set forth herein. Thus, the first and second engagement features 245, 352 may properly align the oral care refill head 300 with the handle 200 and/or the first and second engagement features 245, 352 may lock the oral care refill head 300 to the handle 200, or both. In the exemplified embodiment, as discussed further herein, the first and second engagement features 245, 252 mate or otherwise interact to align the oral care refill head 300 with the handle 200.

In the exemplified embodiment, the first engagement feature 245 of the engagement component 240 is an alignment protrusion 246 that extends from the top surface 242 of the plate portion 241 of the engagement component 240. The plate portion 240 has an inner surface 247 that faces/defines the aperture 244 and an opposite outer surface 248. In the exemplified embodiment, the alignment protrusion 246 is spaced radially inward of the outer surface 248 and is adjacent to the aperture 244. Thus, the alignment protrusion 246 is located closer to the inner surface 247 than to the outer surface 248 of the plate portion 240. More specifically, in the exemplified embodiment at least a portion of the alignment protrusion 246 is flush with the inner surface 247 of the plate portion 241. This ensures that there is sufficient space on the top surface 242 of the plate portion 240 between the alignment protrusion 246 and the outer surface 248 for engagement with the proximal end 341 of the sleeve portion 240 of the oral care refill head 300.

Figure 8A:
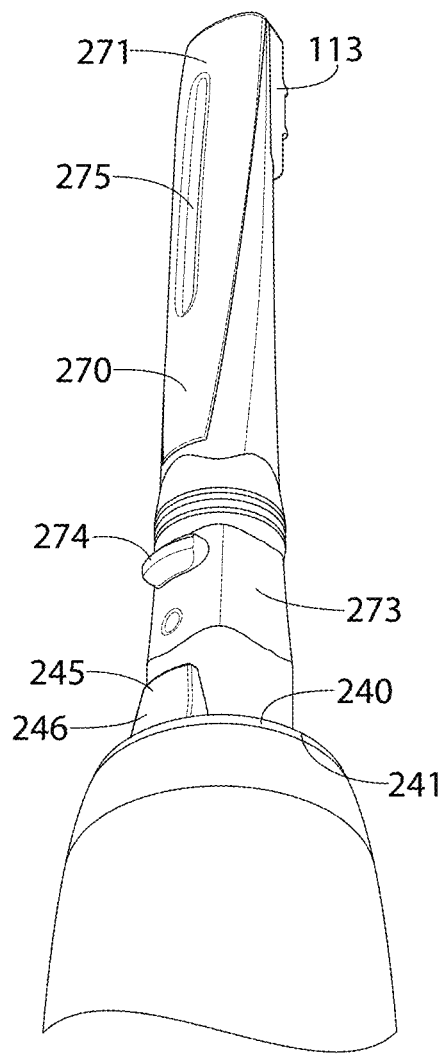
FIG. 8A is a close-up view of area VIII of FIG. 7.
Figure 8B:
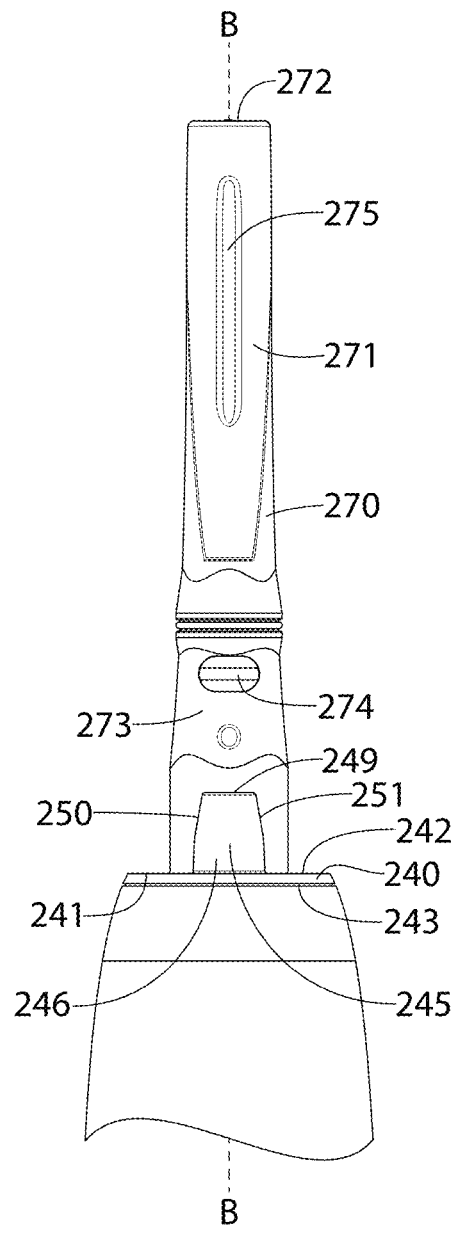
FIG. 8B is a rear view of area VIII of FIG. 7.

As best seen in FIG. 8B, the alignment protrusion 246 extends from the top surface 242 of the plate portion 240 to a distal end 249. The alignment protrusion 246 comprises a first sidewall 250 extending from the top surface 242 of the plate portion 240 to the distal end 249 and a second sidewall 251 extending from the top surface 242 of the plate portion 240 to the distal end 249. In the exemplified embodiment, each of the first and second sidewalls 250, 251 comprise smooth outer surfaces that are free of any notches or protrusions. Furthermore, in the exemplified embodiment the alignment protrusion 246 tapers along at least a portion of its length as it extends from the top surface 242 of the plate portion 241 to the distal end 249. Stated another way, a width of the alignment protrusion 246 measured between the first and second sidewalls 249, 250 decreases along at least a portion of the length of the alignment protrusion 246 as the distance from the top surface 242 of the plate portion 241 increases. This tapering of the alignment protrusion 246 allows the alignment protrusion 246 to more easily enter into the alignment channel 352 of the oral care refill head 350 during the coupling of the oral care refill head 300 to the handle 200.

When the handle 200 is assembled, the stem 270 of the handle 200 extends through the aperture 244 of the plate portion 241 of the engagement component 240 so that the top surface 242 of the plate portion 241 of the engagement component 240 forms an annular shoulder that circumscribes the stem 270. The stem 270 extends from the top surface 242 of the plate portion 240 to a distal end 272. The stem 270 comprises the distal portion 271 mentioned previously and a proximal portion 273, with the proximal portion 273 being adjacent to the engagement component 240. The stem 270 extends along a stem axis B-B.

The stem 270 of the handle 200 comprises a stem snap element 274 that is configured to interact with the sleeve snap element 347 to securely couple (or lock) the oral care refill head 300 to the handle 200. In the exemplified embodiment, the stem snap element 274 is a protrusion that extends from the stem 270. More specifically, in the exemplified embodiment the stem snap element 274 is a protrusion having an oval shape that is elongated in a direction transverse to the stem axis B-B. Thus, the stem snap element 274 and the sleeve snap element 347 have a similar shape to enable them to matingly engage one another to lock the oral care refill head 300 to the handle 200. Specifically, when the oral care refill head 300 is coupled to the handle 200, the stem snap element 274 snaps into the aperture of the sleeve snap element 347 to securely couple the oral care refill head 300 to the handle 200 by a snap-fit interlock. The stem snap element 274 nests within the aperture of the sleeve snap element 347 when the oral care refill head 300 is coupled to the handle 200. The stem snap element 274 is located along the proximal portion 273 of the stem 270 in the exemplified embodiment. Furthermore, the stem snap element 274 is circumferentially aligned with the alignment protrusion 246 of the first engagement feature 245 of the engagement component 240 in the exemplified embodiment as best shown in FIG. 8B.

The stem 270 of the handle 200 further comprises an elongated alignment notch 275 located along the distal portion 272 of the stem 270. The elongated alignment notch 275 is elongated in a direction that is parallel to the stem axis B-B. The elongated alignment notch 275 is configured to receive and/or mate with the elongated alignment rib 360 of the oral care refill head 300 when the oral care refill head 300 is coupled to the handle 200. As mentioned above, this interaction presses the distal portion 271 of the stem 270 forward within the sleeve cavity 346 towards the front surface 344 of the sleeve portion 340 so that the first sensor unit 113 extends into and/or is positioned adjacent to the window aperture 348 (or the transparent window 370 covering the window aperture 348) of the oral care refill head 300. As will be described further below, the elongated alignment rib 360 of the oral care refill head 300 nests within the elongated alignment notch 275 on the stem 270 when the oral care refill head 300 is coupled to the handle 200.

In the exemplified embodiment, the elongated alignment notch 275 is circumferentially aligned with the stem snap element 274 and with the alignment protrusion 246. Thus, a reference plane on which the stem axis B-B lies intersects each of the elongated alignment notch 275, the stem snap element 274, and the alignment protrusion 246. Moreover, the elongated alignment notch 275 is located on an opposite surface of the stem 270 relative to the first sensor unit 113. This is needed so that the interaction between the elongated rib 360 of the oral care refill head 300 and the alignment notch 275 presses the first sensor unit 113 forward so that it is positioned adjacent to the window aperture 348 and transparent window 370 of the oral care refill head 300.

Figure 11:
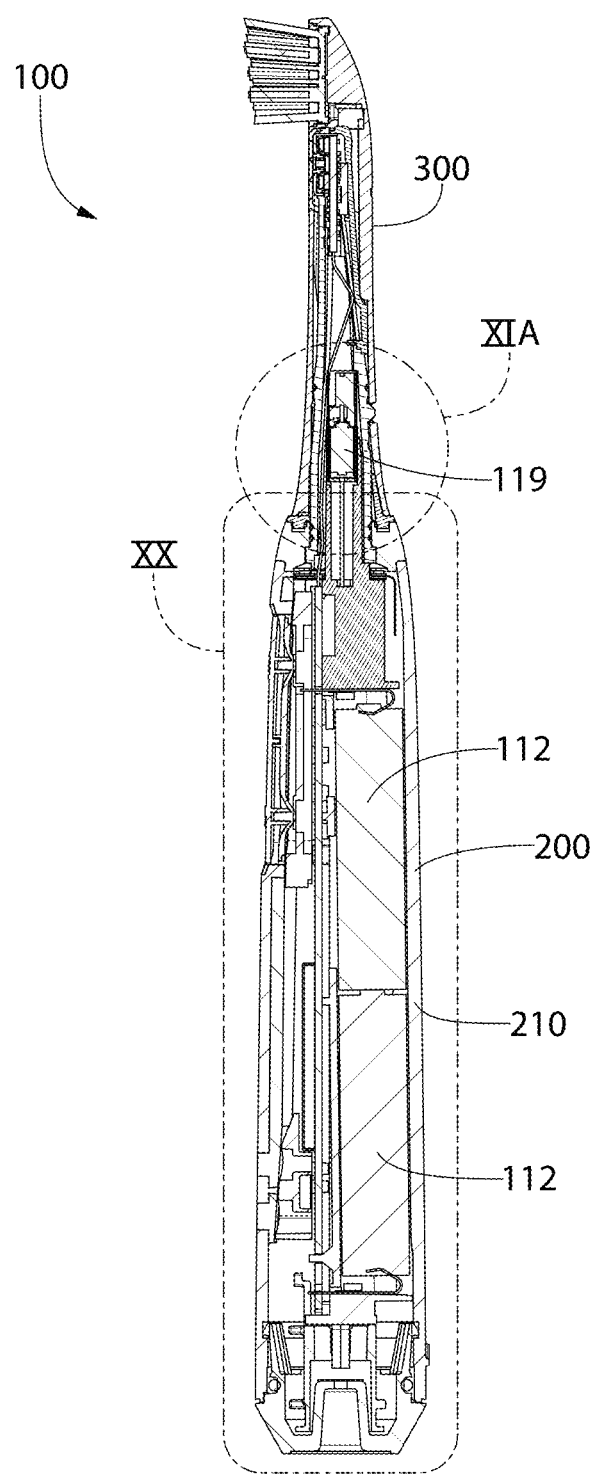
FIG. 11 is a cross-sectional view taken along line XI-XI of FIG. 5.
Figure 11A:
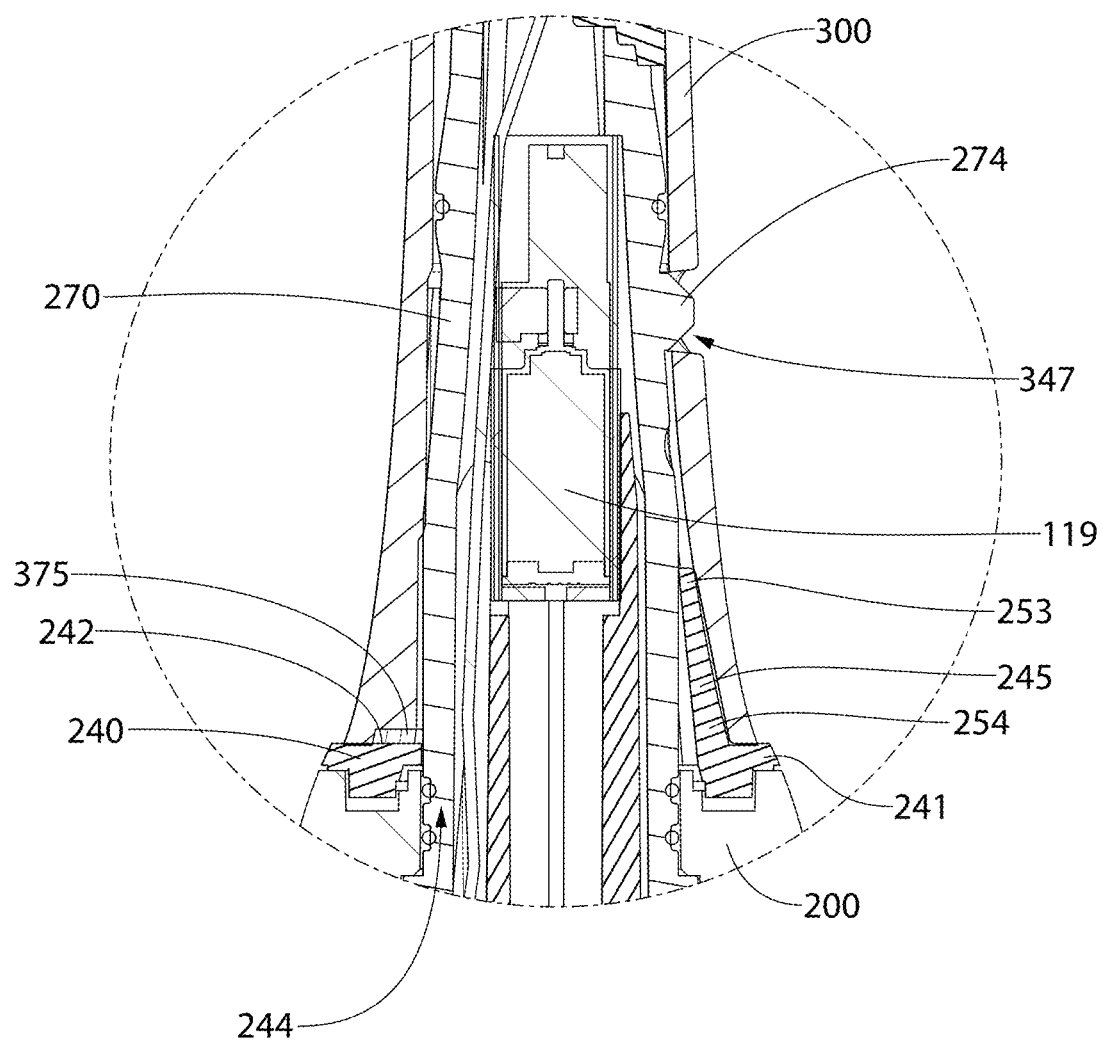
FIG. 11A is a close-up view of area XIA of FIG. 11.

Referring to FIGS. 11 and 11A, the interaction between the oral care refill head 300 and the handle 200 will be further described when the oral care refill head 300 is coupled to the handle 200. As noted above, the stem snap element 274 (which is a protuberance in the exemplified embodiment) protrudes into and through the sleeve snap element 347 (which is an aperture in the exemplified embodiment). As can be seen, the stem snap element 274 is chamfered on its upper and lower surfaces to render it easier to snap the stem snap element 274 into and out of the sleeve snap element 347. Although in the exemplified embodiment the stem snap element 274 comprises a locking protuberance and the sleeve snap element 347 comprises a locking aperture 347, the invention is not to be so limited in all embodiments. Thus, in some alternative embodiments the stem snap element 274 may comprise an aperture and the sleeve snap element 347 may comprise a protuberance. Furthermore, other mating features may be used as the stem and sleeve snap elements 274, 347 while still achieving the function of locking the oral care refill head 300 to the handle 200 for use of the oral care implement 100.

Furthermore, as best seen in these views, the first engagement feature 245 (specifically, the alignment protrusion 246) extends from the top surface 242 of the plate portion 241 at an oblique angle in a direction towards the stem 270 and towards the aperture 244. Thus, the alignment protrusion 246 comprises a first portion 253 that comprises the distal end 249 and a second portion 254 that is located closer to the top surface 242 of the plate portion 241. The second portion 254 of the alignment protrusion 246 is spaced apart from the stem 270 and the first portion 253 of the alignment protrusion 246 is in contact with the stem 270.

In addition to the mechanical features that facilitate the coupling of the oral care refill head 300 to the handle 200, FIGS. 11 and 11A also depict some of the electronic components. Thus, for example, the power source 112 is shown in the gripping portion 210 of the handle 200. The motion inducing unit 119 is illustrated as a motor and eccentric combination that is positioned within the stem 270 of the handle 200. Many of the other components of the control circuit 110, while shown in FIGS. 11 and 11A, will not be described at this time but will instead of described later on in this document.

Figure 12A:
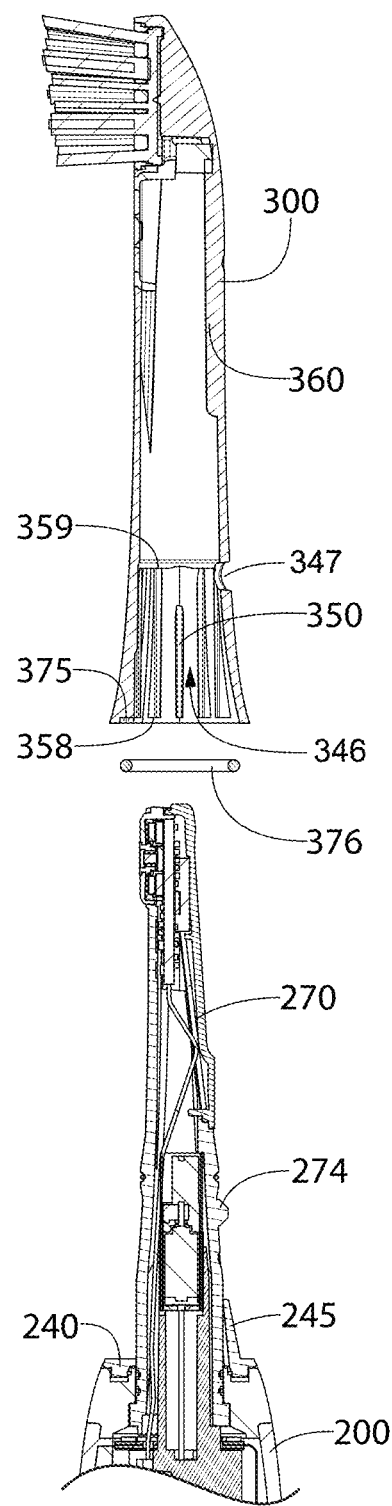
FIGS. 12A-12C are cross-sectional views of the oral care implement of FIG. 5 that sequentially illustrate the process of coupling the oral care refill head to the handle.

Furthermore, referring to FIGS. 11A and 12A, the oral care refill head 300 comprises an annular recess 375 located just above the proximal end 341 of the sleeve portion 340. The plurality of ribs 350 may not extend into the annular recess 375, as best shown in FIG. 12A. Specifically, the plurality of ribs 350 may extend from a proximal end 358 to a distal end 359, with the proximal end 358 being spaced apart from the proximal edge 341 of the sleeve portion 340. Thus, the plurality of ribs 350 may extend from just above the annular recess 375 to their terminal ends. The annular recess 375 may therefore be located in the space between the proximal end 358 of the ribs 350 and the proximal edge 341 of the sleeve portion 340 of the oral care refill head 300.

In some embodiments, the annular recess 375 is configured to receive a gasket 376 therein. The gasket 376 may be formed of rubber or other resilient materials as commonly used for gaskets or O-rings or the like. When assembled, the gasket 376 is positioned within the annular recess 375 such that the ribs 350 extend upwardly towards the oral care tool 310 from the gasket 376. Thus, in the assembled oral care implement (see FIG. 12C), the gasket 376 is sandwiched between the proximal ends 358 of the plurality of ribs 350 and the top surface 242 of the plate portion 241 of the engagement component 240. The gasket 376 assists in preventing water and toothpaste slurry from entering into the spaces between the oral care refill head 300 and the stem 270 of the handle 200 during use, which can be important to prevent the components of the first sensor unit 113 from becoming obfuscated or blocked. Specifically, if a toothpaste slurry is able to enter into the space between the oral care refill head 300 and the stem 270, it may be able to flow up to the distal end of the stem 270 where the components of the first sensor unit 113 (e.g., the optical sensor 140, the light source 141, and/or the receiver 142) are located, thereby blocking the visual pathway from the first sensor unit 113 to the oral surfaces.

Figure 12B:
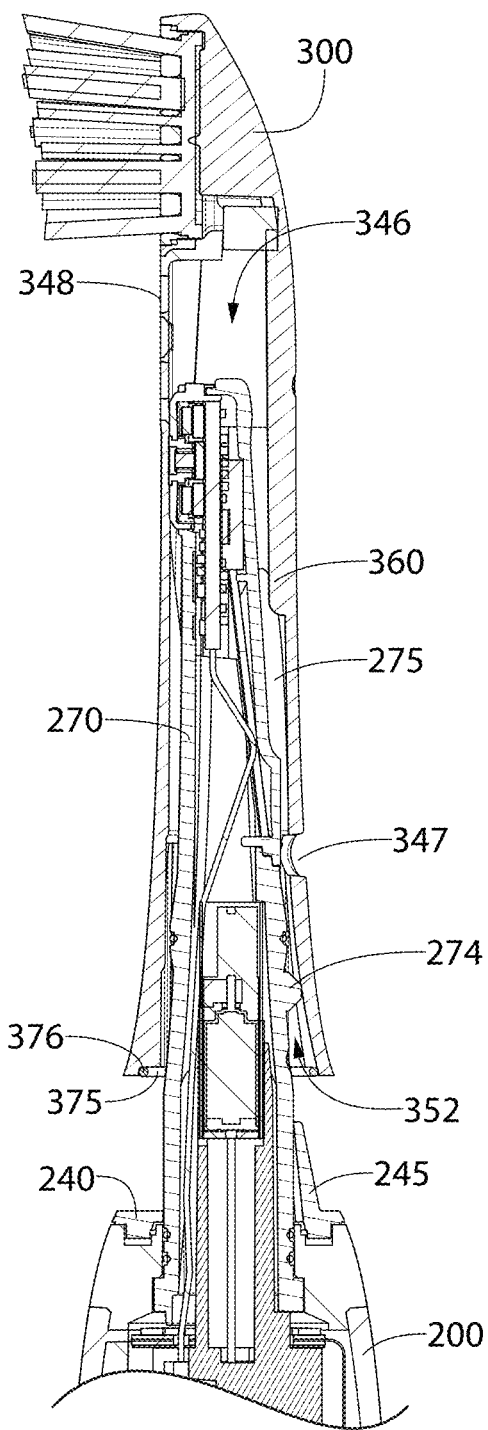
Figure 12C:
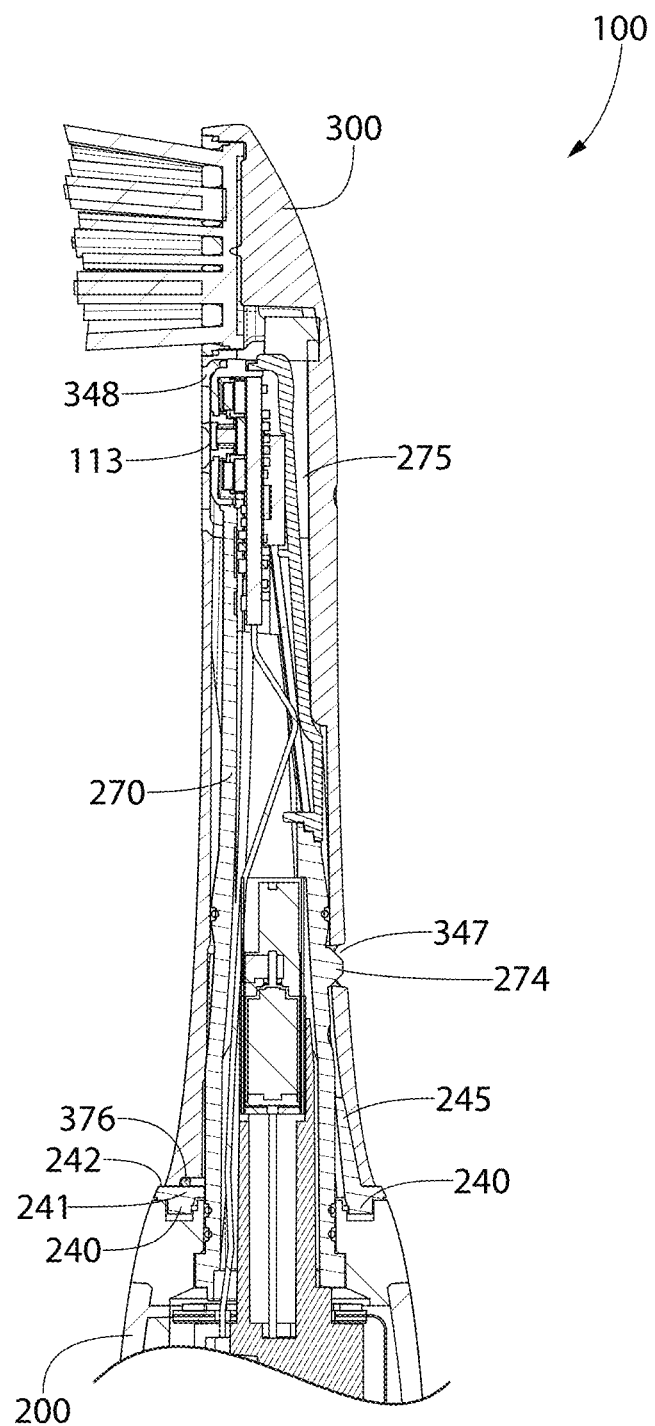

Referring to FIGS. 12A-12C sequentially, the process of coupling the oral care refill head 300 to the handle 200 is illustrated. FIG. 12A illustrate the oral care refill head 300 completely separated from the handle 200, but aligned for purposes of coupling those two components together. As shown in FIG. 12B, to couple the oral care refill head 300 to the handle 200, the oral care refill head 300 is moved towards the handle 200 so that the stem 270 of the handle 200 enters into the sleeve cavity 346 of the oral care refill head 300. The oral care refill head 300 continues to be moved axially relative to the handle 200 until the stem snap element 274 snaps into the sleeve snap element 346. However, before this occurs, the alignment protrusion 245 of the engagement component 240 will bump against the plurality of ribs 350 of the oral care refill head 300 until the alignment protrusion 245 is aligned with the alignment channel 352. Thus, if upon first placing the stem 270 into the sleeve cavity 346 the oral care refill head 300 and the handle 200 are not properly aligned, the user may need to rotate the oral care refill head 300 relative to the handle 200 until the alignment protrusion 245 is aligned with the alignment channel 352. Once this alignment is achieved, the oral care refill head 300 will be able to be pressed onto the handle 200 until a click is heard as the stem snap element 274 snap-interlocks with the sleeve snap element 346.

Furthermore, as seen in FIGS. 12B and 12C, as the oral care refill head 300 is pressed onto the handle 200, the elongated rib 360 of the oral care refill head 300 slides into and within the elongated alignment notch 275 of the stem 270. The elongated alignment rib 360 presses against the stem 270 and forces the first sensor unit 113 to be positioned adjacent to the window aperture 348 or transparent window 370 of the oral care refill head 300.

As mentioned previously, because the first engagement feature 245 (i.e., the alignment protuberance 246 in the exemplified embodiment) is formed as part of an engagement component 240 that is separate from and non-integral with the gripping portion 210 or the stem 270 of the handle 200 (i.e., the engagement component 240 is a distinct component from the gripping portion 210 and the stem 270), the first engagement feature 245 can be exchanged for another as desired, perhaps by the manufacturer or perhaps by the end-user. The first engagement feature 245 is specifically designed to mate with the oral care refill head 300. Thus, an oral care refill head 300 having different structures may not permit coupling with the handle 200, particularly due to the configuration of the first engagement feature 245. Thus, swapping out the engagement component 240 for another will enable coupling of the handle 200 to different oral care refill heads 300.

Figure 13:
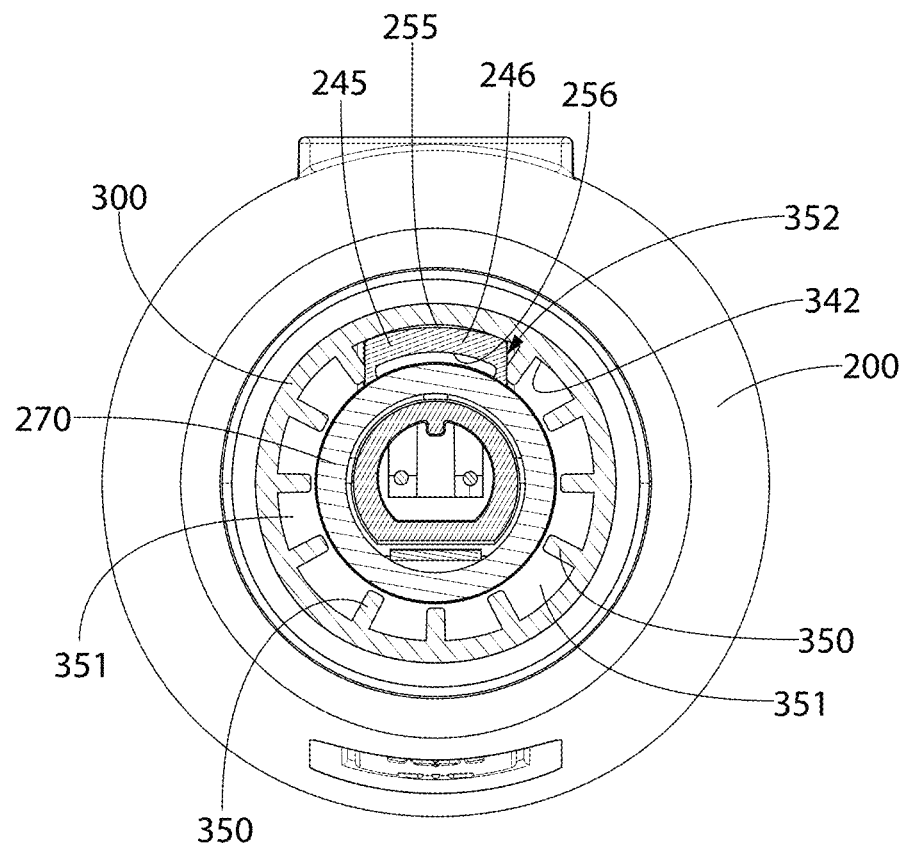
FIG. 13 is a cross-sectional view taken along line XIII-XIII of FIG. 5.

FIG. 13 once again shows the mating interaction between the first engagement feature 245 (i.e., the alignment protuberance 246) and the second engagement feature (i.e., the alignment channel 352). As can be seen in this view, the alignment protrusion 246 cannot fit within any of the plurality of channels 351 except for the alignment channel 352. Thus, the alignment protrusion 246 is prohibited from entering into and nesting within any of the plurality of channels 351 other than the alignment channel 352 due to their respective widths as described above. The alignment protuberance 246 nests within the alignment channel 352 and is sandwiched between the stem 270 of the handle 200 and the inner surface 342 of the oral care refill head 300.

As seen in this view, the alignment protuberance 246 has a rounded or slightly arcuate outer surface 255 so that it confirms to the shape of the inner surface 342 of the oral care refill head 300. Furthermore, at least a portion of an inner surface 256 of the alignment protuberance 246 is spaced apart from the stem 270. Specifically, in this embodiment the alignment protuberance 246 has two arms protruding from opposing sides of a main body. The two arms terminate in distal ends that contact the stem 270, but the inner surface 256 of the alignment protuberance 246 is spaced from the stem 270 in the region between the two arms.

Figure 14:
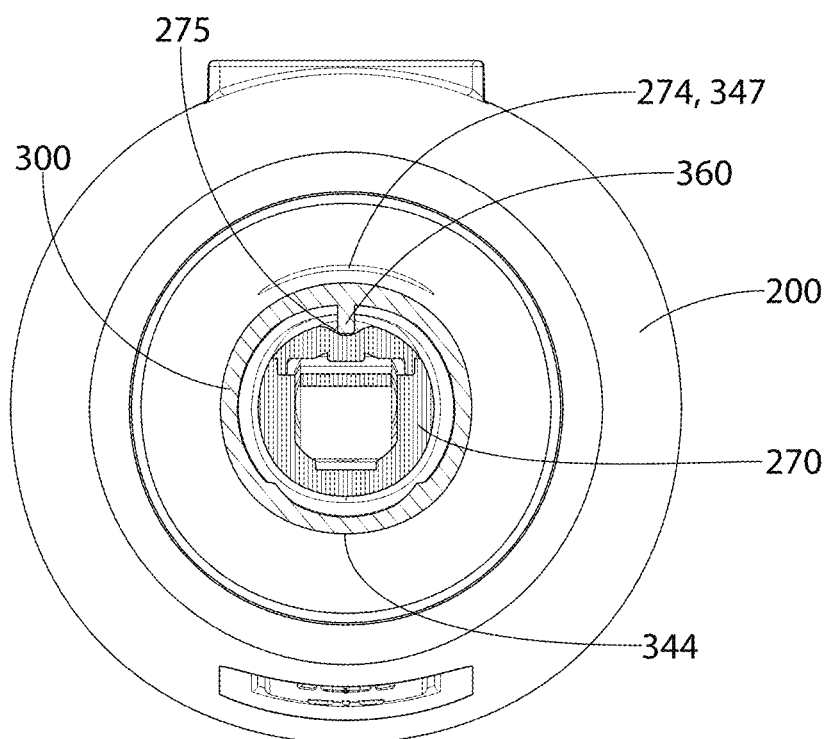
FIG. 14 is a cross-sectional view taken along line XIV-XIV of FIG. 5.

FIG. 14 shows the mating between the elongated alignment rib 360 of the oral care refill head 300 and the elongated alignment notch 275 on the stem 270 of the handle 200. As can be seen, the elongated alignment rib 360 nests within the elongated alignment notch 275. Furthermore, the elongated alignment rib 360 is in direct contact with the floor of the elongated alignment notch 275, which causes the elongated alignment rib 360 to press the stem 270 towards the front surface 344 of the sleeve portion 340 of the oral care refill head 300 so that the first sensor unit 113 is exposed via the window aperture 348 as has been described herein.

Figure 15:
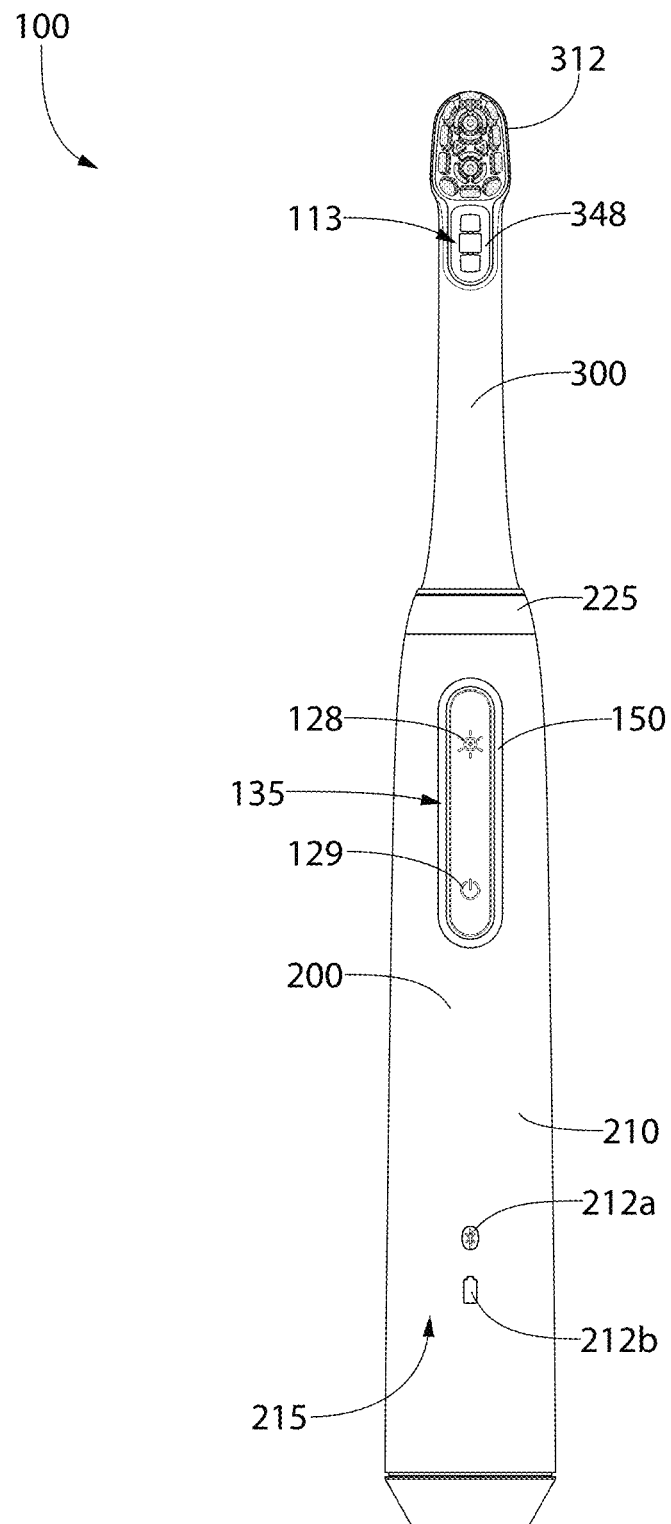
FIG. 15 is a front view of the oral care implement of FIG. 1.

Referring to FIG. 15, the oral care implement 100 is illustrated in a front view with the oral care refill head 300 coupled to the handle 200. As noted previously, the first sensor unit 113 positioned on the stem 270 of the handle 200 is exposed through the window aperture 348 of the oral care refill head 300. As a result, the first sensor unit 113 can monitor and/or take images or gather data related to one or more physiological conditions of the oral cavity within which the head body 312 of the oral care refill head 300 is positioned.

As mentioned previously, there is a user-operated actuator 135 located on the gripping portion 210 of the handle 200. The user-operated actuator 135 is in operable coupling with the actuator unit 130 shown in FIG. 2 and described above. The user-operated actuator 135 is configured to control one or more functions of the oral care implement 100. The user-operated actuator 135 comprises an actuator plate 136 positioned within the actuator aperture 222 of the handle housing 220. In the exemplified embodiment, the user-operated actuator 135 comprises the mode selection switch (or button) 128 and the power switch (or button) 129 that are located on the gripping portion 210 of the handle 200 so that they can be easily actuated by a user. Specifically, a user can depress the mode selection switch 128 to change the mode (from normal to quiet mode as described above) and the user can depress the power switch 129 to power the oral care implement 100 on and off. The mode selection switch 128 and the power switch 129 are press button switches in the exemplified embodiment, but they could be slide switches, toggle switches, limit switches, throw switches, mechanical switches, electronic switches, conductive touch switches, or the like in various different embodiments.

Furthermore, the oral care implement 100 comprises an illumination ring 150 located on the handle 200, and more specifically on the gripping portion 210 of the handle 200. Even more specifically, the illumination ring 150 is located on the handle 200 so that it surrounds the user-operated actuator 135. Thus, in the exemplified embodiment the illumination ring 150 is an oval-shaped ring that completely surrounds the user-operated actuator 135. The illumination ring 150 may be formed of a light transmissive material so that light emitted from inside of the handle 200 as described above can be transmitted through the illumination ring 150 to provide an indication to a user of the amount of time that has elapsed during an oral care session. The connectivity indicator 212a and the power source indicator 212b described above are also shown in FIG. 15.

In the exemplified embodiment, the illumination ring 150 has a continuous exposed ring surface that surrounds the user-operated actuator 135. Thus, in the exemplified embodiment the illumination ring 150 forms a continuous, unbroken ring-like shape. However, the invention is not to be so limited in all embodiments and the illumination ring 150 may comprise ring segments that are spaced apart but collectively define a ring-like shape. Regardless, the illumination ring 150 is exposed along an outer surface 215 of the gripping portion 210 of the handle 200.

Figure 16A:
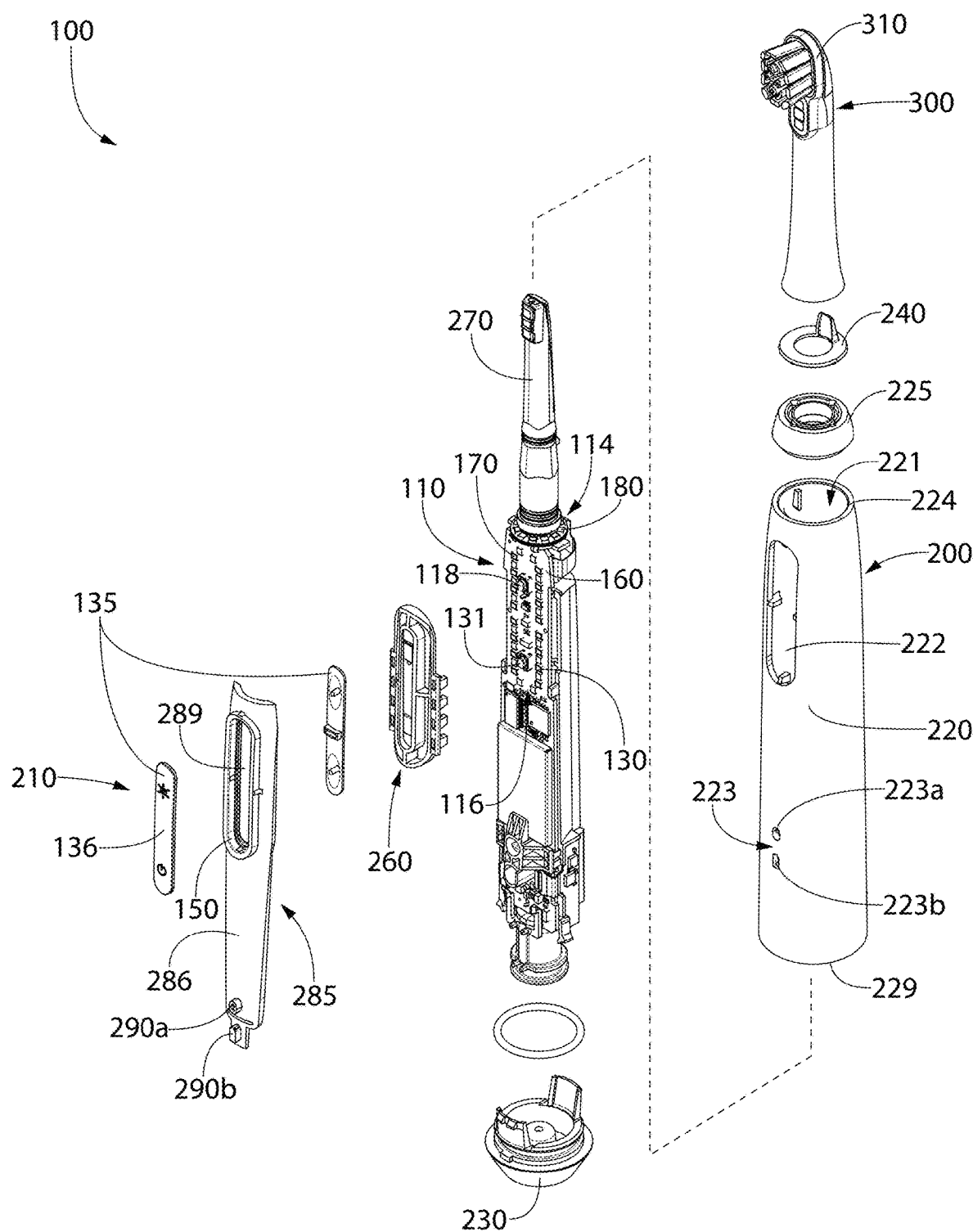
FIG. 16A is an exploded front perspective view of the oral care implement of FIG. 1.
Figure 16B:
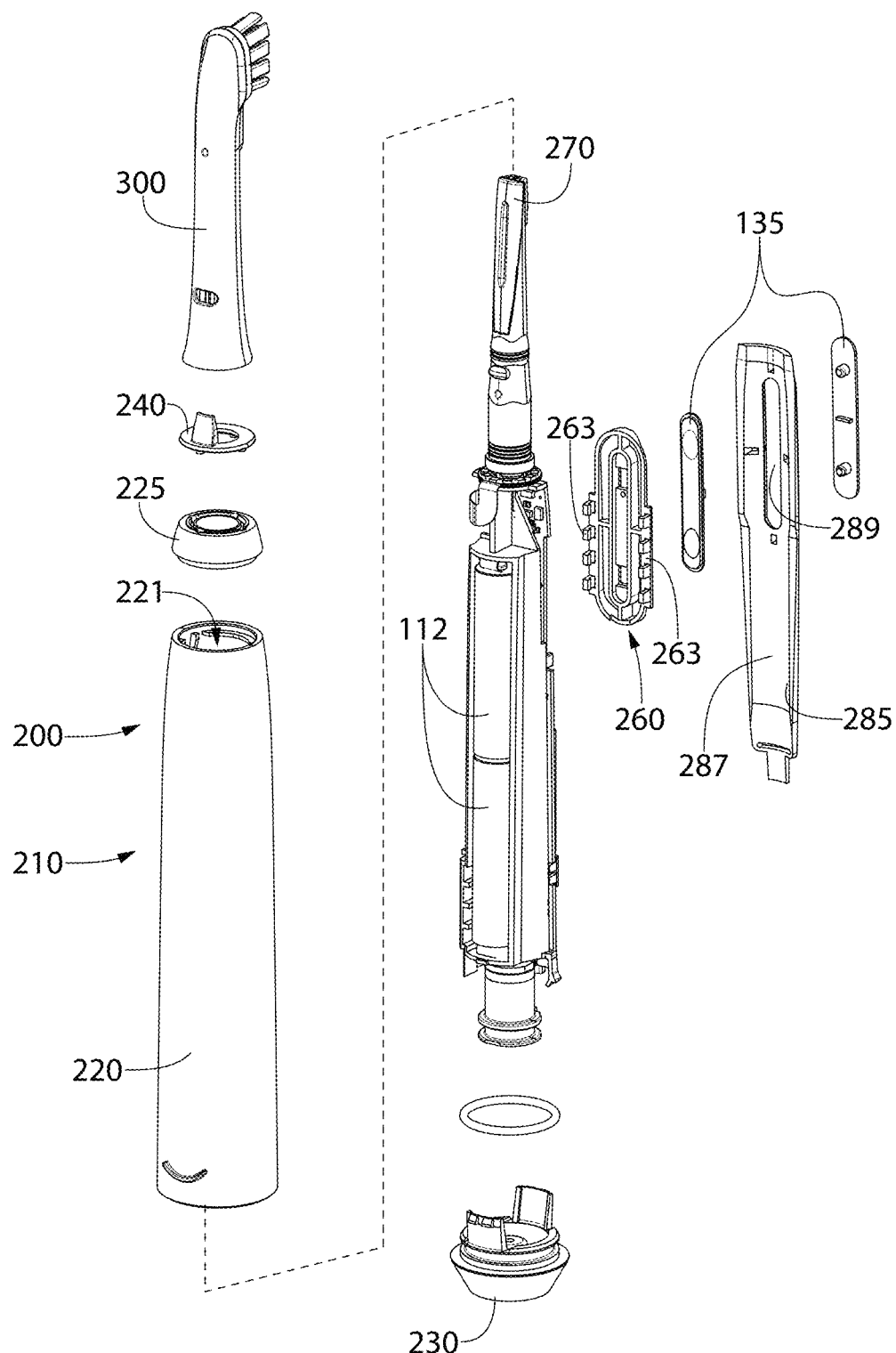
FIG. 16B is an exploded rear perspective view of the oral care implement of FIG. 1.

Referring to FIGS. 16A and 16B, the oral care implement 100 is depicted in a front perspective exploded view and a rear perspective exploded view so that the different components that form the oral care implement 100 can be seen. Some of these components will be shown separately and described in more detail below. The oral care implement 100 comprises the handle 200 and the oral care refill head 300. The gripping portion 210, the engagement component 240, and the stem 270 of the handle 200 are shown in these views. The gripping portion 210 of the handle 200 comprises a handle housing 220 that defines an interior cavity 221 within which several components of the control circuit 110 that are housed in the oral care implement 100 are located. Thus, the handle housing 220 is at least partially hollow so that it comprises the interior cavity 221. The handle housing 220 has an opening 224 at its distal end and an opening 229 at its proximal end. An end cap 230 is provided to close the opening 229 at the proximal end of the handle housing 220.

The handle housing 220 also comprises an actuator aperture 222 formed into a front surface of the handle housing 220 and providing a passageway from the exterior environment and into the interior cavity 221. When the oral care implement 100 is assembled as shown in FIG. 15, the illumination ring 150 protrudes into the actuator aperture 222 and the user-operated actuator 135 closes the remaining portion of the actuator aperture 222 that is not filled by the illumination ring 150. The handle housing 220 also comprises a status aperture 223 that is spaced from the actuator aperture 222. In fact, the status aperture 223 comprises a first status aperture 223a and a second status aperture 223b that are aligned with the connectivity and power source indicators 212a, 212b mentioned above.

The handle 200 further comprises a collar 225 that is coupled to the gripping portion 210. When the handle 200 is assembled, the collar 225 is positioned between the engagement component 240 and the gripping portion 221 of the handle 200. Thus, the engagement portion 240 is coupled directly to the collar 225, which in turn is coupled to a distal end of the gripping portion 210. The collar 225 may comprise or be formed from a light transmissive material so that the collar 225 forms a light ring that circumscribes a longitudinal axis of the handle 200, as will be described in greater detail below.

The oral care implement 100 further comprises a circuit board 160 on which one or more of the components of the control circuit 110 are located. Specifically, in the exemplified embodiment the mode selection unit 118 and the power unit 131 of the actuator unit 130 are mounted on the circuit board 160. Furthermore, in this embodiment the time indicator unit 116 is also mounted to the circuit board 160. More specifically, in the exemplified embodiment the time indicator unit 116 comprises a plurality of light sources 170 (only one of which is labeled in FIG. 16A to avoid clutter). The plurality of light sources 170 of the time indicator unit 116 are arranged in a ring or a loop that surrounds the mode selection unit 118 and the power unit 131 of the actuator unit 130. The plurality of light sources 170 are configured to light up or illuminate in groupings to indicate the elapse of time during an oral care session, as will be discussed in greater detail below. In one embodiment, the plurality of light sources 170 are arranged in four groups so that each of the light sources 170 in a single group illuminate simultaneously during an oral care session. Again, the specific illumination pattern for the light sources 170 of the time indicator unit 116 will be described below in accordance with an exemplary embodiment of the present invention. The timer unit 115 (see FIG. 2) that tracks time during the oral care session is operably coupled to the light sources 170 of the time indicator unit 116 as described above (either directly or indirectly by way of the processor 111).

The sensor indicator unit 114 is also provided in the form of a plurality of light sources 180 (only one of which is labeled to avoid clutter) in the exemplified embodiment. When the handle 200 is fully assembled, the collar 225 is adjacent to and/or covers the light source 180 of the sensor indicator unit 114. Thus, the light generated by the light sources 180 of the sensor indicator unit 114 emits through the collar 225. For this reason, the collar 225 is preferably formed of a light transmissive material, although the degree of light transmissivity may vary so long as the light emitted by the light sources 180 can be seen through the collar 225.

The gripping portion 210 of the handle 200 further comprises an illumination component 285 through which the light generated by the light sources 170 of the time indicator unit 116 is emitted for visualization by a user. The illumination component 285 comprises a plate body 286 and the illumination ring 150. The plate body 286 comprises a front surface 287 and a rear surface 288. When the gripping portion 210 of the handle 200 is assembled, the rear surface 288 of the plate body 286 faces the circuit board 160 and the front surface 287 of the plate body 286 faces the inner surface of the handle housing 220. The illumination ring 150 protrudes from the front surface 287 of the plate body 286. Furthermore, the plate body 286 has an actuator aperture 289 extending from the front surface 287 to the rear surface 288. The illumination ring 150 protrudes from the front surface 287 of the plate body 286 and surrounds the actuator aperture 289 of the plate body 286.

The illumination component 285 also comprises a pair of status protuberances including a connectivity status protuberance 290*a* and a power source status protuberance 290*b*. The illumination component 285 in its entirety may be light transmissive in some embodiments. In other embodiments, at least the illumination ring 150, the connectivity status protuberance 290*a*, and the power source status protuberance 290*b* are formed from a light transmissive material so that light emitted from beneath the illumination component 285 (i.e., from light sources on the circuit board 160) shines through those portions of the illumination component 285. However, it should be appreciated that the illumination ring 150, the connectivity status protuberance 290*a*, and the power source status protuberance 290*b* are the only portions of the illumination component 285 which are exposed along an outer surface of the gripping portion 210 of the handle 200. The remainder of the illumination component 285 is hidden behind the handle housing 220. Thus, if the handle housing 220 is opaque and the illumination component 285 is light transmissive, light emitted from the various light sources described herein will only be visible along the exposed portions of the handle that are formed from the illumination component 285.

Figure 17:
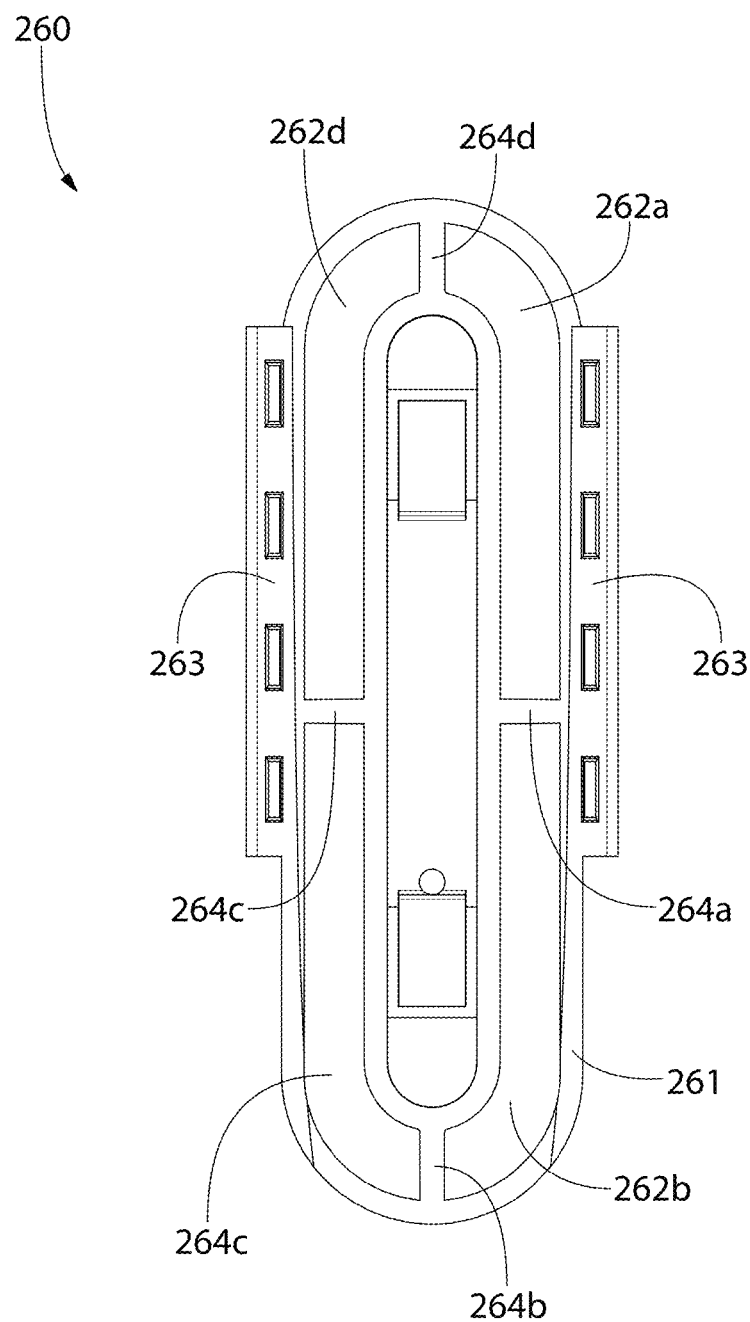
FIG. 17 is a front view of a light divider component of the oral care implement of FIG. 1.

Referring to FIGS. 16A, 16B, and 17, the gripping portion 210 of the handle 200 further comprises a light divider component 260. The light divider component 260 comprises a body 261 having a plurality of arcuate apertures 262*a-d* arranged in a ring. Each of the arcuate apertures 262*a-d* is separated from an adjacent one of the arcuate apertures 262*a-d* by a divider wall 264*a-d*. The ring arrangement of the plurality of arcuate apertures 262*a-d* is aligned with the illumination ring 150 when the gripping portion 210 of the handle 200 is assembled as described herein. The light divider component 260 also comprises a pair of connection elements 263 protruding from the body 261 to facilitate coupling of the light divider component 260 to the circuit board 160. The light divider component 260 may be formed of an opaque material in some embodiments.

Figure 18:
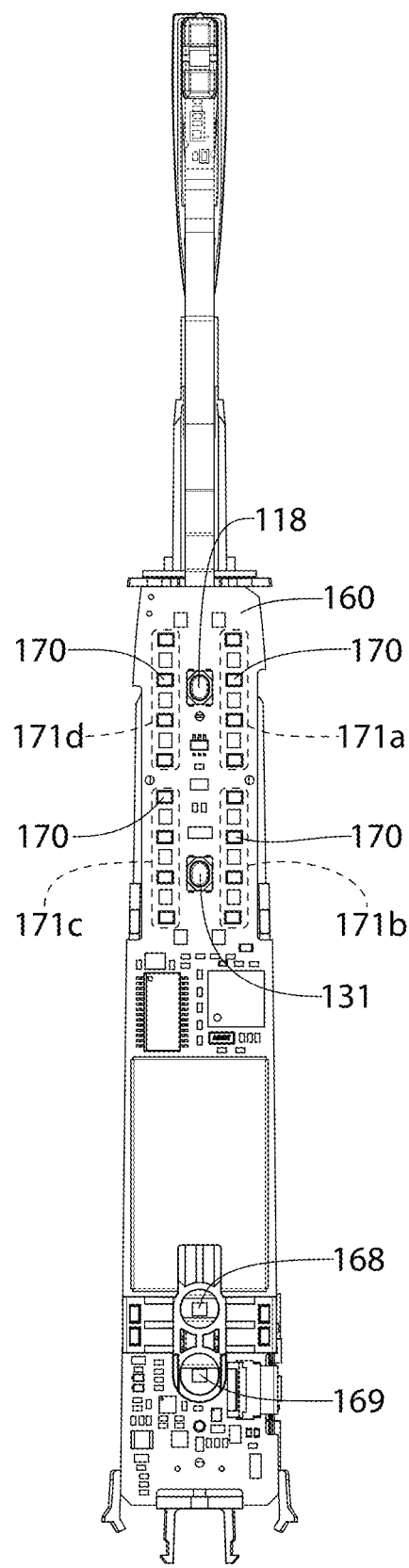
FIG. 18 is a front view of a circuit board of the oral care implement of FIG. 1.

FIG. 18 provides a front view of the circuit board 160 and the plurality of light sources 170 of the time indicator unit 116. This view better illustrates the plurality of light sources 170 of the time indicator unit 116 surrounding the mode selection unit 118 and the power unit 131. Furthermore, as can be seen in FIG. 18, the plurality of light sources 170 are arranged in a first quadrant grouping 171*a*, a second quadrant grouping 171*b*, a third quadrant grouping 171*c*, and a fourth quadrant grouping 171*d*. As mentioned previously, the light sources 170 are illuminated in groups. Specifically, the light sources 170 of the first quadrant grouping 171*a* are illuminated simultaneously, the light sources 170 of the second quadrant grouping 171*b* are illuminated simultaneously, the light sources 170 of the third quadrant grouping 171*c* are illuminated simultaneously, and the light sources 171*d* of the fourth quadrant grouping 171*d* are illuminated simultaneously. Thus, the oral care session can be broken down into quarters such that after the passage of each quarter of the total desired time for the oral care session, another one of the quadrant groupings 171*a-d* is illuminated to indicate the same to the user.

The control circuit 110 further comprises a connectivity status light source 168 mounted to the circuit board 160 and power source status light source 169 mounted to the circuit board 160. Each of the light sources mentioned herein may be light emitting diodes or any other device configured to generate light in the manner described herein. The connectivity status light source 168 is aligned with the first status aperture 223*a* of the handle housing 220 and with the connectivity status protuberance 290*a* of the illumination component 285 so that light emitted by the connectivity status light source 168 can pass through the connectivity status protuberance 290*a* to form the connectivity indicator 212*a* on the front surface of the gripping portion 210 of the handle 200 (see FIG. 15). Similarly, the power source status light source 169 is aligned with the second status aperture 223*b* in the handle housing 220 and with the power source status protuberance 290*b* of the illumination component 285 so that light emitted by the power source status light source 169 can pass through the power source status protuberance 290*b* to form the power source indicator 212*b* on the front surface of the gripping portion 210 of the handle 200 (see FIG. 15).

Figure 19:
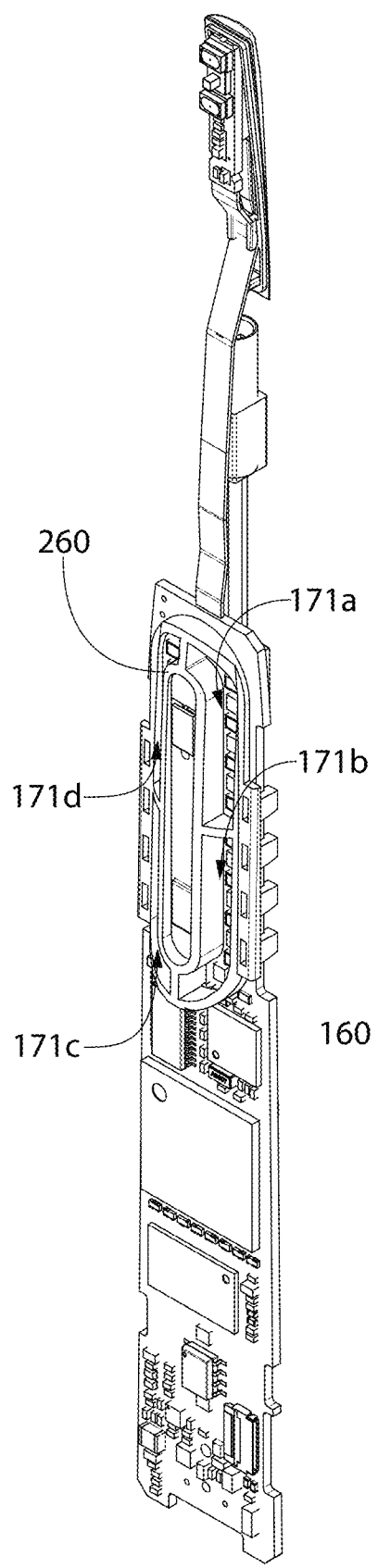
FIG. 19 is a perspective view of the circuit board of FIG. 18 with the light divider component of FIG. 17 coupled thereto.

As shown in FIG. 19, the light divider component 260 is coupled to the circuit board 160 on which the light sources 170 of the time indicator unit 116 are mounted. Specifically, the pair of connection elements 263 wrap around the periphery of the circuit board 160 to couple the light divider component 260 to the circuit board 160. In some embodiments, the light divider component 260 may snap-fit to the circuit board 160. When the light divider component 260 is coupled to the circuit board 160, the light sources 170 of the first quadrant grouping 171*a* are aligned with a first one of the plurality of arcuate apertures 262*a* in the light divider component 260, the light sources 170 of the second quadrant grouping 171*b* are aligned with a second one of the plurality of arcuate apertures 262*b*, the light sources 170 of the third quadrant grouping 171*c* are aligned with a third one of the plurality of arcuate apertures 262*c*, and the light sources 171*d* of the fourth quadrant grouping 171*d* are aligned with a fourth one of the plurality of arcuate apertures 262*d*.

Figure 20:
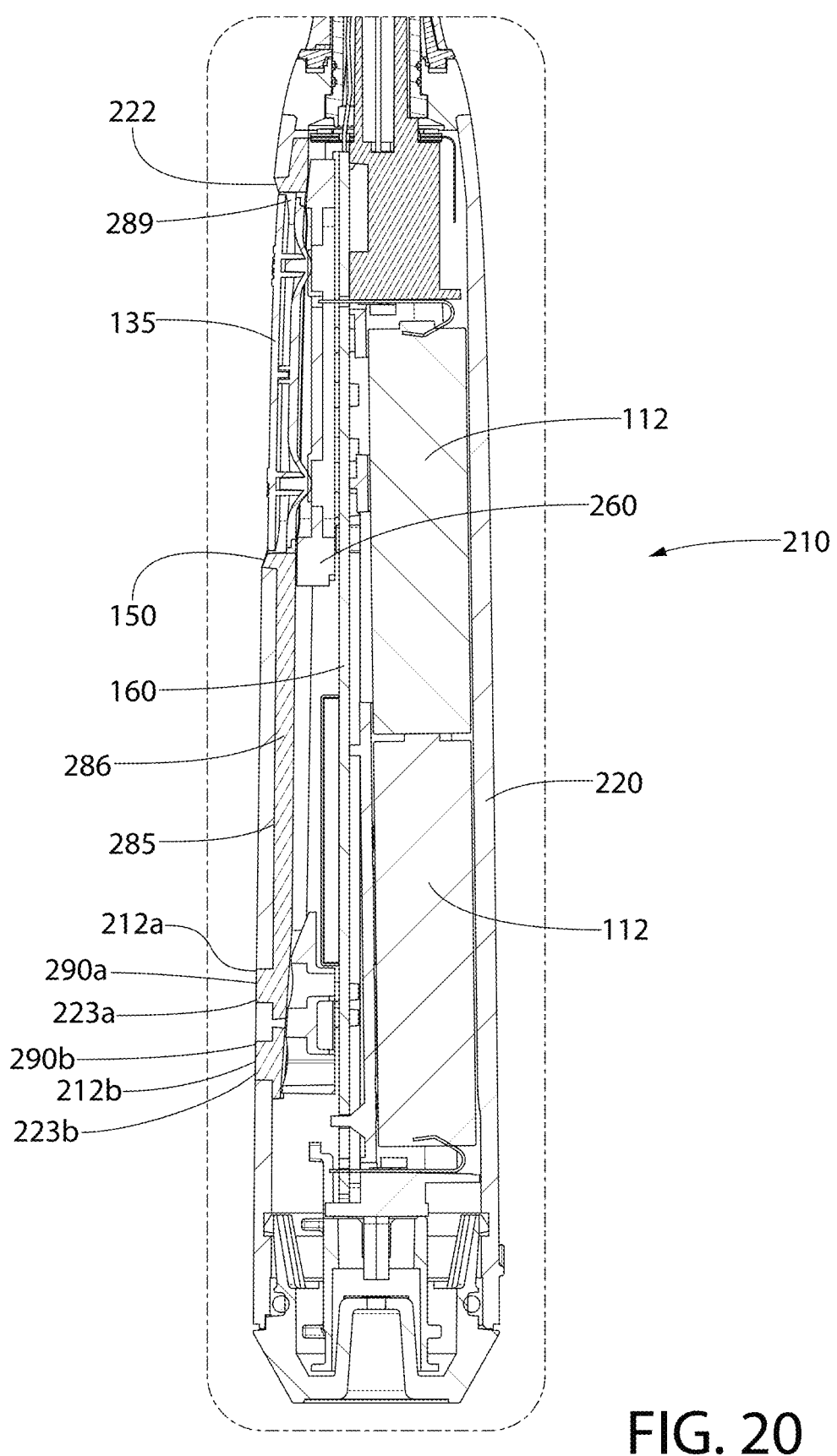
FIG. 20 is a close-up view of area XX of FIG. 11.

Referring again to FIG. 16A along with FIG. 20, the assembly of the oral care implement 100 will be described.

First, the light divider component 260 is coupled to the circuit board 160 as described above and shown in FIG. 18. Next, the illumination component 285 is coupled to the light divider component 260 and circuit board 160 assembly. The components of the user-operated actuator 135 may be attached to one another within the actuator aperture 289 of the illumination component 285 before the illumination component 285 is attached to the light divider component 260 and circuit board 160 assembly. Once all of these components are attached together, that assembly is inserted through the opening 229 in the proximal end of the handle housing 220 and into the interior cavity 221 of the handle housing 220 until the stem 270 protrudes from the distal end of the handle housing 220. Of course, in some embodiments rather than inserting the previously noted assembly through the opening 229 in the proximal end of the handle housing 220, the handle housing 220 may comprise two separate parts that are simply coupled together around the assembly. Thus, variations in the assembly process may exist in accordance with the invention described herein.

Once the assembly noted above is inserted into the interior cavity 221 of the handle housing 220, the illumination component 285 may be snap-fit to the handle housing 220. In this regard, the illumination ring 150 extends into the actuator aperture 222 of the handle housing 220, the connectivity status protuberance 290a extends into the first status aperture 223a of the handle housing 220, and the power source status protuberance 290b extends into the second status aperture 223b of the handle housing 220. Furthermore, as can be seen the illumination ring 150, the power source protuberance 290b, and the connectivity status protuberance 290a are flush with the outer surface of the handle housing 220 such that the illumination ring 150, the power source protuberance 290b, and the connectivity status protuberance 290 form a part of an exposed surface of the gripping portion 210 of the handle 200.

Referring to FIGS. 21A-21D and 22A-22d, the operation of the plurality of light sources 170 of the time indicator unit 116 will be described during an oral care session. First, when the oral care implement 100 is first powered on, all of the light sources 170 illuminate in a second color (e.g., blue) simultaneously so that the illumination ring 150 illuminates in the second color. Once a start brush command is sent to the oral care implement (which may be done automatically simply by placing the oral care tool into the user's mouth, or may require a user to activate a button or the like) or after a set period of time, the plurality of light sources 170 all deactivate and turn off. During the oral care session, the control circuit 110 (or the processor 111 thereof) is configured to activate the light sources 170 of the time indicator unit 116 in a manner that informs the user, during the oral care session, of the time that has passed during the performance of the oral care session. As will be appreciated from the description below, the control circuit 110 is configured to activate the light sources 170 of the time indicator unit 116 in a manner that sequentially illuminates segments of the illumination ring 150.

Figure 21D:
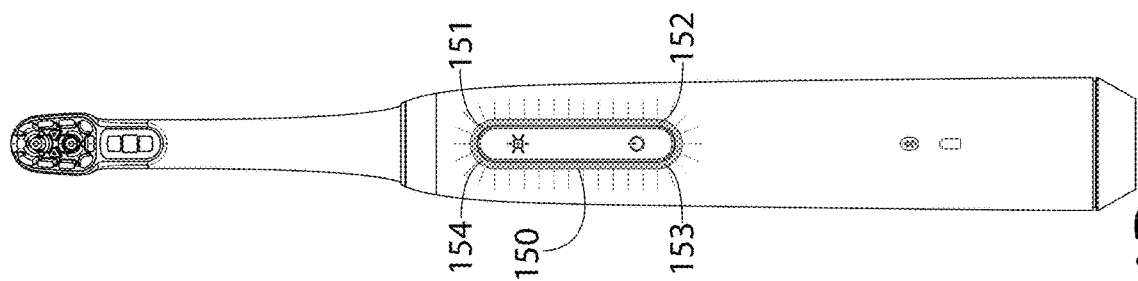
FIGS. 21A-21D are front views of the oral care implement of FIG. 1 illustrating progressive illumination of an illumination ring thereof over the passage of time.
Figure 21C:
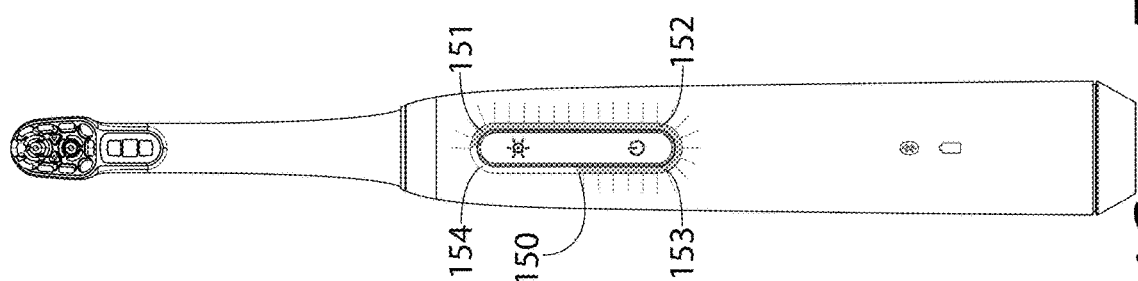
Figure 21B:
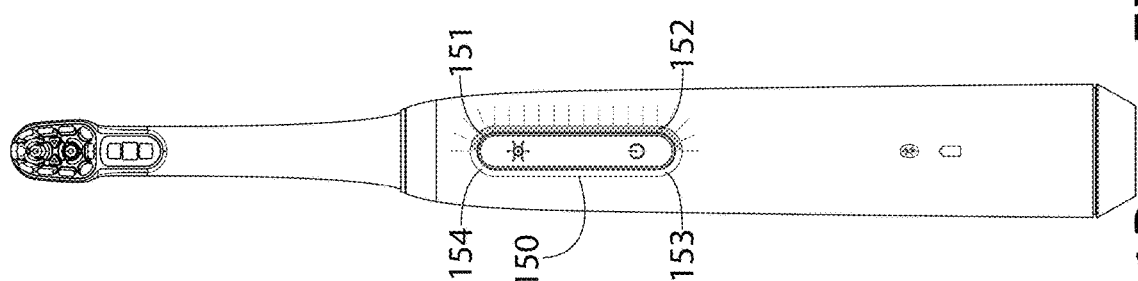
Figure 21A:
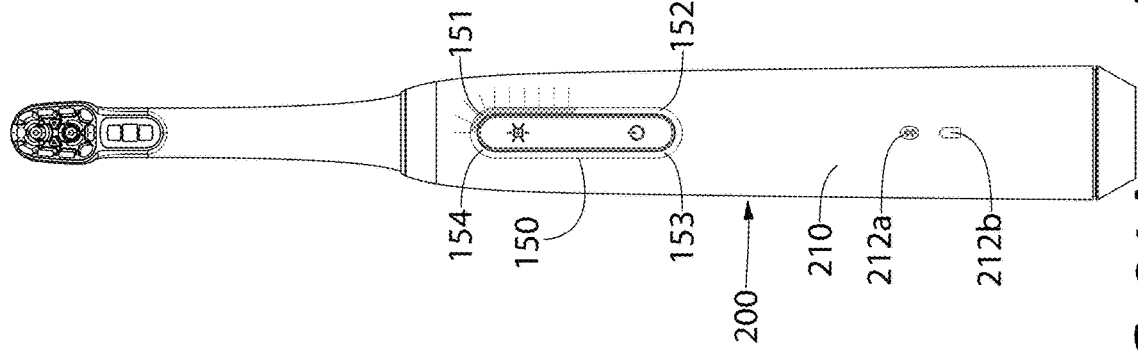

Referring to FIGS. 21A and 22A, after expiration of a first time period during the oral care session, the control circuit 110 is configured to activate the one or more light sources 170 in a manner that illuminates a first quadrant segment 151 of the illumination ring 150. This means that after the first time period has expired, the control circuit 110 activates all of the light sources 170 in the first quadrant grouping 171a, which in turn causes the first quadrant segment 151 of the illumination ring 150 to illuminate as the light from the light sources 170 in the first quadrant grouping 171a pass through the first quadrant segment 151 of the illumination ring 150. The first quadrant segment 151 of the illumination ring 150 is equivalent to the 12 O'clock to 3 O'clock region of the illumination ring 150.

As the time continues to elapse during the oral care session, the first quadrant segment 151 of the illumination ring 150 remains illuminated. Next, referring to FIGS. 21B and 22B, after expiration of a second time period during the oral care session, the control circuit 110 is configured to activate the one or more light sources 170 in a manner that illuminates the first quadrant segment 151 of the illumination ring 150 and a second quadrant segment 152 of the illumination ring 150. This means that after the second time period has expired, the control circuit 110 activates all of the light sources 170 in the first quadrant grouping 171a and all of the light sources 170 in the second quadrant grouping 171b, which in turn causes the first and second quadrant segments 151, 152 of the illumination ring 150 to illuminate as the light from the light sources 170 in the first and second quadrant groupings 171a, 171b pass through the first and second quadrant segments 151, 152 of the illumination ring 150. The second quadrant segment 152 of the illumination ring 150 is equivalent to the 3 O'clock to the 6 O'clock region of the illumination ring, and thus after elapse of the second time period the 12 O'clock to 6 O'clock region of the illumination ring 150 is illuminated as shown in FIG. 21B.

As the time continues to elapse during the oral care session, the first and second quadrant segments 151, 152 of the illumination ring 150 remain illuminated. Next, referring to FIGS. 21C and 22C, after expiration of a third time period during the oral care session, the control circuit 110 is configured to activate the one or more light sources 170 in a manner that illuminates the first and second quadrant segments 151, 152 of the illumination ring 150 and also a third quadrant segment 153 of the illumination ring 150. This means that after the third time period has expired, the control circuit 110 activates all of the light sources 170 in the first quadrant grouping 171a, all of the light sources 170 in the second quadrant grouping 171b, and all of the light sources 170 in the third quadrant grouping 171c, which in turn causes the first, second, and third quadrant segments 151, 152, 153 of the illumination ring 150 to illuminate as the light from the light sources 170 in the first, second, and third quadrant groupings 171a, 171b, 171c pass through the first, second, and third quadrant segments 151, 152, 153 of the illumination ring 150. The third quadrant segment 153 of the illumination ring 150 is equivalent to the 6 O'clock to the 9 O'clock region of the illumination ring, and thus after elapse of the third time period the 12 O'clock to 9 O'clock region of the illumination ring 150 is illuminated as shown in FIG. 21C.

As the time continues to elapse during the oral care session, the first, second, and third quadrant segments 151, 152, 153 of the illumination ring 150 remain illuminated. Next, referring to FIGS. 21D and 22D, after expiration of a fourth time period during the oral care session, the control circuit 110 is configured to activate the one or more light sources 170 in a manner that illuminates the first, second, and third quadrant segments 151, 152, 153 of the illumination ring 150 and also a fourth quadrant segment 154 of the illumination ring 150. This means that after the fourth time period has expired, the control circuit 110 activates all of the light sources 170 in the first quadrant grouping 171a, all of the light sources 170 in the second quadrant grouping 171b, all of the light sources 170 in the third quadrant grouping 171c, and all of the light sources in the fourth quadrant grouping 171d, which in turn causes the first, second, third, and fourth quadrant segments 151, 152, 153, 154 of the illumination ring 150 to illuminate as the light from the light sources 170 in the first, second, third, and fourth quadrant groupings 171a, 171b, 171c, 171d pass through the first, second, third, and fourth quadrant segments 151, 152, 153, 154 of the illumination ring 150. The fourth quadrant segment 154 of the illumination ring 150 is equivalent to the 9 O'clock to the 10 O'clock region of the illumination ring, and thus after elapse of the fourth time period the 12 O'clock to 12 O'clock region of the illumination ring 150 is illuminated as shown in FIG. 21D.

In some embodiments, the fourth time period may correspond to a recommended brushing time. The recommended brushing time may be two minutes, although it could be more or less than two minutes. In such embodiments, each of the first, second, third, and fourth time periods is thirty seconds. In some embodiments, the recommended brushing time could be a user-selectable parameter such that the user can determine how long the brushing time should be, and may set the timer for that length of time. In the exemplified embodiment, there are four time periods, and thus one-fourth of the light sources 170 are activated at the expiration of each of the time periods to illuminate one-fourth of the illumination ring 150. However, there could be more or less than four time periods and the brushing time and illumination of the light sources may be divided up accordingly.

Furthermore, during the oral care session each of light sources 170 may illuminate in a first color (e.g., white). Thus, during the oral care session each of the light sources 170 may illuminate in the same color when activated. In other embodiments, the light sources 170 in each grouping may illuminate in different colors relative to each other or relative to the other groupings. Thus, variations in the colors being emitted from the light source 170 may fall within the scope of the invention described herein.

The control circuit 110 is also configured to activate the connectivity status light source 168 and the power source status light source 169 to illuminate the connectivity indicator 212a on the gripping portion 210 of the handle 200 and the power source indicator 212b on the gripping portion 210 of the handle 200. These features are shown in FIGS. 21A-21D, but called out only in FIG. 21A. The control circuit 110 will activate the connectivity status light source 168 and/or the power source status light source 169 upon a status condition being satisfied. Thus, for example, the control circuit 110 may activate the connectivity status light source 168 upon the oral care implement 100 being placed into operable communication with the electronic device 500. In some embodiments, the connectivity status light source 168 may blink when it is being connected to an electronic device 500 and then subsequently turn off once it is connected. In other embodiments, the connectivity status light source 168 may blink when it is being connected to the electronic device 500 and then remain on continuously thereafter. The control circuit 110 may activate the power source status light source 169 to indicate a level of power remaining in the power source 112. Different colors of light may be used to indicate different statuses of the power source 112 (red may indicate low power or less than three uses remaining), green may depict full or near full power or greater than five uses remaining, yellow may indicate intermediate power or somewhere between three to five uses remaining, or the like).

Furthermore, it should be appreciated that operation of the oral care implement 100 including the time indicator unit 116 may be paused during an oral care session. Such pause may occur by a user activating a pause button associated with the control circuit 110 (either on the oral care implement 100 or on the electronic device 500). Alternatively, such pause may occur automatically when the control circuit 110 detects that the oral care implement 100 has been removed from the user's oral cavity. When paused, all of the light sources 170 associated with the time indicator unit 116 turn off (inactivate). However, once the operation resumes either by the user activating a resume button associated with the control circuit 110 or the control circuit 110 detecting that the oral care implement 100 has been placed back into the user's mouth, the light sources 170 power back on in the manner that they were powered on just prior to the operation being paused. Thus, if the first grouping 171a of light sources 170 were activated prior to the pause, the first grouping 171a of the light sources 170 would be reactivated when the operation resumes.

Furthermore, in some embodiments, after the expiration of the fourth time period, which corresponds to a recommended brushing time, all of the light sources 170 of the first through fourth groupings 171a-d are activated and powered on. A user may continue to clean his/her oral cavity, and during such time the light sources 170 may remain illuminated. In some embodiments, the light sources 170 may remain illuminated for an additional time period, and after expiration of the additional time period all of the light sources 170 of the time indicator unit 116 may deactivate and power off. In some embodiments, the additional time period may be one minute. In other embodiments, the additional time period may be two minutes, or three minutes, or four minutes, etc.

Figure 23:
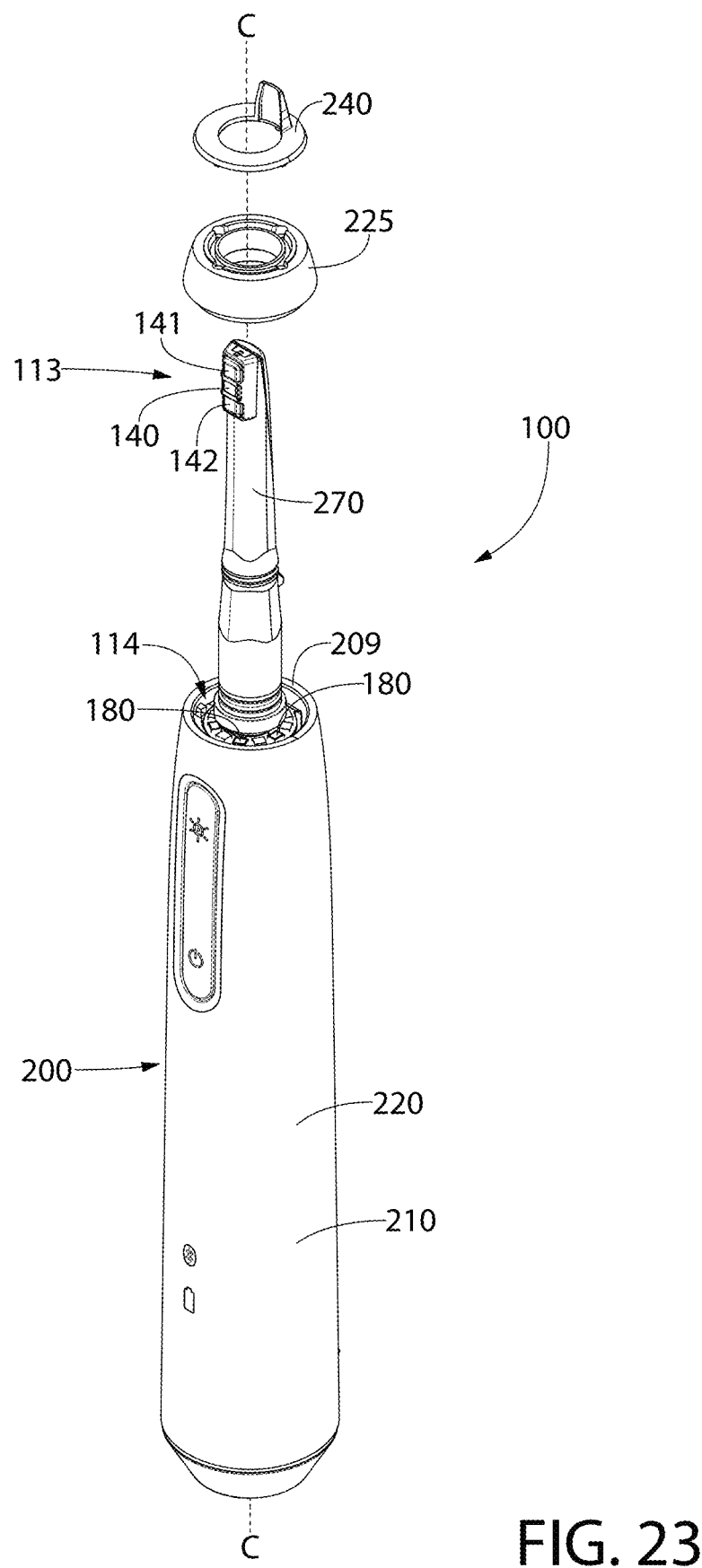
FIG. 23 is a partially exploded view of a handle of the oral care implement of FIG. 1, wherein a collar and an engagement component are exploded from a gripping portion of the handle to expose light sources of a sensor indicator unit.

Referring to FIGS. 2, 16A, and 23, the oral care implement 100 will be further described. As mentioned previously, the control circuit 110 comprises a first sensor unit 113 and a sensor indicator unit 114 that are integrated into or otherwise coupled to the oral care implement 100. As described previously, the first sensor unit 113 may comprise the optical sensor 140, the light source 141, and the receiver 142 as noted previously. However, the first sensor unit 113 is not limited to comprising those components and may comprise those components in addition to other components, may comprise some or all of those components, or may comprise none of those components and only other components. The first sensor unit 113 comprises all of the hardware and/or software required for it to function as described herein.

In the exemplified embodiment, the first sensor unit 113 is configured to detect: (1) the presence of an oral surface during performance of an oral care session using the oral care implement 100; and (2) the presence (or lack thereof) of an oral malady on the oral surface during performance of the oral care session. The first sensor unit 113 may also detect whether the oral care tool 310 is located in the oral cavity or outside of the oral cavity. The oral malady may be any of the oral care parameters described above, such as a physiological oral condition. The oral malady may be the existence of plaque on the teeth or other oral surfaces in one exemplified embodiment. However, the invention is not to be so limited and the oral malady may take on any forms and may be any undesirable health characteristic that can affect the oral cavity and be detected with one or more sensors (in operable communication with or comprising a processor that can process data acquired by the sensors). As noted above, the presence of the oral surface and the existence or lack thereof of the oral malady may be detected using one or more of the optical sensor 140, the light source 141, and the receiver 142 in one particular embodiment of the present invention.

The first sensor unit 113 is operably coupled to the sensor indicator unit 114, either via a direct coupling or through an intermediate coupling of both of the first sensor unit 113 and the sensor indicator unit 114 to the processor 111. As noted above, in the exemplified embodiment the sensor indicator unit 114 comprises a plurality of light sources 180 that are located in the handle 200 adjacent to a distal end 209 of the gripping portion 210 of the handle 200. Furthermore, each of the light sources 180 is pointed upwards towards the distal end 209 of the gripping portion 210 (i.e., towards the oral care tool 310 of the oral care refill head 300). Thus, the light sources 180 of the sensor indicator unit 114 are configured to emit light in an upward directly.

The collar 225 is coupled to the distal end 209 of the gripping portion 210 of the handle 200. In the exemplified embodiment, the collar 225 is positioned axially just above the light sources 180 of the sensor indicator unit 114. Thus, the collar 225 surrounds the light sources 180, but it is aligned with the light sources 180. Stated another way, there is no plane transverse to the longitudinal axis of the oral care implement 100 which would intersect both the collar 225 and the light sources 180 of the sensor indicator unit 114. However, in other embodiments the light sources 180 of the sensor indicator unit 114 could be positioned so as to be aligned with the collar 225. As noted above, the collar 225 is preferably formed of a light transmissive material. Thus, light emitted from the plurality of light sources 180 of the sensor indicator unit 114 is visible through the collar 225. The handle housing 220 of the gripping portion 210 of the handle 200 may not be light transmissive. Thus, the light emitted from the light sources 180 is visible only through the collar 225 as it cannot be seen through the opaque handle housing 220.

Figure 24:
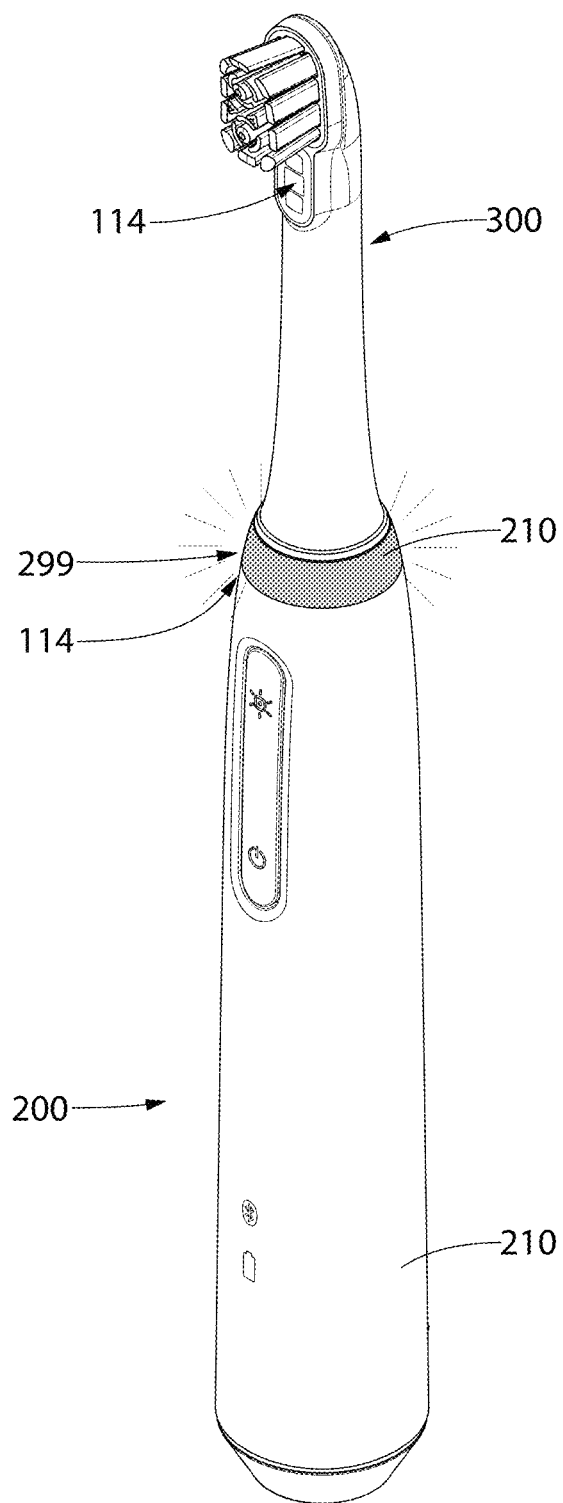
FIG. 24 is a perspective view of the oral care implement of FIG. 1 illustrating a light ring thereof illuminated.

Referring to FIGS. 23 and 24, in the exemplified embodiment the light sources 180 of the sensor indicator unit 114 are arranged along a ring or loop that surrounds the longitudinal axis C-C of the gripping portion 210 of the handle 200 of the oral care implement 100. Thus, the sensor indicator unit 114, which comprises the plurality of light sources 180 and the collar 225 that is light transmissive in the exemplified embodiment, is in the form of a light ring 299 provided on the handle 200. The light ring 299 circumscribes the longitudinal axis C-C of the gripping portion 210 of the handle 100 as noted above. As shown in FIG. 24, when one or more of the light sources 280 of the sensor indicator unit 114 are activated (powered on), the light ring 299 is illuminated to provide a visual cue to a user during an oral care session.

Operation of the first sensor unit 113 and the sensor indicator unit 114 will now be described in accordance with one embodiment of the present invention. Another more specific description of the operation will be provided below with reference to FIG. 25.

As noted previously, the control circuit 110 comprises, in operable coupling, the first sensor unit 113 and the sensor indicator unit 114. The first sensor unit 113 may be coupled to or integrated into the oral care implement 100. The sensor indicator unit 114 may also be coupled to or integrated into the oral care implement. The first sensor unit 113 is configured to detect the presence of the oral surface (i.e., teeth, gums, etc.) during an oral care session to determine whether the oral care tool 310 of the oral care implement 100 is located within a user's oral cavity or not. The first sensor unit 113 is also configured to detect the presence of an oral malady (which is plaque in the exemplified embodiment) on the oral surface during the oral care session. The control circuit 110, generally due to the coupling of the first sensor unit 113 and the sensor indicator unit 114 to the processor 111, is configured to generate different user perceptible stimuli with the sensor indicator unit 114 during the oral care session depending on whether the first sensor unit 113 is detecting the presence of the oral surface and/or is detecting the presence of an oral malady. Furthermore, the time elapsed during the oral care session also plays a role in the manner in which the control circuit causes the sensor indicator unit 114 to generate the various user perceptible stimuli.

As has been discussed in detail above, in the exemplified embodiment the sensor indicator unit 114 comprises the plurality of light sources 180, and thus the user perceptible stimuli are visual (i.e., the emission of light in one or more colors). As also discussed above, the user perceptible stimuli could take on other forms in other embodiments, such as being audible stimuli and/or tactile/haptic stimuli or any other user perceptible stimuli. Thus, in alternative embodiments the sensor indicator unit 114 may comprise one or more of a speaker, a vibration generator, a motor with an eccentric, a playback device with memory storing various audible outputs, or the like.

In the exemplified embodiment, the control circuit 110 is configured to generate at least four different user perceptible stimuli under different circumstances in accordance with what is detected by the first sensor unit 113. Thus, the control circuit 110 is configured to generate a first user perceptible stimulus with the sensor indicator unit 114 during the oral care session when the first sensor unit 113 is detecting the presence of the oral surface and the first sensor unit 113 is detecting that the oral surface is free of the oral malady. As mentioned above, the detection of the presence of the oral surface by the first sensor unit 113 is indicative of the oral care tool 310 of the oral care implement 100 being located in the oral cavity of a user. Thus, when the first sensor unit 113 determines that the oral care tool 310 is in the oral cavity (by detecting the presence of the oral surface) and determines that the oral surface is free of the oral malady (e.g., that the teeth are free of plaque), the sensor indicator unit 114 will generate a first user perceptible stimulus. In one embodiment, the first user perceptible stimulus may be the generation of a first color of light with the light sources 180 of the sensor indicator unit 114. In one embodiment, the first color of light may be white, although the invention is not to be so limited and the first color of light may be any color so long as it is distinguishable from any color used as the other user perceptible stimuli described herein.

In the exemplified embodiment, the control circuit 110 may be configured to generate a second user perceptible stimulus with the sensor indicator unit 114 when the first sensor unit 113 is detecting the presence of the oral surface and the first sensor unit 113 is detecting the presence of the oral malady on the oral surface. Thus, when the first sensor unit 113 determines that the oral care tool 310 is located in the user's oral cavity and that the oral malady is present (e.g., that there is plaque on the teeth), the control circuit 110 will cause the sensor indicator unit 114 to generate the second user perceptible stimulus. In the exemplified embodiment, the second user perceptible stimulus may be the generation of a second color of light with the light sources 180 of the sensor indicator unit 114. In one embodiment, the second color of light may be blue, although the invention is not to be so limited and the second color of light may be any color so long as it is distinguishable from the first color of light used as the first user perceptible stimulus. Thus, the first and second user perceptible stimuli (e.g., the first and second colors of light) are different from one another in some embodiments.

Moreover, in the exemplified embodiment the control circuit 110 may be configured to generate a third user perceptible stimulus with the sensor indicator unit 114 when, during the oral care session, the first sensor unit 113 is not detecting the presence of the oral surface. This can happen in several ways. First, the user may be holding the oral care tool 310 in the oral cavity in such an orientation the prevents the first sensor unit 113 from being able to detect the presence of the oral surface. For example, the first sensor unit 113 may detect the user's palate or uvula or some other surface in the oral cavity that is not the oral surface on which the oral malady may exist. Moreover, the first sensor unit 113 may detect some other feature outside of the mouth if the first sensor unit 113 is facing a direction that is out of the mouth. Second, the first sensor unit 113 may be covered or otherwise blocked or obstructed by fluids such as toothpaste and saliva (i.e., toothpaste slurry) in the mouth, thereby preventing the first sensor unit 113 from being able to detect anything. The first sensor unit 113 may require a clear visual path to the oral surfaces on which it is attempting to detect the oral malady. Therefore, if the first sensor unit 113 is covered by fluids or any the like, such a clear visual path may not exist. Thus, in the exemplified embodiment when the first sensor unit 113 cannot detect the oral surface, the oral circuit 110 may be configured to generate a third user perceptible stimulus with the sensor indicator unit 114.

In the exemplified embodiment, the third user perceptible stimulus may be the generation of a third color of light with the light sources 180 of the sensor indicator unit 114. In one embodiment, the third color of light may be red, although the invention is not to be so limited and the third color of light may be any color so long as it is distinguishable from the first color of light used as the first user perceptible stimulus and the second color of light used as the second user perceptible stimulus. Thus, the first, second, and third user perceptible stimuli (e.g., the first, second, and third colors of light) are different from one another in some embodiments. This allows a user to easily understand what is being indicated to her (e.g., user sees first color along light ring 299 indicates to the user that there is no plaque on her teeth, user sees second color along light ring 299 indicates to the user that there is plaque on her teeth, user sees a third color along the light ring 299 indicates to the user that the first sensor unit 113 is unable to perform its detecting function).

Moreover, in some embodiments the control circuit may cause a different user perceptible stimulus to be generated by the sensor indicator unit 114 depending on the cause of the first sensor unit 113 being unable to detect the presence of the oral surface. Thus, for example, if the first sensor unit 113 cannot detect the oral surface due to the first sensor unit 113 being covered (by a toothpaste slurry or the like), the control circuit 110 may be configured to generate the third user perceptible stimulus with the sensor indicator unit 114. However, if the first sensor unit 113 cannot detect the oral surface due to the orientation at which the oral care tool 310 is being held, the control circuit 110 may be configured to generate a fourth user perceptible stimulus with the sensor indicator unit 114. In some embodiments, the third user perceptible stimulus may be the emission of the third color of light in a solid pattern and the fourth user perceptible stimulus may be the emission of the third color of light in a flashing or blinking pattern. At any rate, each of the user perceptible stimulus should be different from one another, whether they are distinguishable due to the color of light generated, the pattern of light generated, or some other sensing function such as sound, vibration, or the like.

This can be valuable to a user of the oral care implement 100 to provide them the information that they need to remedy the cause of the first sensor unit 113 being unable to perform its detection function. Specifically, if the sensor indicator unit 114 generates the third user perceptible stimulus, the user will understand that the oral care tool 310 needs to be washed or rinsed to remove toothpaste slurry or other substances/objects that are blocking and/or covering the first sensor unit 113. Alternatively, if the sensor indicator unit 114 generates the fourth user perceptible stimulus, the indicator will understand that the oral care tool 310 needs to be reoriented within the oral cavity so that the first sensor unit 113 can have an unimpeded visual pathway to the oral surface so that it can perform its detecting function.

Furthermore, as noted above, in some embodiments the control circuit 110 may use data acquired from the timer unit 115 to determine which of the user perceptible stimulus should be generated by the sensor indicator unit 114 at a given time. In addition, the control circuit 110 may also use data acquired from the second sensor unit 117, which is configured to determine an orientation and/or position of the oral care implement 100 within the user's oral cavity during the oral care session, in determining which of the user perceptible stimulus should be generated by the sensor indicator unit 114. In that regard, the control circuit 110 may be configured to determine a zone of the user's oral cavity in which the oral care tool 310 is working during the oral care session. The determination of the zone of the user's oral cavity in which the oral care tool 310 is working may be determined based on information acquired from the first sensor unit 113 and the second sensor unit 117.

The oral cavity may be divided into any number of zones as may be desired. Furthermore, as discussed above, there is a desired amount of time during which a user should perform the oral care session. The amount of time divided by the number of zones provides a general indication of the amount of time that a user should keep the oral care tool 310 in a particular zone during the oral care session. In some embodiments, the amount of time that the oral care tool 310 should work in the same zone of the user's oral cavity may be approximately five seconds, in another embodiment it may be approximately ten seconds, in another embodiment it may be approximately twenty seconds. Of course, the amount of time is dependent on how many zones the oral cavity is divided into. The user perceptible stimuli generated by the sensor indicator unit 114 may function to indicate to a user that it is time to move on to a new zone.

Thus, in some embodiments, upon the control circuit 110 determining that the oral care tool 310 has been working in the same zone of the user's oral cavity for a predetermined period of time (i.e., a threshold period of time), the control circuit 110 may cause the sensor indicator unit 114 to switch from generating the second user perceptible stimulus to generating the first user perceptible stimulus. As noted above, the control circuit 110 is configured to generate a second user perceptible stimulus with the sensor indicator unit 114 when the presence of the oral malady is detected and the first user perceptible stimulus when the presence of the oral malady is not detected. However, there is an override function in that even if the oral malady is still detected by the first sensor unit 113, the control circuit 110 will cause the sensor indicator unit 114 to generate the first user perceptible stimulus if the oral care tool 310 has been working in the same zone for a period of time that exceeds a threshold period of time. The goal of this is to ensure that the user does not spend too much time in one zone, which can cause irritation to the oral surfaces and may also result in a user spending not enough time in other zones. Thus, the switch from the second user perceptible stimulus to the first user perceptible stimulus will prompt the user to move the oral care tool 310 to a different zone of the user's oral cavity during the oral care session. Again, the control circuit 110 may use data acquired by the first sensor unit 113, the timer unit 115, and the second sensor unit 117 to operate according to the above description.

Figure 25:
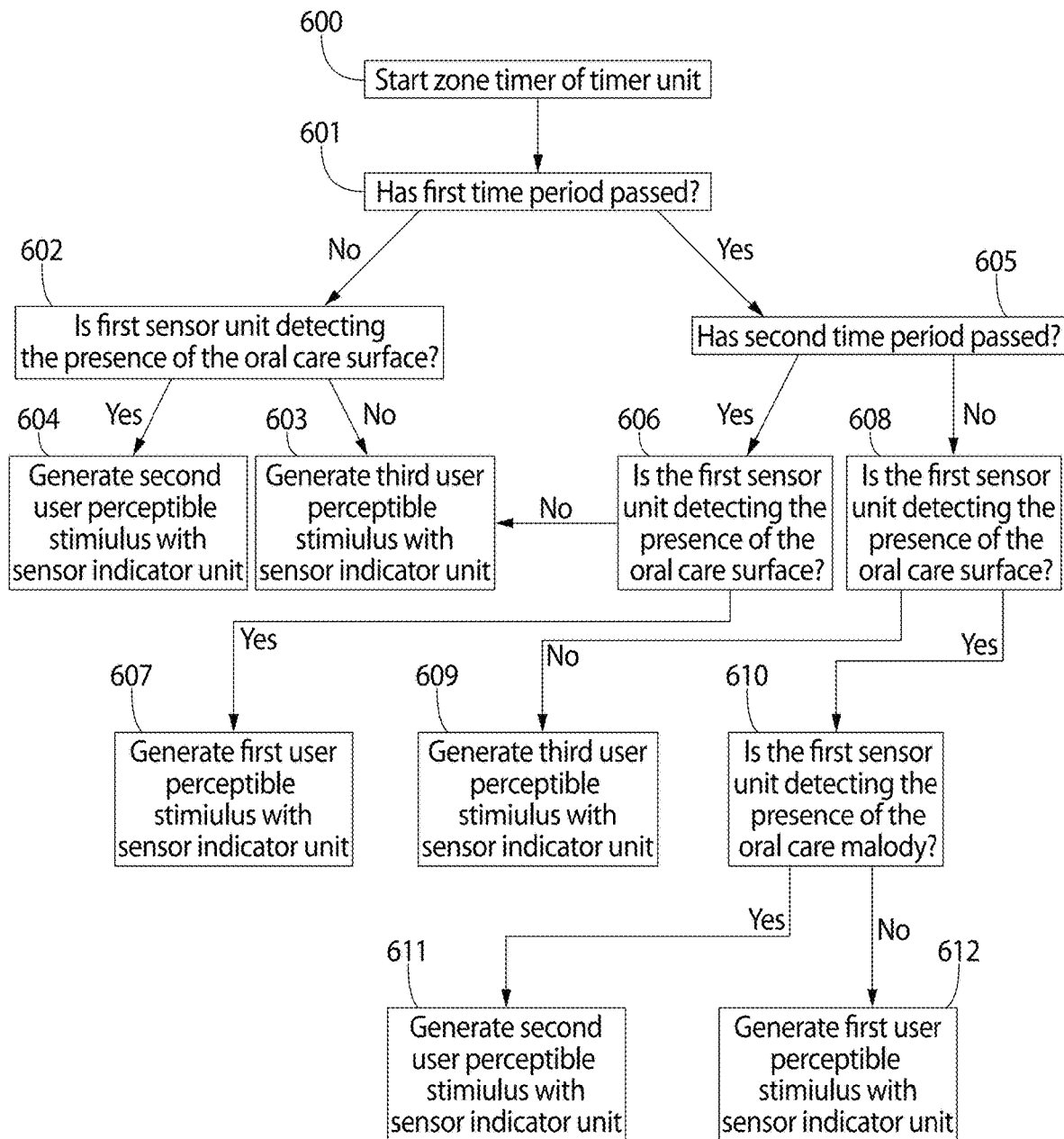
FIG. 25 is a flow chart showing operation of the control circuit of the oral care system of FIG. 1 in accordance with an embodiment of the present invention.

Referring to FIG. 25, operation of the control circuit 110 in accordance with an embodiment of the present invention will be described. The operation described below relates to the user perceptible stimuli generated by the sensor indicator unit 114 during an oral care session. As noted above, there is a desired total time for an oral care session (e.g., two minutes) and with that, a desired amount of time that the user should spend cleaning each zone of the oral cavity. The amount of time spent in each zone is dependent on the number of zones that the oral cavity is divided into, and the invention is not to be limited to a particular number of zones in all embodiments. However, in one embodiment there may be between five and twenty zones, or between five and ten zones, or between ten and twenty zones, or the like. To operate in accordance with FIG. 25 and the related disclosure, the first sensor unit 113 detects the presence of the oral surface and the presence of an oral malady on the oral surface during an oral care session, the timer unit 115 tracks time elapsed during performance of the oral care session and time elapsed with the oral care tool 310 in a single zone without moving to another zone, the second sensor unit 117 determines orientation of the oral care implement during the oral care session, and the sensor indicator unit 114 generates one or more user perceptible stimuli. The sensor indicator unit 114 may be referred to herein simply as an indicator unit in some embodiments because its operation may be dictated by components of the control circuit 110 other than the first sensor unit 113, including without limitation the timer unit 115, as described in more detail below.

Before discussing the FIG. 25 flow chart, some terms will be explained, When the control circuit 110 determines that a user has begun to work/clean in a new zone, the control circuit 110 starts a zone timer of the timer unit 115. Thus, the timer unit 115 may comprise a session timer that keeps track of total time elapsed during the oral care session and a zone timer that keeps track of time elapsed while the oral care tool 310 has been working in a single zone. Thus, at the start of a new cleaning session the session timer and the zone timer will both start keeping track of the time. The session timer will keep track of the entire time that the oral care session takes place. The zone timer will restart each time the oral care tool 310 is determined to be working in a new zone.

As noted above, the first user perceptible stimulus is generated when the first sensor unit 113 is not detecting plaque on the oral surface. The first user perceptible stimulus may also be used as a prompt or signal to the user to move the oral care tool 310 to the next zone. This may occur either based on there being no plaque detected, based on time elapsed with the oral care tool 310 in the same zone, or some combination of no plaque detected and time elapsed. As noted above, the second user perceptible stimulus is generated when the first sensor unit 113 is detecting plaque on the oral surface. The second user perceptible stimulus may also be used as a prompt or signal to the user to remain in the current zone and not move to the next zone. This may occur either based on there being plaque detected, based on time elapsed with the oral care tool 310 remaining in the same zone, or some combination of plaque detected and time elapsed, as described in more detail below.

In some embodiments, there may be two different time periods that are relevant while the oral care tool 310 remains in a single zone. The first time period is the minimum amount of time that the oral care tool 310 should remain in the same zone. Thus, as will be described in more detail below, the sensor indicator unit 114 will generate user perceptible stimulus that prompts the user to not leave the zone in which it is working during the first time period, regardless of whether the first sensor unit 113 is detecting plaque. This is to ensure that the user works in the same zone for a predetermined period of time necessary for a proper cleaning of the oral surfaces in that zone.

The second time period is the maximum amount of time that the oral care tool 310 should remain in the same zone. In some embodiments, the second time period may be ten seconds, or fifteen seconds, or twenty seconds, or the like. Thus, at the expiration of the second time period, the sensor indicator unit 114 will generate the first user perceptible stimulus. As noted above, the first user perceptible stimulus is generally generated when the first sensor unit 113 is not detecting any plaque. However, the first user perceptible stimulus may also be generated even if the first sensor unit 113 is detecting plaque, if the zone timer determines that the oral care tool 310 has been working in the same zone for a time that exceeds the second time period.

The time between the first and second time periods is when plaque (or other oral malady) detection with the first sensor unit 113 is more pertinent to operation of the sensor indicator unit 114. Specifically, in the time period between the first and second time periods, if the first sensor unit 113 is not detecting the oral malady, the control circuit 110 causes the sensor indicator unit 114 to generate the first user perceptible stimulus to prompt the user to move to the next zone. In the time period between the first and second time periods, if the first sensor unit 113 is detecting the oral malady, the control circuit 110 causes the sensor indicator unit 114 to generate the second user perceptible stimulus to prompt the user to remain in and continue working in the same zone.

Now, referring specifically to FIG. 25, the flow chart of operation in accordance with an embodiment of the present invention will be described. First, at step 600, the zone timer of the timer unit 115 is started. This may occur automatically upon the control circuit 110 (using the first sensor unit 113 and/or the second sensor unit 117) determining that the oral care tool 310 is positioned within the user's oral cavity. Once the control circuit 110 determines that an oral care session has started and the zone timer is started, the control circuit 110 will determine if the first time period has passed (step 601).

If the first time period has not yet passed, the control circuit 110 will, at step 602, determine if the first sensor unit 113 is detecting the presence of the oral surface. As noted above, the first sensor unit 113 can either be blocked by fluids in the mouth and/or unable to see the oral surface due to the orientation or position of the oral care tool 310. If it is determined at step 602 that the first sensor unit 113 is not detecting the oral care surface, the control circuit 110 will generate the third user perceptible stimulus with the sensor indicator unit 114 (step 603) to provide a signal to the user that the oral care tool 310 should be rinsed to clear fluids from the first sensor unit 113 and/or the orientation/position of the oral care tool 310 should be changed. If the first time period has not yet passed and the first sensor unit 113 is detecting the presence of the oral care surface at step 602, then, in one embodiment, the control circuit 110 will generate the second user perceptible stimulus with the sensor indicator unit 114 (step 604). This will signal to the user either: (1) there is plaque on the oral surface in the current zone, so you should not move to the next zone; and/or (2) you have not brushed in the current zone for long enough, so you should not move to the next zone.

Although in the exemplified embodiment, the oral care circuit 110 generates the second user perceptible stimulus at step 604, the invention is not to be so limited. In other embodiments, if the first time period has not passed and the first sensor unit is detecting the presence of the oral surface, the control circuit 110 may either: (1) not generate any user perceptible stimulus with the sensor indicator unit 114; or (2) generate the second user perceptible stimulus with the sensor indicator unit 114. For example, if during the first time period in a single zone the first sensor unit 113 is detecting plaque, the control circuit 110 may generate the second user perceptible stimulus with the sensor indicator unit 114. However, if during the first time period in the single zone the first sensor unit 113 is not detecting plaque, the control circuit 110 may not generate any user perceptible stimulus. This is because no plaque is detected, but also the control circuit 110 does not want to signal to the user that it is permissible to move to the next zone. Thus, variations of this are possible, but generally the control circuit 110 will not generate the first user perceptible stimulus with the sensor indicator unit 114 prior to elapse of the first time period in a single zone regardless of whether the first sensor unit 113 is detecting plaque or not.

Returning back to step 601, as noted above the control circuit 110 determines whether the first time period has elapsed. If the answer is yes that the first time period has elapsed, the control circuit 110 will determine whether the second time period has elapsed (step 605). As noted above, if the second time period has elapsed, it will be determined that the user has been cleaning the same zone for the maximum amount of time, and therefore it is time to move to the next zone. Thus, in some embodiments if the second time period has passed, the control unit 110 will generate the first user perceptible stimulus with the sensor indicator unit 114 regardless of whether the first sensor unit 113 is detecting plaque and regardless of whether first sensor unit 113 is detecting the presence of the oral surface.

However, in the exemplified embodiment there is a slight modification to this. In the exemplified embodiment, if at step 605 it is determined that the second time period has passed, the control circuit 110 will determine at step 606 if the first sensor unit 113 is detecting the presence of the oral surface. If the first sensor unit 113 is not detecting the presence of the oral surface, the control circuit 110 will generate the third user perceptible stimulus with the sensor indicator unit 114 (step 603). If the first sensor unit 113 is detecting the presence of the oral surface, the control circuit 110 will generate the first user perceptible stimulus with the sensor indicator unit (step 607). As mentioned above, step 606 may be omitted in some embodiments and if the answer at step 605 is yes, the control circuit 110 will continue to step 607 regardless of any other data being acquired by the first sensor unit 113. As noted above, generation of the first user perceptible stimulus with the sensor indicator unit 114 will signal or prompt the user to move the oral care tool 310 to a different zone of the user's oral cavity for working.

As noted above, if the second time period has passed, the control circuit 110 does not take into consideration whether the first sensor unit 113 is detecting plaque or not in determining which user perceptible stimulus to generate with the sensor indicator unit 114. This is because once the second time period has passed the control circuit 110 signals to the user that it is time to move to the next zone, regardless of whether or not plaque is being detected. The first user perceptible stimulus being generated by the sensor indicator unit 114 provides the necessary signal/prompt to the user to move to the next zone.

Referring back to step 605, the control circuit 110 determines whether the second time period has passed. If the answer to this is no, the control circuit 110 determines that the user has been working with the oral care tool 310 in the same zone for a period of time that is greater than the first time period (minimum amount of time for brushing in a particular zone) and less than the second time period (maximum amount of time for brushing in a particular zone). Thus, as mentioned above, it is within this intermediate time period that the detection of the oral malady (e.g., plaque) with the first sensor unit 113 becomes relevant to the user perceptible stimuli generated by the sensor indicator unit 114.

Once the control circuit 110 determines that the first time period has passed at step 601 but the second time period has not passed at stop 605, the control circuit determines whether the first sensor unit 113 is detecting the presence of the oral care surface at step 608. If the first sensor unit 113 is not detecting the presence of the oral care surface, the control circuit 110 generates the third user perceptible stimulus with the sensor indicator unit 114 (step 609). If the first sensor unit 113 is detecting the presence of the oral care surface, the control circuit 110 determines whether the first sensor unit 113 is detecting the presence of the oral malady (e.g., plaque) on the oral surface (step 610). If the first sensor unit 113 is detecting the presence of the oral malady at step 610, the control circuit 110 will generate the second user perceptible stimulus with the sensor indicator unit 114 (step 611). This will signal to the user to continue working in the same zone because the maximum time period has not yet elapsed and there is still the existence of the oral malady (e.g., plaque) on the oral surfaces. If the first sensor unit 113 is not detecting the presence of the oral malady at step 610 (during a time at which the oral care tool 310 has been working in the same zone for an amount of time that is greater than the first time period and less than the second time period), the control circuit 110 will generate the first user perceptible stimulus with the sensor indicator unit 114 (step 612). This will signal to the user that the minimum time period (the first time period) has passed and there is no evidence of the oral malady on the oral surface, so the user can move the oral care tool 310 to the next zone of the user's oral cavity for working.

As noted, the above operation set forth with regard to FIG. 25 all occurs while the oral care tool 310 is positioned within a single (the same) zone. Once the control circuit 110 determines that the oral care tool 310 has been moved out of the zone and into a different zone, the zone timer will reset and the control operations will start again at step 600. The flow of operation indicated in FIG. 25 occurs so long as the control circuit determines (via the first sensor unit 113, the second sensor unit 117, or some combination thereof) that the oral care tool 310 remains in the same zone of the oral cavity.

To state succinctly, in one embodiment upon the zone timer starting, the sensor indicator unit 114 generates the second user perceptible stimulus (e.g., blue light). The sensor indicator unit 114 continues to generate the second user perceptible stimulus (e.g., blue light) for the first time period (e.g., five seconds). After the first time period (e.g., five seconds_, the sensor indicator unit 114 continues to generate the second user perceptible stimulus (e.g., blue light) only if the oral malady (e.g., plaque) is detected by the first sensor unit 113. After the first time period (e.g., seconds) if the oral malady (e.g., plaque) is not detected by the first sensor unit 113, the sensor indicator unit 114 changes from generating the second user perceptible stimulus (e.g., blue light) to generating the first user perceptible stimulus (e.g., white light) to signal the user to move to a new zone. After a second period of time (e.g., ten seconds) in the same zone, the sensor indicator unit 114 generates the first user perceptible stimulus (e.g., white light) to signal the user to move to a new zone regardless of whether the oral malady (e.g., plaque) is detected by the first sensor unit 113. All the while, if the first sensor unit 113 is blocked at any time, the sensor indicator unit 114 generates the third user perceptible stimulus (e.g., red light). As soon as the control circuit 110 detects or determines that the oral care tool 310 has moved to a new zone, the control circuit 110 generates the second user perceptible stimulus (e.g., blue light) with the sensor indicator unit 114 to start the process over.

In some embodiments in addition to a three-dimensional model of the mouth map being shown on the display of the electronic device 500 (see FIG. 3), a three-dimensional model of the oral care implement 100 with the light ring (color coded to show white, blue, or red light as set forth above) is also displayed on the display of the electronic device 500 through the toothbrush app 123. The three-dimensional model of the oral care implement 100 may just be a part of the oral care implement (for example) and it may be shown in the three-dimensional model of the mouth map within the zone that is currently being brushed. In some embodiments, the entire three-dimensional model of the oral care implement or portions there of are color-coded to match the color of the light ring 299 to provide appropriate indications, signals, and prompts to the user as set forth herein.

In some embodiments, upon the sensor indicator unit 114 having been activated to generate the first user perceptible stimulus, the control circuit 110 may restart the zone timer and then immediately subsequently deactivate generation of the first user perceptible stimulus (and start the operation back at step 600 of FIG. 24). This is because generation of the first user perceptible stimulus is a signal or prompt for the user to move to a different zone, so the assumption is that this action has taken place and so the zone timer should be restarted. Specifically, the first user perceptible stimulus is only generated when the minimum time period has passed and the oral malady is not detected so a user should move to another zone for working/cleaning. In other embodiments, the zone timer may only be restarted when the control circuit 110, via data acquired by the first sensor unit and/or the second sensor unit 117, determines that the oral care tool 310 has been moved to a different zone.

Figure 26:
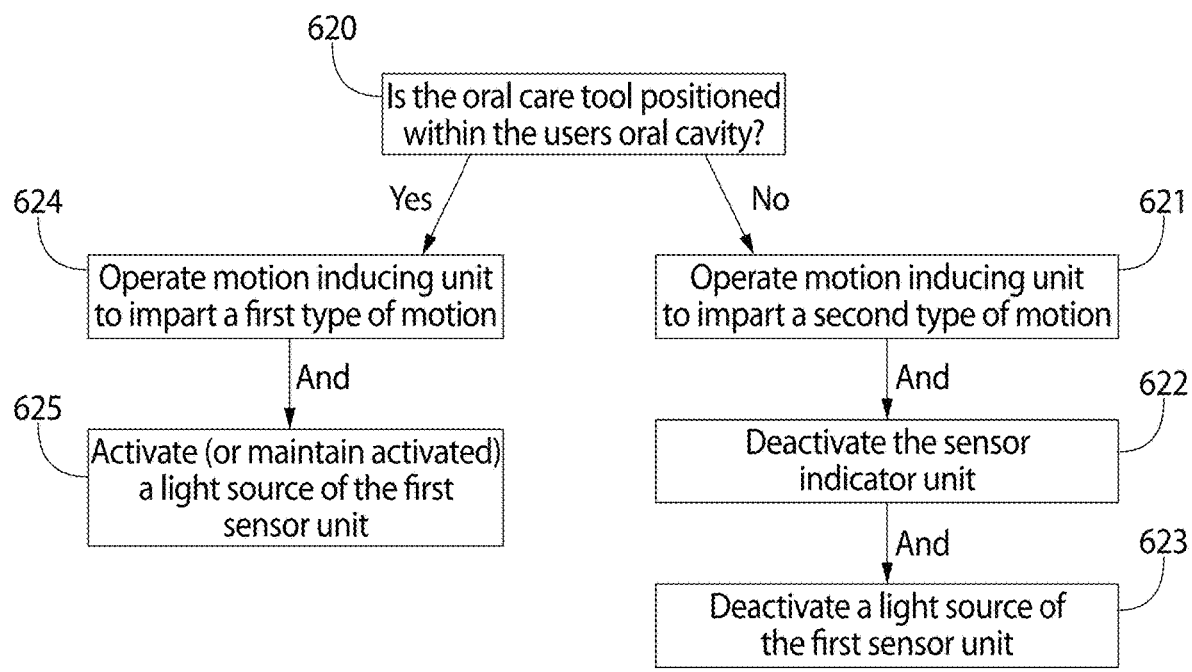
FIG. 26 is a flow chart showing operation of the control circuit of the oral care implement of FIG. 1 in accordance with an embodiment of the present invention.

Referring to FIG. 26, some additional operations of the oral care system 10, and particularly the control circuit 110 thereof, will be described. As mentioned above, one state that is continuously monitored by the control circuit 110 is whether the oral care tool 310 is positioned within the user's oral cavity or not (step 620). If the oral care implement 100 is powered on and it is determined that the oral care tool 310 is not positioned in the user's oral cavity, several results will occur. First, the motion inducing unit 119 will operate to impart a first type of motion to the oral care tool (step 621). The first type of motion may be a low power state such that the motion inducing unit 119 is operating at less than its maximum speed. Second, the sensor indicator unit 114 is deactivated (622). This means that regardless of any detections made by the first sensor unit 113, when the oral care tool 310 is positioned outside of the user's oral cavity the sensor indicator unit 114 will not generate any output or user perceptible stimulus. As mentioned above, in some embodiments the first sensor unit 113 may comprise the optical sensor 140, the light source 141, and the receiver 142. The third operation that occurs when the oral care tool 310 is determined to be outside of the user's oral cavity is that the light source 141 of the first sensor unit 113 is deactivated (or, if already deactivated, it will be maintained in that deactivated state) (step 623).

Alternatively, if the oral care tool 310 is determined to be located within the user's oral cavity, first the motion inducing unit 119 will operate to impart a second type of motion to the oral care tool 310 (step 624). The second type of motion may be different than the first type of motion noted above so that the motion inducing unit 119 imparts different types of motion depending on whether the oral care tool 310 is located within the user's oral cavity or not. The second type of motion may be a full power state such that the motion inducing unit 119 is operating at its maximum speed. Of course, in other embodiments the first and second types of motion may differ based on the pattern of motion, having various on/off times in a pulsing pattern, or the like. Second, when the oral care tool 310 is determined to be positioned within the user's oral cavity, the light source 141 of the first sensor unit 113 is activated or maintained in the activated state if it was previously activated.

As noted previously, in some embodiments there may be a preconfigured session time for a particular oral care session. At the completion of the session time, the timer indicator unit 116 is completely illuminated (i.e., the illumination ring 150 is completely lit up). Furthermore, in some embodiments at the completion of the session time the motion inducing unit 119 may pulsate with several on/off states to indicate to the user the completion of the session time. For example, in one embodiment after completion of the session time the motion inducing unit 119 will operate with an off period of 210 ms, an on period of 490 ms, an off period of 210 ms, an on period of 490 ms, and another off period of 210 ms (of course, the specific time periods associated with the on/off periods of the motor are merely exemplary). After the final off period, the motion inducing unit 119 may proceed back to its normal operation (i.e., imparting the second type of motion to the oral care tool 310 if it is in the oral cavity and imparting the first type of motion to the oral care tool 310 if it is not in the oral cavity). After an extended time period, the motion inducing unit 119 may be powered off or otherwise stop. In some embodiments, the session time period may be two minutes and the extended time period may be three minutes, or four minutes, or the like.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care system comprising:
an oral care implement comprising an oral care tool for treating an oral cavity of a user;
a control circuit comprising, in operable cooperation:
a power source integrated into the oral care implement;
a first sensor unit integrated into the oral care implement and configured to monitor an oral care parameter during performance of an oral care session using the oral care implement;
a sensor indicator unit integrated into the oral care implement and configured to generate user perceptible stimuli during the oral care session upon the first sensor unit detecting that the monitored oral care parameter meets a certain criteria;
a memory unit configured to store data relating to the monitored oral care parameter; and
a mode selection unit configured to allow a user to select between both of a normal mode and a quiet mode for performance of the oral care session;
wherein upon selection of the normal mode by the user for the oral care session: (i) the first sensor unit is active during the oral care session; (ii) the sensor indicator unit is active during the oral care session; and (iii) the data relating to the monitored oral care parameter is stored in the memory unit during the oral care session; and
wherein upon selection of the quiet mode by the user for the oral care session: (i) the first sensor unit is active during the oral care session; (ii) the sensor indicator unit is inactive during the oral care session; and (iii) the data relating to the monitored oral care parameter is stored in the memory unit during the oral care session.

2. The oral care system according to claim 1 wherein the oral care parameter is a physiological oral condition of the user.

3. The oral care system according to claim 2 wherein the control circuit further comprises:
a second sensor unit configured to determine orientation and/or position of the oral care implement within the user's oral cavity during the oral care session; and
wherein the data relating to the monitored oral care parameter comprises data from both the first sensor unit and the second sensor unit.

4. The oral care system according to claim 3 wherein the control circuit further comprises:
a mapping unit configured to generate an oral cavity map in which locations of the physiological oral condition in the user's oral cavity are identified based on data from both the first sensor unit and the second sensor unit; and
wherein the data relating to the monitored oral care parameter comprises the oral cavity map.

5. The oral care system according to claim 2 wherein the first sensor unit is a plaque detection unit; and wherein the sensor indicator unit generates a first user perceptible stimulus while plaque is being detected on an oral surface by the first sensor unit and a second user perceptible stimulus when the oral surface is determined to be free of plaque by the first sensor unit.

6. The oral care system according to claim 5 wherein the first user perceptible stimulus is light of a first color and the second user perceptible stimuli is light of second color that is different than the first color.

7. The oral care system according to claim 1 wherein the mode selection unit comprises a switch located on the oral care implement.

8. The oral care system according to claim 1 wherein the oral care implement further comprises a motion inducing unit in operable cooperation with the control circuit and configured to impart motion to the oral care tool; and wherein the motion inducing unit is active in both the normal mode and the quiet mode.

9. The oral care system according to claim 1 further comprising:
an electronic device separate from the oral care implement and comprising a display unit; and
the control circuit further comprising a wireless communication unit integrated into the oral care implement for transmitting the data relating to the monitored oral care parameter from the oral care implement to the electronic device.

10. The oral care system according to claim 9 wherein the wireless communication unit is active in both the normal mode and the quiet mode.

11. The oral care system according to claim 1 further comprising:
the control circuit further comprising:
a timer unit configured to track time during performance of the oral care session;
a time indicator unit configured to inform the user, during the oral care session, of the time that has passed during performance of the oral care session;
wherein upon selection of the normal mode by the user for the oral care session, the timer unit is active and the time indicator unit is active; and
wherein upon selection of the quiet mode by the user for the oral care session, the timer unit is active and the time indicator unit is inactive.

12. The oral care system according to claim 11 wherein the memory unit is configured to store data relating to the time tracked during the during performance of the oral care session.

13. The oral care system according to claim 11 wherein the time indicator unit is integrated into the oral care implement.

14. The oral care system according to claim 1 further comprising:
the control circuit further comprising:
a timer unit configured to track time during performance of the oral care session;
a time indicator unit configured to inform the user, during the oral care session, of the time that has passed during performance of the oral care session;
wherein the timer unit is active and the time indicator unit is active in both the normal mode and the quiet mode.

15. The oral care system according to claim 1 wherein the oral care implement is a toothbrush and the oral care tool comprises a plurality of tooth cleaning elements.

16. An oral care system comprising:
an oral care implement comprising an oral care tool for treating an oral cavity of a user;
a control circuit configured to operate the oral care implement in at least two user selectable modes comprising a normal mode and a quiet mode;
wherein upon selection of the normal mode by the user for an oral care session: (i) a first sensor unit configured to detect a physiological oral care condition during the oral care session is active; and (ii) a sensor indicator unit that generates user perceptible stimuli during the oral care session in response to the detection of the physiological oral care condition is active; and wherein upon selection of the quiet mode by the user for an oral care session: (i) the first sensor unit is active during the oral care session; and (ii) the sensor indicator unit is inactive during the oral care session.

17. The oral care system according to claim 16 wherein, in both of the quiet mode and the normal mode, data relating to the monitored physiological oral care condition is stored in a memory unit.

18. The oral care system according to claim 17 wherein the first sensor unit is a plaque detection unit; and wherein the sensor indicator unit generates a first user perceptible stimulus while plaque is being detected on an oral surface by the first sensor unit and a second user perceptible stimulus when the oral surface is determined to be free of plaque by the first sensor unit.

19. The oral care system according to claim 16 wherein the oral care implement further comprises a motion inducing unit in operable cooperation with the control circuit and configured to impart motion to the oral care tool; and wherein the motion inducing unit is active in both the normal mode and the quiet mode.

20. A method of operating an oral care implement of an oral care system during an oral care session, the oral care system comprising a control circuit configured to operate the oral care implement in at least two user selectable modes comprising a normal mode and a quiet mode, the method comprising:
  a) receiving a user mode selection selecting a desired one of the normal mode and the quiet mode from the at least two user selectable modes;
  b-1) upon the user mode selection being the normal mode, the oral care implement being activated so that: (i) a first sensor unit is active and monitors for a physiological oral care condition during the oral care session; and (ii) a sensor indicator unit is active and generates user perceptible stimuli during the oral care session in response to the physiological oral care condition being detected by the first sensor unit; and
  b-2) upon the user mode selection being the quiet mode, the oral care implement being activated so that: (i) the first sensor unit is active and monitors for the physiological oral care condition during the oral care session; and (ii) the sensor indicator unit is inactive during the oral care session.

* * * * *